US006331531B1

(12) United States Patent
Kern

(10) Patent No.: US 6,331,531 B1

(45) Date of Patent: Dec. 18, 2001

(54) METHOD FOR CONTROLLING HARMFUL ORGANISMS IN CROPS OF USEFUL PLANTS

(75) Inventor: Manfred Kern, Lörzweiler (DE)

(73) Assignee: Aventis CropScience GmbH, Frankfurt am Main (DE)

(*) Notice: Subject to any disclaimer, the term of this patent is extended or adjusted under 35 U.S.C. 154(b) by 0 days.

(21) Appl. No.: 09/325,148

(22) Filed: Jun. 3, 1999

(30) Foreign Application Priority Data

Jun. 5, 1998 (DE) ............................................. 198 25 333

(51) Int. Cl.[7] ........................ A01N 43/00; A01N 43/653; A01N 37/08; A01N 55/04; A01N 63/00

(52) U.S. Cl. ............................ 514/93; 514/183; 514/256; 514/336; 514/460; 514/464; 514/476; 514/493; 514/521; 514/431

(58) Field of Search .............................. 514/93, 183, 256, 514/336, 460, 464, 476, 493, 521, 431

(56) References Cited

U.S. PATENT DOCUMENTS

| | | | |
|---|---|---|---|
| 5,322,938 | 6/1994 | McPherson et al. | 536/24.1 |
| 6,057,370 * | 5/2000 | Weiland et al. | 514/594 |

FOREIGN PATENT DOCUMENTS

| | | |
|---|---|---|
| 0408403 | 1/1991 | (EP) . |
| 2485334 | 12/1981 | (FR) . |
| WO 97/45017 | 12/1997 | (WO) . |
| WO 9935910 | 7/1999 | (WO) . |

OTHER PUBLICATIONS

Chemical Abstracts, vol. 127, No. 8, Aug. 25, 1997, Abstract No. 105596 identified as XP00213931.

Hamon, n. et al, Worldwide Development of Fipronil Insecticide, Jan. 1, 1996, pp. 759–765, identifed as XP000602846.

Database CABA (online) 1991, Hussein et al., identified as No. XP002117813.

Database CROPU (online) 1997, Burris et al., identified as No. XP002117928.

Database CROPU (online) 1996, Burris et al., identified as No. XP002117935.

Database CROPU (online) 1997, Fife et al., identified as No. XP002117929.

Database CROPU (online) 1993, Johnson et al., identified as No. XP002117936.

Chemical Abstracts, vol. 110, No. 21, May 22, 1989, Abstract No. 187779 identnfied as XP002117927.

Chemical Abstracts, vol. 99, No. 11, Sep. 12, 1983, Abstract No. 83681 identified as XP002117926.

* cited by examiner

*Primary Examiner*—S. Mark Clardy

(74) *Attorney, Agent, or Firm*—Frommer Lawrence & Haug LLP

(57) ABSTRACT

Method for controlling harmful organisms in genetically modified cotton plants which contain a gene derived from *Bacillus thuringiensis* which encodes and expresses an insecticidally active protein, which comprises applying an insecticisally effective amount of one or more compounds from the following groups and a–f, described herein, to the plants, to their seeds or propagation stock and/or to the area in which they are cultivated.

The method according to the invention makes it possible to reduce the application rate of crop protection agents which act synergistically with the transgenic plants, and also to increase and widen the efficacy of the transgenic plants, and therefore offers both economical and ecological advantages.

15 Claims, No Drawings

METHOD FOR CONTROLLING HARMFUL ORGANISMS IN CROPS OF USEFUL PLANTS

The invention relates to a method for controlling harmful organisms in crops of Bt cotton.

Genetically modified cotton plants which express toxins from *Bacillus thuringiensis* (Bt) and which are consequently resistant to attack by certain harmful insects are known and are increasingly employed in commercial agriculture (see, for example, U.S. Pat. No. 5,322,938).

Although cotton which is genetically modified in this way already has very good properties, there are still a number of problems, so that a wide scope for improvement still exists.

For example, Bt toxins are not effective against all important cotton pests (see, for example, Flint, H. M. et al. (1995) Southwestern Entomologist 20/3, 281–292), the efficacy is insufficient at a high infestation intensity (see, for example, EPA Hearing Docket OPP-0478 (1997) Plant Pesticides Resistance Management, The Agriculture Program, The Texas A&M University System, College Station, Tex. 77843), Bt-resistance or Bt-cross-resistance may occur (see, for example, Gould, F. et al. (1997) Proc. Natl. Acad. Sci. USA 94, 3519–3523 or Bauer, L. S. (1995) Florida Entomologist 78/3, 414), or particular parts of plants may differ considerably in their insecticidal activity (see, for example, Lozzia, G. C. and Rigamonti, I. E. (1996) Boll. Zool. agr. Buchic Ser II, 28/1, 51–69).

It was therefore another object to provide the most effective and environmentally compatible problem solutions possible for controlling pests of cotton. WO-A 97/45 017 describes a process for controlling Lepidoptera in Bt cotton where an insecticidally active benzoylurea derivative is additionally used. It is not possible to draw conclusions with respect to the activity of other classes of insecticides from this publication.

Surprisingly, it has now been found that certain classes of insecticides show synergistic effects when used in combination with Bt cotton.

The invention therefore provides a method for controlling harmful organisms in genetically modified cotton plants which contain a gene derived from Bacillus thuringiensis which encodes and expresses an insecticidally active protein, which comprises applying an insecticidally effective amount of one or more compounds from the following groups a–f to the plants, to their seeds or propagation stock and/or to the area in which they are cultivated:

a) Organophosphorus compounds:

triazophos (726), monocrotophos (502), methamidophos (479), chlorpyrifos (137), parathion (551), acephate (4), profenofos (594), malathion (448), heptenophos (395);

b) Pyrethroids:

tralomethrin (718), cypermethrin (183), cyhalothrin (179), (lambda)-cyhalothrin (180), deltamethrin (204), fenvalerates (319), (alpha)-cypermethrin (183/184), cyfluthrin (176), fenpropathrin (312), etofenprox (292);

c) Carbamates:

aldicarb (16), bendiocarb (56), carbaryl (106), carbofuran (109), formetanates (369), pirimicarb (583)

d) Biopesticides:

*Bacillus thuringiensis* (46, 47), granuloses and nuclear polyhedrosis viruses, beauveria bassiana (52), beauveria brogniartii (53), baculoviruses, such as autographa california;

e) Others:

endosulfan (270), abamectin (1), XDE-105 (754), diafenthiuron (208), fipronil (323), chlorfenapyr (123), tebufenocides (679), fenazaquin (301), imidacloprid (418), triazamates (724), fentin (317), amitraz (22), MK-242;

f) 4-Haloalkyl-3-heterocyclylpyridines and 4-haloalkyl-5-heterocyclylpyrimidines of the formula (I), if appropriate also in the form of their salts, (I)

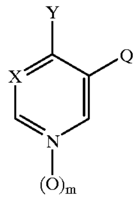

where the symbols and indices have the following meanings:

Y is halo-$C_1$–$C_6$-alkyl;

X is CH or N;

m is 0 or 1;

Q is a 5-membered heterocyclic group

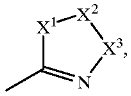

in which

| | | | | |
|---|---|---|---|---|
| a) | $X^1 = W$, | $X^2 = NR^a$, | $X^3$ $CR^bR^1$ | or |
| b) | $X^1 = NR^a$, | $X^2 = CR^bR^1$, | $X^3 = W$ | or |
| c) | $X^1 = V$, | $X^2 = CR^aR^1$ | | |
| d) | $X^1 = V$, | $X^2 = CR^aR^2$, | $X^3 = CR^bR^3$ | or |
| e) | $X^1 = V$, | $X^2 = CR^4R^5$, | $X^3 = CR^6R^7$ | or |
| f) | $X^1 = NR^a$, | $X^2 = CR^bR^1$, | $X^3 = NR^8$; | |

$R^a$ and $R^b$ together are a bond

V is oxygen, sulfur or $NR^9$;

W is oxygen or sulfur;

$R^1$ is hydrogen, ($C_1$–$C_{20}$)-alkyl, ($C_2$–$C_{20}$)-alkenyl, ($C_2$–$C_{20}$)-alkynyl, ($C_3$–$C_8$)-cycloalkyl, ($C_4$–$C_8$)-cycloalkenyl, ($C_6$–$C_8$)-cycloalkynyl, where the six last-mentioned radicals are optionally substituted by one or more radicals from the group halogen, cyano, nitro, hydroxyl, $—C(=W)R^{10}$, $—C(=NOR^{10})R^{10}$, $—C(=NNR^{10}_2)R^{10}$, $—C(=W)OR^{10}$, $—C(=W)NR^{10}_2$, $—OC(=W)R^{10}$, $—OC(=W)OR^{10}$, $—NR^{10}C(=W)R^{10}$, $—N[C(=W)R^{10}]_2$, $—NRC^{10}C(=W)OR^{10}$, $—C(=W)NR^{10}—NR^{10}_2$, $—C(=W)NR^{10}—NR^{10}[C(=W)R^{10}]$, $—NR^{10}—C(=W)NR^{10}_2$, $—NR^{10}—NR^{10}C(=W)R^{10}$, $—NR^{10}—N[C(=W)R^{10}]_2$, $—N[(C=W)R^{10}]—NR^{10}_2$, $—NR^{10}—NR^{10}[(C=W)R^{10}]$, $—NR^{10}—NR^{10}[(C=W)WR^{10}]$, $—NR^{10}—R^{10}[(C=W)NR^{10}_2]$, $—NR^{10}(C=NR^{10})R^{10}$, $—NR\ (C=NR^{10})NR^{10}_2$, —O—$NR^{10}_2$, —O—$NR^{10}$(C=W)$R^{10}$, —$SO_2NR^{10}_2$, —NR $SO_2R^{10}$,
—$SO_2OR^{10}$, —$OSO_2R^{10}$, —$OR^{10}$, —$NR^{10}_2$, —$SR^{10}$, —$SiR^{10}_3$,
—$SeR^{10}$, —$R^{10}_2$, —(=W)$R^{10}_2$,
—$SOR^{10}$, —$SO_2R$ , —$PW_2R^{10}_2$, —$PW_3R^{10}_2$, aryl and heterocyclyl,
the two last-mentioned radicals optionally being substituted by one or more radicals from the group
($C_1$–$C_6$)-alkyl, ($C_2$–$C_6$)-alkenyl, ($C_2$–$C_6$)-alkynyl, ($C_3$–$C_8$)-cycloalkyl, ($C_4$–$C_8$)-cycloalkenyl, ($C_6$–$C_8$)-cycloalkynyl, ($C_1$–$C_6$)-haloalkyl, ($C_2$–$C_6$)-haloalkenyl, ($C_2$-$C_6$)-haloalkynyl, halogen, —$OR^{10}$, —$NR^{10}_2$, —$SR^{10}$, $SiR^{10}_3$, —C(=W)$R^{10}$, —C(=W)$OR^{10}$, C(W)$NR^{10}_2$, —$SOR^{10}$, —$SO_2R^{10}$, nitro, cyano and hydroxyl, aryl,
which is optionally substituted by one or more radicals from the group
($C_1$–$C_6$)-alkyl, ($C_2$–$C_6$)-alkenyl, ($C_2$–$C_6$)-alkynyl, ($C_3$–$C_8$)-cycloalkyl, ($C_4$–$C_8$)-cycloalkenyl and ($C_6$–$C_8$)-cycloalkynyl, where these six abovementioned radicals are optionally substituted by one or more radicals from the group
halogen, cyano, nitro, —C(=W)$R^{10}$, —C(=W)$OR^{10}$,
—C(=W)$NR^{10}_2$, —$OR^{10}$, $NR^{10}_2$, —$SR^{10}$, —$SOR^{10}$ and
—$SO_2R^{10}$,
halogen, cyano, nitro, —C(=W)$R^{10}$, —C(=NOR )$R^{10}$,
—C(=$NNR^{10}_2$)$R^{10}$, —C(=W)$OR^{10}$, —C(=W)$NR^{10}_2$, —OC(=W)$R^{10}$,
—OC(=W)$OR^{10}$, —$NR^{10}$C(=W)$R^{10}$, —N[C(=W)$R^{10}$]$_2$,
—$NR^{10}$C(=W)$OR^{10}$, —$OR^{10}$, —$NR^{10}_2$, —$SR^{10}$, —$SiR^{10}_3$, —$PR^{10}_2$, —$SOR^{10}$, —$SO_2R^{10}$, —$PW_2R^{10}_2$ and —$PW_3R^{10}_2$, heterocyclyl,
which is optionally substituted by one or more radicals from the group
($C_1$–$C_6$)-alkyl, ($C_2$–$C_6$)-alkenyl, ($C_2$–$C_6$)-alkynyl, ($C_3$–$C_8$)-cycloalkyl, ($C_4$–$C_8$)-cycloalkenyl and ($C_6$–$C_8$)-cycloalkynyl, where the six abovementioned radicals are optionally substituted by one or more radicals from the group
cyano, nitro, halogen, —C(=W)$R^{10}$, —C(=W)$OR^{10}$,
—C(=W)$NR^{10}_2$, —$NR^{10}$C(=W)$R^{10}$, —N[C(=W)$R^{10}$]$_2$,
—OC(=W)$R^{10}$, —OC(=W)$OR^{10}$, —$OR^{10}$, —$NR^{10}_2$, —$SR^{10}$,
—$SOR^{10}$ and —$SO_2R^{10}$,
halogen, cyano, nitro, —C(=W)$R^{10}$, —C(=W)$OR^{10}$,
—C(=W)$NR^{10}_2$, —OC(=W)$R^{10}$, —$OR^{10}$, —$NR^{10}_2$, —$SR^{10}$, —$SOR^{10}$ and —$SO_2R^{10}$, —$OR^{10}$, —$NR^{10}_2$, —$SR^{10}$, —$SOR^{10}$$_{10}$, —$SO_2R^{10}$, —C(=W)$R^{10}$,
—C(=$NOR^{10}$)$R^{10}$, —C(=$NNR^{10}_2$)$R^{10}$, —C(=W)$OR^{10}$,
—C(=W)$NR^{10}_2$, —OC(=W)$R^{10}$, —OC(=W)$OR^{10}$, —NR OC(=W)$R^{10}$, —N[C(=W)$R^{10}$]$_2$, —$NR^{10}$, —(=W)$OR^{10}$, —C(=W)$NR^{10}$, —$NR^{10}_2$,
—C(=W)$R^{10}$, —$NR^{10}$C[(=W)$R^{10}$], —$NR^{10}$—C(=W)$R^{10}_2$, —$NR^{10}$—$NR^{10}$C(=W)$R^{10}$, —$NR^{10}$—NC(=W)$R^{10}_2$, —N(C=W)$R^{10}$—$NR^{10}_2$,
—$NR^{10}$, —$NR^{10}$[(C=W)$R^{10}$], —$NR^{10}$—$NR^{10}$[(C=W)$WR^{10}$], —$NR^{10}$—$NR^{10}$[(C=W)$NR^{10}_2$], —$NR^{10}$(C=$NR^{10}$)$R^{10}$,
—$NR^{10}$(C=$NR^{10}$)$NR^{10}_2$, —O—$NR^{10}_2$, —O—$NR^{10}$(C=W)$R^{10}$,
—$SO_2NR^{10}_2$, —NR $SO_2R^{10}$, —$SO_2OR^{10}$, —$OSO_2R^{10}$,
—SC(=W)$R^{10}$, —SC(=W)$OR^{10}$, —SC(=W)$R^{10}$, —$PR^{10}_2$, —$PW_2R^{10}_2$,
—$PW_3R^{10}_2$, $SiR^{10}_3$ or halogen;

$R^2$ and $R^3$ independently of one another have the definitions given in $R^1$;

$R^2$ and $R^3$ together form a 5- to 7-membered ring which may be partially or fully unsaturated and may be interrupted by one or more atoms from the group nitrogen, oxygen and sulfur, the oxygen atoms not being directly adjacent to one another, and the ring optionally being substituted by one or more, but at most 5, radicals $R^1$;

$R^4$ and $R^6$ independently of one another have the definitions given in $R^1$;

$R^4$ and $R^6$ together form a 4- to 7-membered ring which may be partially or fully unsaturated and may be interrupted by one or more atoms from the group nitrogen, oxygen and sulfur, the oxygen atoms not being directly adjacent to one another, and the ring optionally being substituted by one or more, but at most 5, radicals $R^1$;

$R^5$ and $R^7$ independently of one another are hydrogen, ($C_1$–$C_{20}$)-alkyl, ($C_2$–$C_{20}$)-alkenyl, ($C_2$–$C_{20}$)-alkynyl, ($C_3$–$C_8$)-cycloalkyl, ($C_4$–$C_8$)-cycloalkenyl, ($C_6$–$C_8$)-cycloalkynyl,
where the six last-mentioned radicals are optionally substituted by one or more radicals from the group
halogen, cyano, nitro, hydroxyl, —C(=W)$R^{10}$, —C(=$NOR^{10}$)$R^{10}$,
—C(=$NNR^{10}_2$)$R^{10}$, —C(=W)$OR^{10}$, —C(=W)$NR^{10}_2$, —OC(=W)$R^{10}$,
—OC(=W)$OR^{10}$, —$NR^{10}$C(=W)$R^{10}$, —N[C(=W)$R^{10}$]$_2$,
—$NR^{10}$C(=W)$OR^{10}$, —C(=W)$NR^{10}$—$NR^{10}_2$,
—C(=W)$NR^{10}$—$NR^{10}$[C(=W)$R^{10}$], —$NR^{10}$—C(=W)$NR^{10}_2$,
—$NR^{10}$—$NR^{10}$C(=W)$R^{10}$, —$NR^{10}$—N[C(=W)$R^{10}$]$_2$, —N[(C=W)$R^{10}$]—$NR^{10}_2$, —$NR^{10}$—$NR^{10}$[(C=W)$R^{10}$], —$NR^{10}$—$NR^{10}$[(C=W)$WR^{10}$],
—$NR^{10}$—$NR^{10}$[(C=W)$NR^{10}_2$], —$NR^{10}$(C=$NR^{10}$,)$R^{10}$,
—$NR^{10}$(C=$NR^{10}$)$NR^{10}_2$, —O—$NR^{10}_2$, —O—$NR^{10}$(C=W)$R^{10}$,
—$OR^{10}$, —$NR^{10}_2$, —$SR^{10}$, —$SiR^{10}_3$, —$SeR^{10}$, —$PR^{10}_2$,
—P(=W)$R^{10}_2$, —$SOR^{10}$, —$SO_2R^{10}$, —$PW_2R^{10}_2$, —$PW_3R^{10}_2$,
aryl and heterocyclyl,
of which the two mentioned last are optionally substituted by one or more radicals from the group
($C_1$–$C_6$)-alkyl, ($C_2$–$C_6$)-alkenyl, ($C_2$–$C_6$)-alkynyl, ($C_3$–$C_8$)-cycloalkyl, ($C_4$–$C_8$)-cycloalkenyl, ($C_6$–$C_8$)-cycloalkynyl, ($C_1$–$C_6$)-haloalkyl, ($C_2$–$C_6$)-haloalkenyl, ($C_2$–$C_6$)-haloalkynyl, halogen, —$OR^{10}$, —$NR^{10}_2$, —$SR^{10}$, —$SiRR^{10}_3$, —C(═W)$R^{10}$, —C(═W)$OR^{10}$, —C(═W)$NR^{10}_2$, —$SOR^{10}$, —$SO_2R^{10}$, nitro, cyano and hydroxyl, aryl, which is optionally substituted by one or more radicals from the group ($C_1$–$C_6$)-alkyl, ($C_2$–$C_6$)-alkenyl, ($C_2$–$C_6$)-alkynyl, ($C_3$–$C_8$)-cycloalkyl, ($C_4$–$C_8$)-cycloalkenyl and ($C_6$–$C_8$)-cycloalkynyl, where these six abovementioned radicals are optionally substituted by one or more radicals from the group halogen, cyano, nitro, —C(═W)$R^{10}$, —C(═W)$OR^{10}$, —C(═W)$NR^{10}_2$, —$OR^{10}$, —$NR^{10}_2$, —$SR^{10}$, —$SOR^{10}$ and —$SO_2R^{10}$, halogen, cyano, nitro, —C(═W)$R^{10}$, —C(═$NOR^{10}$)$R^{10}$, —C(═$NNR^{10}_2$)$R^{10}$, —C(═W)$OR^{10}$, —C(═W)$NR^{10}_2$, —OC(═W)$R^{10}$, —OC(═W)$OR^{10}$, —NR C(═W)$R^{10}$, —N[C(═W)$R^{10}$]$_2$, —$NR^{10}$C(═W)$OR^{10}$, —$OR^{10}$, —$NR^{10}_2$, —$SR^{10}$, —$SiR^{10}_3$, —$PR^{10}_3$, —$SOR^{10}$, —$SO_2R^{10}$, —$PW_2R^{10}_2$ and —$PW_3R^{10}_2$, pyridyl, which is optionally substituted by one or more radicals from the group ($C_1$–$C_6$)-alkyl, ($C_2$–$C_6$)-alkenyl, ($C_2$–$C_6$)-alkynyl, ($C_3$–$C_8$)-cycloalkyl, ($C_4$–$C_8$)-cycloalkenyl and ($C_6$–$C_8$)-cycloalkynyl, where the six abovementioned radicals are optionally substituted by one or more radicals from the group cyano, nitro, halogen, —C(═W)$R^{10}$, —C(═W)$OR^{10}$, —C(═W)$NR^{10}_2$, —$OR^{10}$, —$NR^{10}_2$, —$SR^{10}$, —$SOR^{10}$ and —$SO_2R^{10}$, halogen, cyano, nitro, —C(═W)$R^{10}$, —C(═W)$OR^{10}$, —C(═W)$NR^{10}_2$, —OC(═W)$R^{10}$, $OR^{10}$, —$NR^{10}_2$, —$SR^{10}$, —$SOR^{10}$, and —$SO_2R^{10}$, —C(═W)$R^{10}$, —C(═$NOR^{10}$)$R^{10}$, —C(═$NNR^{10}_2$)$R^{10}$, —C(═W)$OR^{10}$, —C(═W)$NR^{10}_2$ or halogen;

$R^4$ and $R^5$ together form a 4- to 7-membered ring which may be partially unsaturated and may be interrupted by one or more atoms from the group nitrogen, oxygen and sulfur, oxygen atoms not being directly adjacent to one another, and the ring optionally being substituted by one or more, but at most 5, radicals $R^1$;

$R^6$ and $R^5$ together form one of the groups ═O, ═S or ═N—$R^9$;

$R^6$ and $R^7$ together form a 5- to 7-membered ring which may be partially unsaturated and may be interrupted by one or more atoms from the group nitrogen, oxygen and sulfur, oxygen atoms not being directly adjacent to one another, and the ring optionally being substituted by one or more, but at most 5, radicals $R^1$;

$R^6$ and $R^7$ together form one of the groups ═O, ═S or ═N—$R^9$;

$R^8$ is hydrogen, ($C_1$–$C_6$)-alkyl, ($C_2$–$C_6$)-alkenyl, ($C_2$–$C_6$)-alkynyl, ($C_3$–$C_8$)-cycloalkyl, ($C_4$–$C_8$)-cycloalkenyl, ($C_3$–$C_8$)-cycloalkyl-($C_1$–$C_4$)-alkyl, ($C_4$–$C_8$)-cycloalkenyl-($C_1$–$C_4$)-alkyl, ($C_3$–$C_8$)-cycloalkyl-($C_2$–$C_4$)-alkenyl, ($C_4$–$C_8$)-cycloalkenyl-($C_1$–$C_4$)-alkenyl, ($C_1$–$C_6$)-alkyl-($C_3$–$C_8$)-cycloalkyl, ($C_2$–$C_6$)-alkenyl-($C_3$–$C_8$)-cycloalkyl, ($C_2$–$C_6$)-alkynyl-($C_3$–$C_8$)-cycloalkyl, ($C_1$–$C_6$)-alkyl-($C_4$–$C_8$)-cycloalkenyl, ($C_2$–$C_6$)-alkenyl-($C_4$–$C_8$)-cycloalkenyl, where the fourteen last-mentioned radicals are optionally substituted by one or more radicals from the group halogen, cyano, nitro, hydroxyl, thio, amino, formyl, ($C_1$–$C_6$)-alkoxy, ($C_2$–$C_6$)-alkenyloxy, ($C_2$–$C_6$)-alkynyloxy, ($C_1$–$C_6$)-haloalkyloxy, ($C_2$–$C_6$)-haloalkenyloxy, ($C_2$–$C_6$)-haloalkynyloxy, ($C_3$–$C_8$)-cycloalkoxy, ($C_4$–$C_8$)-cycloalkenyloxy, ($C_3$–$C_8$)-halocycloalkoxy, ($C_4$–$C_8$)-halocycloalkenyloxy, ($C_3$–$C_8$)-cycloalkyl-($C_1$–$C_4$)-alkoxy, ($C_4$–$C_8$)-cycloalkenyl-($C_1$–$C_4$)-alkoxy, ($C_3$–$C_8$)-cycloalkyl-($C_2$–$C_4$)-alkenyloxy, ($C_4$–$C_8$)-cycloalkenyl-($C_1$–$C_4$)-alkenyloxy, ($C_1$–$C_6$)-alkyl-($C_3$–$C_8$)-cycloalkoxy, ($C_2$–$C_6$)-alkenyl-($C_3$–$C_8$)-cycloalkoxy, ($C_2$–$C_6$)-alkynyl-($C_3$–$C_8$)-cycloalkoxy, ($C_1$–$C_6$)-alkyl-($C_4$–$C_8$)-cycloalkenyloxy, ($C_2$–$C_6$)-alkenyl-($C_4$–$C_8$)-cycloalkenyloxy, ($C_1$–$C_4$)-alkoxy-($C_1$–$C_6$)-alkoxy, ($C_1$–$C_4$)-alkoxy-($C_2$–$C_6$)-alkenyloxy, carbamoyl, ($C_1$–$C_6$)-mono- or dialkylcarbamoyl, ($C_1$–$C_6$)-mono- or dihaloalkylcarbamoyl, ($C_3$–$C_8$)-mono- or dicycloalkylcarbamoyl, ($C_1$–$C_6$)-alkoxycarbonyl, ($C_3$–$C_8$)-cycloalkoxycarbonyl, ($C_1$–$C_6$)-alkanoyloxy, ($C_3$–$C_8$)-cycloalkanoyloxy, ($C_1$–$C_6$)-haloalkoxycarbonyl, ($C_1$–$C_6$)-haloalkanoyloxy, ($C_1$–$C_6$)-alkaneamido, ($C_1$–$C_6$)-haloalkaneamido, ($C_2$–$C_6$)-alkeneamido, ($C_3$–$C_8$)-cycloalkaneamido, ($C_3$–$C_8$)-cycloalkyl-($C_1$–$C_4$)-alkaneamido, ($C_1$–$C_6$)-alkylthio, ($C_2$–$C_6$)-alkenylthio, ($C_2$–$C_6$)-alkynylthio, ($C_1$–$C_6$)-haloalkylthio, ($C_2$–$C_6$)-haloalkenylthio, ($C_2$–$C_6$)-haloalkynylthio, ($C_3$–$C_8$)-cycloalkylthio, ($C_4$–$C_8$)-cycloalkenylthio, ($C_3$–$C_8$)-halocycloalkylthio, ($C_4$–$C_8$)-halocycloalkenylthio, ($C_3$–$C_8$)-cycloalkyl-($C_1$–$C_4$)-alkylthio, ($C_4$–$C_8$)-cycloalkenyl-($C_1$–$C_4$)-alkylthio, ($C_3$–$C_8$)-cycloalkyl-($C_2$–$C_4$)-alkenylthio, ($C_4$–$C_8$)-cycloalkenyl-($C_1$–$C_4$)-alkenylthio, ($C_1$–$C_6$)-alkyl-($C_3$–$C_8$)-cycloalkylthio, ($C_2$–$C_6$)-alkenyl-($C_3$–$C_8$)-cycloalkylthio, ($C_2$–$C_6$)-alkynyl-($C_3$–$C_8$)-cycloalkylthio, ($C_1$–$C_6$)-alkyl-($C_4$–$C_8$)-cycloalkenylthio, ($C_2$–$C_6$)-alkenyl-($C_4$–$C_8$)-cycloalkenylthio, ($C_1$–$C_6$)-alkylsulfinyl, ($C_2$–$C_6$)-alkenylsulfinyl, ($C_2$–$C_6$)-alkynylsulfinyl, ($C_1$–$C_6$)-haloalkylsulfinyl, ($C_2$–$C_6$)-haloalkenylsulfinyl, ($C_2$–$C_6$)-haloalkynylsulfinyl, ($C_3$–$C_8$)- cycloalkylsulfinyl, $(C_4-C_8)$-cycloalkerlylsulfinyl, $(C_3-C_8)$-halocycloalksulfinyl, $(C_4-C_8)$-halocycloalkenylsulfinyl, $(C_3-C_8)$-cycloalkyl-$(C_1-C_4)$-alkylsulfinyl, $(C_4-C_8)$-cycloalkenyl-$(C_1-C_4)$-alkylsulfinyl, $(C_3-C_8)$-cycloalkyl-$(C_2-C_4)$-alkenylsulfinyl, $(C_4-C_8)$-cycloalkenyl-$(C_1-C_4)$-alkenylsulfinyl, $(C_1-C_6)$-alkyl-$(C_3-C_8)$-cycloalkylsulfinyl, $(C_2-C_6)$-alkenyl-$(C_3-C_8)$-cycloalkylsulfinyl, $(C_2-C_6)$-alkynyl-$(C_3-C_8)$-cycloalkylsulfinyl, $(C_1-C_6)$-alkyl-$(C_4-C_8)$-cycloalkenylsulfinyl, $(C_2-C_6)$-alkenyl-$(C_4-C_8)$-cycloalkenylsulfinyl, $(C_1-C_6)$-alkylsulfonyl, $(C_2-C_6)$-alkenylsulfonyl, $(C_2-C_6)$-alkynylsulfonyl, $(C_1-C_6)$-haloalkylsulfonyl, $(C_2-C_6)$-haloalkenylsulfonyl, $(C_2-C_6)$-haloalkynylsulfonyl, $(C_3-C_8)$-cycloalkylsulfonyl, $(C_4-C_8)$-cycloalkenylsulfonyl, $(C_3-C_8)$-halocycloalkylsulfonyl, $(C_4-C_8)$-halocycloalkenylsulfonyl, $(C_3-C_8)$-cycloalkyl-$(C_1-C_4)$-alkylsulfonyl, $(C_4-C_8)$-cycloalkenyl-$(C_1-C_4)$-alkylsulfonyl, $(C_3-C_{18})$-cycloalkyl-$(C_2-C_4)$-alkenylsulfonyl, $(C_4-C_8)$-cycloalkenyl-$(C_1-C_4)$-alkenylsulfonyl, $(C_1-C_6)$-alkyl-$(C_3-C_8)$-cycloalkylsulfonyl, $(C_2-C_6)$-alkenyl-$(C_3-C_8)$-cycloalkylsulfonyl, $(C_2-C_6)$-alkynyl-$(C_3-C_8)$-cycloalkylsulfonyl, $(C_1-C_6)$-alkyl-$(C_4-C_8)$-cycloalkenylsulfonyl, $(C_2-C_6)$-alkenyl-$(C_4-C_8)$-cycloalkenylsulfonyl, $(C_1-C_6)$-alkylamino, $(C_2-C_6)$-alkenylamino, $(C_2-C_6)$-alkynylamino, $(C_1-C_6)$-haloalkylamino, $(C_2-C_6)$-haloalkenylamino, $(C_2-C_6)$-haloalkynylamino, $(C_3-C_8)$-cycloalkylamino, $(C_4-C_8)$-cycloalkenylamino, $(C_3-C_8)$-halocycloalkamino, $(C_4-C_8)$-halocycloalkenylamino, $(C_3-C_8)$-cycloalkyl-$(C_1-C_4)$-alkylamino, $(C_4-C_8)$-cycloalkenyl-$(C_1-C_4)$-alkylamino, $(C_3-C_8)$-cycloalkyl-$(C_2-C_4)$-alkenylamino, $(C_4-C_8)$-cycloalkenyl-$(C_1-C_4)$-alkenylamino, $(C_1-C_6)$-alkyl-$(C_3-C_8)$-cycloalkylamino, $(C_2-C_6)$-alkenyl-$(C_3-C_8)$-cycloalkylamino, $(C_2-C_6)$-alkynyl-$(C_3-C_8)$-cycloalkylamino, $(C_1-C_6)$-alkyl-$(C_4-C_8)$-cycloalkenylarnino, $(C_2-C_6)$-alkenyl-$(C_4-C_8)$-cycloalkenylamino, $(C_1-C_6)$-trialkylsilyl, aryl, aryloxy, arylthio, arylamino, arylcarbamoyl, aroyl, aroyloxy, aryloxycarbonyl, aryl-$(C_1-C_4)$-alkoxy, aryl-$(C_2-C_4)$-alkenyloxy, aryl-$(C_1-C_4)$-alkylthio, aryl-$(C_2-C_4)$-alkenylthio, aryl-$(C_1-C_4)$-alkylamino, aryl-$(C_2-C_4)$-alkenylamino, aryl-$(C_1-C_6)$-dialkylsilyl, diaryl-$(C_1-C_6)$-alkylsilyl, triarylsilyl and 5- or 6-membered heterocyclyl, of which the nineteen last-mentioned radicals are optionally substituted in their cyclic moiety by one or more substituents from the group halogen, cyano, nitro, amino, hydroxyl, thio, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkylamino, $(C_1-C_4)$-haloalkylamino, formyl and $(C_1-C_4)$-alkanoyl, aryl, which is optionally substituted by one or more radicals from the group halogen, cyano, nitro, hydroxyl, thio, amino, formyl, $(C_1-C_6)$-alkoxy, $(C_2-C_6)$-alkenyloxy, $(C_2-C_6)$-alkynyloxy, $(C_1-C_6)$-haloalkyloxy, $(C_2-C_6)$-haloalkenyloxy, $(C_2-C_6)$-haloalkynyloxy, $(C_3-C_8)$-cycloalkoxy, $(C_4-C_8)$-cycloalkenyloxy, $(C_3-C_8)$-halocycloalkoxy, $(C_4-C_8)$-halocycloalkenyloxy, carbamoyl, $(C_1-C_6)$-mono- or dialkylcarbamoyl, $(C_1-C_6)$-alkoxycarbonyl, $(C_1-C_6)$-alkanoyloxy, $(C_1-C_6)$-mono- or dihaloalkylcarbamoyl, $(C_1-C_6)$-haloalkoxycarbonyl, $(C_1-C_6)$-haloalkanoyloxy, $(C_1-C_6)$-alkaneamido, $(C_1-C_6)$-haloalkaneamido, $(C_2-C_6)$-alkeneamido, $(C_1-C_6)$-alkylthio, $(C_2-C_6)$-alkenylthio, $(C_2-C_6)$-alkynylthio, $(C_1-C_6)$-haloalkylthio, (($C_2-C_6$)-haloalkenylthio, $(C_2-C_6)$-haloalkynylthio, $(C_3-C_8)$-cycloalkylthio, $(C_4-C_8)$-cycloalkenylthio, $(C_3-C_8)$-halocycloalkthio, $(C_3-C_8)$-halocycloalkenylthio, $(C_1-C_6)$-alkylsulfinyl, $(C_2-C_6)$-alkenylsulfinyl, $(C_2-C_6)$-alkynylsulfinyl, $(C_1-C_6)$-haloalkylsulfinyl, $(C_2-C_6)$-haloalkenylsulfinyl, $(C_2-C_6)$-haloalkynylsulfinyl, $(C_3-C_8)$-cycloalkylsulfinyl, $(C_4-C_8)$-cycloalkenylsulfinyl, $(C_3-C_8)$-halocycloalksulfinyl, $(C_4-C_8)$-halocycloalkenylsulfinyl, $(C_1-C_6)$-alkylsulfonyl, $(C_2-C_6)$-alkenylsulfonyl, $(C_2-C_6)$-alkynylsulfonyl, $(C_1-C_6)$-haloalkylsulfonyl, $(C_2-C_6)$-haloalkenylsulfonyl, $(C_2-C_6)$-haloalkynylsulfonyl, $(C_3-C_8)$-cycloalkylsulfonyl, $(C_4-C_8)$-cycloalkenylsulfonyl, $(C_3-C_8)$-halocycloalksulfonyl, $(C_4-C_8)$-halocycloalkenylsulfonyl, $(C_1-C_6)$-alkylamino, $(C_2-C_6)$-alkenylamino, $(C_2-C_6)$-alkynylamino, $(C_1-C_6)$-haloalkylamino, $(C_2-C_6)$-haloalkenylamino, $(C_2-C_6)$-haloalkynylamino, $(C_3-C_8)$-cycloalkylamino, $(C_4-C_8)$-cycloalkenylamino, $(C_3-C_8)$-halocycloalkamino and $(C_4-C_8)$-halocycloalkenylamino, —C(═W)$R^{11}$, $OR^{11}$ or $NR^{11}_2$;

$R^9$ is $(C_1-C_6)$-alkyl, $(C_2-C_6)$-alkenyl, $(C_2-C_6)$-alkynyl, $(C_3-C_8)$-cycloalkyl, $(C_4-C_8)$-cycloalkenyl, $(C_3-C_8)$-cycloalkyl-$(C_1-C_4)$-alkyl, $(C_4-C_8)$-cycloalkenyl-$(C_1-C_4)$-alkyl, $(C_3-C_8)$-cycloalkyl-$(C_2-C_4)$-alkenyl, $(C_4-C_8)$-cycloalkenyl-$(C_1-C_4)$-alkenyl, where the nine last-mentioned radicals are optionally substituted by one or more radicals from the group halogen, cyano, $(C_1-C_6)$-alkoxy, $(C_2-C_6)$-alkenyloxy, $(C_2-C_6)$ alkynyloxy and $(C_1-C_6)$-haloalkyloxy;

$R^{10}$ is hydrogen, $(C_1-C_6)$-alkyl, $(C_2-C_6)$-alkenyl, $(C_2-C_6)$-alkynyl, $(C_3-C_8)$-cycloalkyl, $(C_4-C_8)$-cycloalkenyl, $(C_3-C_8)$-cycloalkyl-$(C_1-C_4)$-alkyl, $(C_4-C_8)$-cycloalkenyl-$(C_1-C_4)$-alkyl, $(C_3-C_8)$-cycloalkyl-$(C_2-C_4)$-alkenyl, $(C_4-C_8)$-cycloalkenyl-$(C_1-C_4)$-alkenyl, $(C_1-C_6)$-alkyl-$(C_3-C_8)$-cycloalkyl, $(C_2-C_6)$-alkenyl-$(C_3-C_8)$-cycloalkyl, $(C_2-C_6)$- alkynyl-(C$_3$–C$_8$)-cycloalkyl, (C$_1$–C$_6$)-alkyl-(C$_4$–C$_8$)-cycloalkenyl, (C$_2$–C$_6$)-alkenyl-(C$_4$–C$_8$)-cycloalkenyl, where the fourteen last-mentioned radicals are optionally substituted by one or more radicals from the group halogen, cyano, nitro, hydroxyl, thio, amino, formyl, (C$_1$–C$_6$)-alkoxy, (C$_2$–C$_6$)-alkenyloxy, (C$_2$–C$_6$)-alkynyloxy, (C$_1$–C$_6$)-haloalkyloxy, (C$_2$–C$_6$)-haloalkenyloxy, (C$_2$–C$_6$)-haloalkynyloxy, (C$_3$–C$_8$)-cycloalkoxy, (C$_4$–C$_8$)-cycloalkenyloxy, (C$_3$–C$_8$)-halocycloalkoxy, (C$_4$–C$_8$)-halocycloalkenyloxy, (C$_3$–C$_8$)-cycloalkyl-(C$_1$–C$_4$)-alkoxy, (C$_4$–C$_8$)-cycloalkenyl-(C$_1$–C$_4$)-alkoxy, (C$_3$–C$_8$)-cycloalkyl-(C$_2$–C$_4$)-alkenyloxy, (C$_4$–C$_8$)-cycloalkenyl-(C$_1$–C$_4$)-alkenyloxy, (C$_1$–C$_6$)-alkyl-(C$_3$–C$_8$)-cycloalkoxy, (C$_2$–C$_6$)-alkenyl-(C$_3$–C$_8$)-cycloalkoxy, (C$_2$–C$_6$)-alkynyl-(C$_3$–C$_8$)-cycloalkoxy, (C$_1$–C$_6$)-alkyl-(C$_4$–C$_8$)-cycloalkenyloxy, (C$_2$–C$_6$)-alkenyl-(C$_4$–C$_8$)-cycloalkenyloxy, (C$_1$–C$_4$)-alkoxy-(C$_1$–C$_6$)-alkoxy, (C$_1$–C$_4$)-alkoxy-(C$_2$–C$_6$)-alkenyloxy, carbamoyl, (C$_1$–C$_6$)-mono- or dialkylcarbamoyl, (C$_1$–C$_6$)-mono- or dihaloalkylcarbamoyl, (C$_3$–C$_8$)-mono- or dicycloalkylcarbamoyl, (C$_1$–C$_6$)-alkoxycarbonyl, (C$_3$–C$_8$)-cycloalkoxycarbonyl, (C$_1$–C$_6$)-alkanoyloxy, (C$_3$–C$_8$)-cycloalkanoyloxy, (C$_1$–C$_6$)-haloalkoxycarbonyl, (C$_1$–C$_6$)-haloalkanoyloxy, (C$_1$–C$_6$)-alkaneamido, (C$_1$–C$_6$)-haloalkaneamido, (C$_2$–C$_6$)-alkeneamido, (C$_3$–C$_8$)-cycloalkaneamido, (C$_3$–C$_8$)-cycloalkyl-(C$_1$–C$_4$)-alkaneamido, (C$_1$–C$_6$)-alkylthio, (C$_2$–C$_6$)-alkenylthio, (C$_2$–C$_6$)-alkynylthio, (C$_1$–C$_6$)-haloalkylthio, (C$_2$–C$_6$)-haloalkenylthio, (C$_2$–C$_6$)-haloalkynylthio, (C$_3$–C$_8$)-cycloalkylthio, (C$_4$–C$_8$)-cycloalkenylthio, (C$_3$–C$_8$)-halocycloalkthio, (C$_4$–C$_8$)-halocycloalkenylthio, (C$_3$–C$_8$)-cycloalkyl-(C$_1$–C$_4$)-alkylthio, (C$_4$–C$_8$)-cycloalkenyl-(C$_1$–C$_4$)-alkylthio, (C$_3$–C$_8$)-cycloalkyl-(C$_2$–C$_4$)-alkenylthio, (C$_4$–C$_8$)-cycloalkenyl-(C$_1$–C$_4$)-alkenylthio, (C$_1$–C$_6$)-alkyl-(C$_3$–C$_8$)-cycloalkylthio, (C$_2$–C$_6$)-alkenyl-(C$_3$–C$_8$)-cycloalkylthio, (C$_2$–C$_6$)-alkynyl-(C$_3$–C$_8$)-cycloalkylthio, (C$_1$–C$_6$)-alkyl-(C$_4$–C$_8$)-cycloalkenylthio, (C$_2$–C$_6$)-alkenyl-(C$_4$–C$_8$)-cycloalkenylthio, (C$_1$–C$_6$)-alkylsulfinyl, (C$_2$–C$_6$)-alkenylsulfinyl, (C$_2$–C$_6$)-alkynylsulfinyl, (C$_1$–C$_6$)-haloalkylsulfinyl, (C$_2$–C$_6$)-haloalkenylsulfinyl, (C$_2$–C$_6$)-haloalkynylsulfinyl$_1$ (C$_3$–C$_8$)-cycloalkylsulfinyl, (C$_4$–C$_8$)-cycloalkenylsulfinyl, (C$_3$–C$_8$)-halocycloalksulfinyl, (C$_4$–C$_8$)-halocycloa lkeny isulfiny l, (C$_3$–C$_8$)-cycloalkyl-(C$_1$–C$_4$)-alkylsulfinyl, (C$_4$–C$_8$)-cycloalkenyl-(C$_1$–C$_4$)-alkylsulfinyl, (C$_3$–C$_8$)-cycloalkyl-(C$_2$–C$_4$)-alkenylsulfinyl, (C$_4$–C$_8$)-cycloalkenyl-(C$_1$–C$_4$)-alkenylsulfinyl, (C$_1$–C$_6$)-alkyl-(C$_3$–C$_8$)-cycloalkylsulfinyl, (C$_2$–C$_6$)-alkenyl-(C$_3$–C$_8$)-cycloalkylsulfinyl, (C$_2$–C$_6$)-alkynyl-(C$_3$–C$_8$)-cycloalkylsulfinyl, (C$_1$–C$_6$)-alkyl-(C$_4$–C$_8$)-cycloalkenylsulfinyl, (C$_2$–C$_6$)-alkenyl-(C$_4$–C$_8$)-cycloalkenylsulfinyl, (C$_1$–C$_6$)-alkylsulfonyl, (C$_2$–C$_6$)-alkenylsulfonyl, (C$_2$–C$_6$)-alkynylsulfonyl, (C$_1$–C$_6$)-haloalkylsulfonyl, (C$_2$–C$_6$)-haloalkenylsulfonyl, (C$_2$–C$_6$)-haloalkynylsulfonyl, (C$_3$–C$_8$)-cycloalkylsulfonyl, (C$_4$–C$_8$)-cycloalkenylsulfonyl, (C$_3$–C$_8$)-halocycloalksulfonyl, (C$_4$–C$_8$)-halocycloalkenylsulfonyl, (C$_3$–C$_8$)-cycloalkyl-(C$_1$–C$_4$)-alkylsulfonyl, (C$_4$–C$_8$)-cycloalkenyl-(C$_1$–C$_4$)-alkylsulfonyl, (C$_3$–C$_8$)-cycloalkyl-(C$_2$–C$_4$)-alkenylsulfonyl, (C$_4$–C$_8$)-cycloalkenyl-(C$_1$–C$_4$)-alkenylsulfonyl, (C$_1$–C$_6$)-alkyl-(C$_3$–C$_8$)-cycloalkylsulfonyl, (C$_2$–C$_6$)-alkenyl-(C$_3$–C$_8$)-cycloalkylsulfonyl, (C$_2$–C$_6$)-alkyriyl-(C$_3$–C$_8$)-cycloalkylsulfonyl, (C$_1$–C$_6$)-alkyl-(C$_4$–C$_8$)-cycloalkenylsulfonyl, (C$_2$–C$_6$)-alkenyl-(C$_4$–C$_8$)-cycloalkenylsulfonyl, (C$_1$–C$_6$)-alkylamino, (C$_2$–C$_6$)-alkenylamino, (C$_2$–C$_6$)-alkynylamino, (C$_1$–C$_6$)-haloalkylamino, (C$_2$–C$_6$)-haloalkenylamino, (C$_2$–C$_6$)-haloalkynylamino, (C$_3$–C$_8$)-cycloalkylamino, (C$_4$–C$_8$)-cycloalkenylamino, (C$_3$–C$_8$)-halocycloalkamino, (C$_4$–C$_8$)-halocycloalkenylamino, (C$_3$–C$_8$)-cycloalkyl-(C$_1$–C$_4$)-alkylamino, (C$_4$–C$_8$)-cycloalkenyl-(C$_1$–C$_4$)-alkylamino, (C$_3$–C$_8$)-cycloalkyl-(C$_2$–C$_4$)-alkenylamino, (C$_4$–C$_8$)-cycloalkenyl-(C$_1$–C$_4$)-alkenylamino, (C$_1$–C$_6$)-alkyl-(C$_3$–C$_8$)-cycloalkylamino, (C$_2$–C$_6$)-alkenyl-(C$_3$–C$_8$)-cycloalkylamino, (C$_2$–C$_6$)-alkynyl-(C$_3$–C$_8$)-cycloalkylamino, (C$_1$–C$_6$)-alkyl-(C$_4$–C$_8$)-cycloalkenylamino, (C$_2$–C$_6$)-alkenyl-(C$_4$–C$_8$)-cycloalkenylamino, (C$_1$–C$_6$)-trialkylsilyl, aryl, aryloxy, arylthio, arylamino, aryl-(C$_1$–C$_4$)-alkoxy, aryl-(C$_2$–C$_4$)-alkenyloxy, aryl-(C$_1$–C$_4$)-alkylthio, aryl-(C$_2$–C$_4$)-alkenylthio, aryl-(C$_1$–C$_4$)-alkylamino, aryl-(C$_2$–C$_4$)-alkenylamino, aryl-(C$_1$–C$_6$)-dialkylsilyl, diaryl-(C$_1$–C$_6$)-alkylsilyl, triarylsilyl and 5- or 6-membered heterocyclyl, where the cyclic moiety of the fourteen last-mentioned radicals is optionally substituted by one or more radicals from the group halogen, cyano, nitro, amino, hydroxyl, thio, (C$_1$–C$_4$)-alkyl, (C$_1$–C$_4$)-haloalkyl, (C$_3$–C$_8$)-cycloalkyl, (C$_1$–C$_4$)-alkoxy, (C$_1$–C$_4$)-haloalkoxy, (C$_1$–C$_4$)-alkylthio, (C$_1$–C$_4$)-haloalkylthio, (C$_1$–C$_4$)-alkylamino, (C$_1$–C$_4$)-haloalkylamino, formyl and (C$_1$–C$_4$)-alkanoyl, aryl, 5- or 6-membered heteroaromatic, where the two last-mentioned radicals are optionally substituted by one or more radicals from the group halogen, cyano, nitro, hydroxyl, thio, amino, formyl, (C$_1$–C$_6$)-alkoxy, (C$_2$–C$_6$)-alkenyloxy, (C$_2$–C$_6$)-alkynyloxy, (C$_1$–C$_6$)-haloalkyloxy, (C$_2$–C$_6$)-haloalkenyloxy, (C$_2$–C$_6$)-haloalkynyloxy, (C$_3$–C$_8$)-cycloalkoxy, (C$_4$–C$_8$)-cycloalkenyloxy, (C$_3$–C$_8$)- halocycloalkoxy, $(C_4-C_8)$-halocycloalkenyloxy, carbamoyl, $(C_1-C_6)$-mono- or dialkylcarbamoyl, $(C_1-C_6)$-alkoxycarbonyl, $(C_1-C_6)$-alkanoyloxy, $(C_1-C_6)$-mono- or dihaloalkylcarbarnoyl, $(C_1-C_6)$-haloalkoxycarbonyl, $(C_1-C_6)$-haloalkanoyloxy, $(C_1-C_6)$-alkaneamido, $(C_1-C_6)$-haloalkaneamido, $(C_2-C_6)$-alkeneamido, $(C_1-C_6)$-alkylthio, $(C_2-C_6)$-alkenylthio, $(C_2-C_6)$-alkynylthio, $(C_1-C_6)$-haloalkylthio, $(C_2-C_6)$-haloalkenylthio, $(C_2-C_6)$-haloalkynylthio, $(C_3-C_8)$-cycloalkylthio, $(C_4-C_8)$-cycloalkenylthio, $(C_3-C_8)$-halocycloalkthio, $(C_4-C_8)$-halocycloalkenylthio, $(C_1-C_6)$-alkylsulfinyl, $(C_2-C_6)$-alkenylsulfinyl, $(C_2-C_6)$-alkynylsulfinyl, $(C_1-C_6)$-haloalkylsulfinyl, $(C_2-C_6)$-haloalkenylsulfinyl, $(C_2-C_6)$-haloalkynylsulfinyl, $(C_3-C_8)$-cycloalkylsulfinyl, $(C_4-C_8)$-cycloalkenlylsulfinyl, $(C_3-C_8)$-halocycloalksulfinyl, $(C_4-C_8)$-halocycloalkenylsulfinyl, $(C_1-C_6)$-alkylsulfonyl, $(C_2-C_6)$-alkenylsulfonyl, $(C_2-C_6)$-alkynylsulfonyl, $(C_1-C_6)$-haloalkylsulfonyl, $(C_2-C_6)$-haloalkenylsulfonyl, $(C_2-C_6)$-haloalkynylsulfonyl, $(C_3-C_8)$-cycloalkylsulfonyl, $(C_4-C_8)$-cycloalkenylsulfonyl, $(C_3-C_8)$-halocycloalksulfonyl, $(C_4-C_8)$-halocycloalkenylsulfonyl, $(C_1-C_6)$-alkylamino, $(C_2-C_6)$-alkenylamino, $(C_2-C_6)$-alkynylamino, $(C_1-C_6)$-haloalkylamino, $(C_2-C_6)$-haloalkenylamino, $(C_2-C_6)$-haloalkynylamino, $(C_3-C_8)$-cycloalkylamino, $(C_4-C_8)$-cycloalkenylamino, $(C_3-C_8)$-halocycloalkylamino and $(C_4-C_8)$-halocycloalkenylamino;

$R^{11}$ is $(C_1-C_{10})$-alkyl, haloalkyl, aryl, which is optionally substituted by one or more radicals from the group halogen, cyano, nitro, $(C_1-C_4)$-alkoxy, $(C_1-C_4)$-alkyl, amino, $(C_1-C_4)$-monoalkylamino and $(C_1-C_4)$-dialkylamino, $NR^{10}_2$, $OR^{10}$ or $SR^{10}$.

The numbers in brackets are the reference numbers from The Pesticide Manual, 11th edition, British Crop Protection Council, Farnham 1997.

The method according to the invention makes it possible to reduce the application rate of crop protection agents which act synergistically with the transgenic plants, and also to increase and widen the efficacy of the transgenic plants, and therefore offers economical and ecological advantages.

The advantages of the method are, on the one hand, synergisms with the *Bacillus thuringiensis* toxins (Bt toxins) produced in the transgenic plant and, on the other hand, for example, a reduced number of applications or a reduction of the application rates to in some instances sublethal dosages (compared to the conventional application of the individual insecticides) and an associated considerably reduced environmental burden.

In particular combinations of the abovementioned active compounds show, together with the endogenously produced Bt toxins (i.e. produced within the transgenic plants) a distinct synergistic effect on a large number of harmful organisms to be controlled.

The invention also provides the use of compounds from the abovementioned groups a–f for controlling harmful organisms in genetically modified cotton plants which contain a gene derived from *Bacillus thuringiensis* which encodes and expresses an insecticidally active protein.

For the purpose of the invention, the term "insecticidally active" includes insecticidal, nematicidal, ovicidal action, and a repellent, behavior-modifying and sterilent action.

Preferred insecticidally active compounds are the abovementioned groups (a) to (e), in particular the organophosphorus compounds, pyrethroids, carbamates, endosulfan, fipronil, abamectin, piperonyl butoxide, XDE-105 and *Bacillus thuringiensis.*

Particular preference is given to triazaphos, endosulfan, deltamethrin, fipronil, abamectin, piperonyl butoxide and *Bacillus thuringiensis.*

Preference is also given to mixtures of two or more, preferably two or three, particularly preferably two, of the insecticidally active compounds. Particular preference is given to mixtures of the abovementioned organophosphorus compounds with the abovementioned pyrethroids, for example of triazaphos with deltamethrin.

Likewise, particular preference is given to the mixtures listed below: deltamethrin and piperonyl butoxide, deltamethrin and fibronil, deltamethrin and endosulfan, deltamethrin and XDE-105, deltamethrin and chlorphenapyr, deltamethrin and *Bacillus thuringiensis*, endosulfan and amitraz, endosulfan and Bacillus thuringiensis, cyfluthrin and chlorpyriphos.

Likewise, preference is given to the 4-haloalkyl-3-heterocyclylpyridines and 4-haloalkyl-5-heterocyclylpyrimidines of group (f).

For these compounds:

The term "halogen" includes fluorine, chlorine, bromine and iodine.

The term "$(C_1-C_4)$-alkyl" is to be understood as a straight-chain or branched hydrocarbon radical having 1, 2, 3 or 4 carbon atoms, such as, for example, the methyl, ethyl, propyl, isopropyl, 1-butyl, 2-butyl, 2-methylpropyl or tert-butyl radical. Correspondingly, alkyl radicals having a greater range of carbon atoms are to be understood as straight-chain or branched saturated hydrocarbon radicals which contain a number of carbon atoms which corresponds to the range stated. Thus, the term "$(C_1-C_6)$-alkyl" includes the abovementioned alkyl radicals, and, for example, the pentyl, 2-methylbutyl, 1,1-dimethylpropyl, hexyl radical. The term "$(C_1-C_{10})$-alkyl" is to be understood as the abovementioned alkyl radicals, and, for example, the nonyl, 1-decyl or 2-decyl radical and the term "$(C_1-C_{20})$-alkyl" is to be understood as the abovementioned alkyl radicals, and, for example, the undecyl, dodecyl, pentadecyl or eicosyl radical.

"$(C_1-C_4)$-Haloalkyl" is to be understood as an alkyl group mentioned under the term "$(C_1-C_4)$-alkyl" in which one or more hydrogen atoms are replaced by the same number of identical or different halogen atoms, preferably by fluorine or chlorine, such as the trifluoromethyl, the 1-fluoroethyl, the 2,2,2-trifluoroethyl, the chloromethyl, fluoromethyl, the difluoromethyl and the 1,1,2,2-tetrafluoroethyl group.

"$(C_1-C_4)$-Alkoxy" is to be understood as an alkoxy group whose hydrocarbon radical has the meaning given under the term "(el -$C_4$)-alkyl". Alkoxy groups embracing a greater range of carbon atoms are to be understood correspondingly.

The terms "alkenyl" and "alkynyl" having a prefix stating the range of carbon atoms denote a straight-chain or branched hydrocarbon radical having a number of carbon atoms corresponding to the range stated which comprises at least one multiple bond which may be in any position of the unsaturated radical in question. "($C_2$–$C_4$)-Alkenyl" is thus, for example, the vinyl, allyl, 2-methyl-2-propene or 2-butenyl group; "($C_2$–$C_6$)-alkenyl" denotes the abovementioned radicals and, for example, the pentenyl, 2-methylpentenyl or the hexenyl group. The term "($C_2$–$C_{20}$)-alkenyl" is to be understood as the abovementioned radicals and, for example, the 2-decenyl or the 2-eicosenyl group. "($C_2$–$C_4$)-Alkynyl" is, for example, the ethynyl, propargyl, 2-methyl-2-propyne or 2-butynyl group. "($C_2$–$C_6$)-Alkynyl" is to be understood as the abovementioned radicals and, for example, the 2-pentynyl- or the 2-hexynyl group and "($C_2$–$C_{20}$)-alkynyl" is to be understood as the abovementioned radicals and, for example, the 2-octynyl or the 2-decynyl group.

"($C_3$–$C_8$)-Cycloalkyl" denotes monocyclic alkyl radicals, such as the cyclopropyl, cyclobutyl, cyclopentyl, cyclohexyl, cycloheptyl or cyclooctyl radical and bicyclic alkyl radicals, such as the norbornyl radical.

The term "($C_3$–$C_8$)-cycloalkyl-($C_1$–$C_4$)-alkyl" is to be understood as, for example, the cyclopropylmethyl, cyclopentylmethyl, cyclohexylmethyl, cyclohexylethyl and cyclohexylbutyl radical, and the term "($C_1$–$C_6$)-alkyl-($C_3$–$C_8$)-cycloalkyl is to be understood as, for example, the 1-methylcyclopropyl, 1-methylcyclopentyl, 1-methylcyclohexyl, 3-hexylcyclobutyl and 4-tert-butylcyclohexyl radical.

"($C_1$–$C_4$)-Alkoxy-($C_1$–$C_6$)-alkyloxy" is an alkoxy group as defined above which is substituted by a further alkoxy group, such as, for example, 1-ethoxyethoxy.

"($C_3$–$C_8$)-Cycloalkoxy" or "($C_3$–$C_8$)-cycloalkylthio" is to be understood as one of the abovementioned ($C_3$–$C_8$)-cycloalkyl radicals which is linked via an oxygen or sulfur atom.

"($C_3$–$C_8$)-Cycloalkyl-($C_1$–$C_6$)-alkoxy" is, for example, the cyclopropylmethoxy, cyclobutylmethoxy, cyclopentylmethoxy, cyclohexylmethoxy, cyclohexylethoxy or the cyclohexylbutoxy group;

The term "($C_1$–$C_4$)-alkyl-($C_3$–$C_8$)-cycloalkoxy" is, for example, the methylcyclopropyloxy, methylcyclobutyloxy or the butylcyclohexyloxy group.

"($C_1$–$C_6$)-Alkylthio" is an alkylthio group whose hydrocarbon radical has the meaning given under the term "($C_1$–$C_6$)-alkyl".

Correspondingly, "($C_1$–$C_6$)-alkylsulfinyl" is, for example, the methyl-, ethyl-, propyl-, isopropyl-, butyl-, isobutyl-, sec-butyl- or tert-butylsulfinyl group and "($C_1$–$C_6$)-alkylsulfonyl" is, for example, the methyl-, ethyl-, propyl-, isopropyl-, butyl-, isobutyl-, sec-butyl- or tert-butylsulfonyl group.

"($C_1$–$C_6$)-Alkylamino" is a nitrogen atom which is substituted by one or two identical or different alkyl radicals of the above definition.

The term "($C_1$–$C_6$)-mono- or dialkylcarbamoyl" is a carbamoyl group having one or two hydrocarbon radicals which have the meaning given under the term "($C_1$–$C_6$-alkyl)" and which, in the case of two hydrocarbon radicals, may be identical or different.

Correspondingly, "($C_1$–$C_6$)-dihaloalkylcarbamoyl" is a carbamoyl group which carries two ($C_1$–$C_6$)-haloalkyl radicals in accordance with the above definition or one ($C_1$–$C_6$)-haloalkyl radical and one ($C_1$–$C_6$)-alkyl radical in accordance with the above definition.

"($C_1$–$C_6$)-Alkanoyl" is, for example, the acetyl, propionyl, butyryl or 2-methylbutyryl group.

The term "aryl" is to be understood as an isocyclic aromatic radical preferably having 6 to 14, in particular 6 to 12, carbon atoms, such as, for example, phenyl, naphthyl or biphenylyl, preferably phenyl. "Aroyl" is thus an aryl radical as defined above which is attached via a carbonyl group, such as, for example, the benzoyl group.

The term "heterocyclyl" denotes a cyclic radical which may be fully saturated, partially unsaturated or fully unsaturated and which may be interrupted by at least one or more identical atoms from the group nitrogen, sulfur or oxygen, oxygen atoms, however, not being directly adjacent to one another and at least one carbon atom being present in the ring, such as, for example, a thiophene, furan, pyrrole, thiazole, oxazole, imidazole, isothiazole, isoxazole, pyrazole, 1,3,4-oxadiazole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, pyrazine, pyrimidine, pyridazine, 1,3,5-triazine, 1,2,4-triazine, 1,2,4,5-tetrazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine 4H-quinolizine; piperidine, pyrrolidine, oxazoline, tetrahydrofuran, tetrahydropyran, isoxazolidine or thiazolidine radical. The term "heteroaromatic" thus embraces, from among the meanings mentioned above under "heterocyclyl", in each case the fully unsaturated aromatic heterocyclic compounds.

"Aryl-($C_1$–$C_4$)-alkoxy" is an aryl radical which is attached via a ($C_1$–$C_4$)-alkoxy group, for example the benzyloxy, phenylethoxy, phenylbutoxy or naphthylmethoxy radical.

"Arylthio" is an aryl radical attached via a sulfur atom, for example the Ephenylthio or the 1- or 2-naphthylthio radical. Correspondingly, "aryloxy" is, for example, the phenoxy or 1- or 2-naphthyloxy radical.

"Aryl-($C_1$–$C_4$)-alkylthio" is an aryl radical which is attached via an alkylthio radical, for example the benzylthio, naphthylmethylthio or the iphenylethylthio radical.

The term "($C_1$–$C_6$)-trialkylsilyl" denotes a silicon atom which carries three identical or different alkyl radicals in accordance with the above definition. Correspondingly "aryl-($C_1$–$C_6$)-dialkylsilyl" is a silicon atom which carries one aryl radical and two identical or different radicals in accordance with the above defition, "diaryl-($C_1$–$C_6$)-alkylsilyl" is a silicon atom which carries one alkyl radical and two identical or different aryl radicals in accordance with the above definition, and "triarylsilyl" is a silicon atom which carries three identical or different aryl radicals in accordance with the above definition.

In cases where two or more radicals $R^{10}$ are present in a substituent, such as, for example, in $—C(=W)NR^{10}{}_2$. these radicals may be identical or different.

Y in the formula (I) is preferably $CF_3$. Furthermore, X is preferably the group CH. Likewise, preference is given to compounds in which:

$X_1$=0 and $X^2$=N and $X^3$=$CR^1$. Likewise, preference is given to compounds where m=0.

Particular preference is given to compounds of the formula (I) from the group (f) in which the symbols Y, X, X, $X^1$, $X^2$, $X^3$ have the preferred meanings given above, in particular to compounds in which m likewise has the preferred meaning.

Preference is given to those compounds from the group (D with the formula I in which Y is $C_1$–$C_6$-alkyl which is mono- or polysubstituted by chlorine and/or fluorine;

m is zero;

Q is a 5-membered heterocyclic group

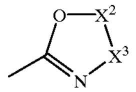

in which a) $X^2$=$NR^a$ and $X^3$=$CR^bR^1$ or b) $X^2$=$CR^aR^2$and $X^3$=$CR^bR^3$ or c) $X^2$=$CR^4R^5$ and $X^3$=$CR^6R^7$;

$R^a$ and $R^b$ together are a bond;

$R^1$, $R^2$, $R^3$, $R^4$ and $R^6$ are each independently of one another hydrogen, halogen, $C_1$–$C_{12}$-alkyl, $C_3$–$C_8$-cycloalkyl, $C_2$–$C_8$-alkenyl, $C_2$–$C_8$-alkynyl, where the four last-mentioned hydrocarbon radicals are optionally mono- or polysubstituted by identical or different radicals from a group A1 consisting of $C_1$–$C_6$-alkylcarbonyl, $C_1$–$C_6$-alkylaminocarbonyl, $C_1$–$C_6$-alkoxy, $C_1$–$C_6$-alkylthio, $C_1$–$C_6$-alkylamino, $C_1$–$C_6$-alkylcarbonylamino, $C_1$–$C_6$-alkylsulfonylamino, phenyl, furyl, pyrryl, thienyl, halogen, cyano, phenyloxy, phenylthio and phenylamino, where the eleven first-mentioned radicals of group Al are each optionally mono- or polysubstituted by identical or different radicals from a group B1 consisting of halogen, cyano, $C_1$–$C_3$-alkoxy and phenyl which is optionally mono- or polysubstituted by one or more halogen atoms and where the three last-mentioned radicals of group A1 are each optionally mono- or polysubstituted by identical or different radicals from a group B2 consisting of halogen, cyano, nitro, $C_1$–$C_3$-alkyl and $C_1$–$C_3$-alkoxy, or are $C_1$–$C_6$-alkylcarbonyl, $C_1$–$C_6$-alkylaminocarbonyl, $C_1$–$C_6$-alkoxycarbonyl, phenyl, pyridyl, furyl, thienyl, pyrryl, where the eight last-mentioned radicals are optionally mono- or polysubstituted by identical or different radicals from group B1, or are $OR^{10}$, $SR^{10}$ or $N(R^{10})_2$;

$R^5$ and $R^7$ are each independently of one another hydrogen, halogen, $C_1$–$C_{12}$-alkyl, $C_3$–$C_8$-cycloalkyl, $C_2$–$C_8$-alkenyl, $C_2$–$C_8$-alkynyl, where the four last-mentioned hydrocarbon radicals are optionally mono- or polysubstituted by identical or different radicals from a group A2 consisting of $C_1$–$C_6$-alkylcarbonyl, $C_1$–$C_6$-alkylaminocarbonyl, $C_1$–$C_6$-alkoxy, $C_1$–$C_6$-alkylthio, $C_1$–$C_6$-alkylamino, $C_1$–$C_6$-alkylcarbonylamino, phenyl, furyl, pyrryl, thienyl, halogen, cyano, phenyloxy, phenylthio and phenylamino, where the ten first-mentioned radicals of group A2 are each optionally mono- or polysubstituted by identical or different radicals from the group B1 and the three last-mentioned radicals of group A2 are each optionally mono- or polysubstituted by identical or different radicals from the group B2, or are $C_1$–$C_6$-alkylcarbonyl, $C_1$–$C_6$-alkylaminocarbonyl, $C_1$–$C_6$-alkoxycarbonyl, phenyl, pyridyl, furyl, thienyl, pyrryl, where the eight last-mentioned radicals are optionally mono- or polysubstituted by identical or different radicals from the group B1, or are $OR^{10}$, $SR^{10}$ or $N(R^{10})_2$;

$R^{10}$ is hydrogen, benzyl, $C_1$–$C_6$-alkyl, $C_1$–$C_6$-cycloalkyl, $C_2$–$C_6$-alkenyl, $C_2$–$C_6$-alkynyl, phenyl, $C_1$–$C_6$-alkylcarbonyl or $C_1$–$C_6$-alkylsulfonyl, where the eight last-mentioned radicals are optionally mono- or polysubstituted by identical or different halogen atoms.

Particular preference is given to compounds from the group (f) with the formula I in which Y is trifluoromethyl;

$R^1$, $R^2$, $R^3$ $R^4$ and $R^6$ are each independently of one another halogen, $C_1$–$C_{12}$-alkyl, $C_2$–$C_{12}$-alkenyl, where the two last-mentioned radicals are optionally mono- or polysubstituted by identical or different radicals from a group A3 consisting of $C_1$–$C_4$-alkylcarbonyl, $C_1$–$C_4$-alkylaminocarbonyl, $C_1$–$C_4$-alkoxy, $C_1$–$C_4$-alkylthio, $C_1$–$C_4$-alkylamino, $C_1$–$C_4$-alkylcarbonylamino, $C_1$–$C_4$-alkylsulfonylamino, phenyl, furyl, pyrryl, thienyl, fluorine, chlorine, bromine, cyano, phenyloxy, phenylthio and phenylamino, where the eleven first-mentioned radicals of group A3 are each optionally mono- or polysubstituted by identical or different radicals from the group B1 and the three last-mentioned radicals of group A3 are each optionally mono- or polysubstituted by identical or different radicals from the group B2, or are $OR^{10}$, $SR^{10}$ or $N(R^{10})_2$;

$R^5$ and $R^7$ are each independently of one another halogen, $C_1$–$C_{12}$-alkyl, $C_2$–$C_{12}$-alkenyl, where the two last-mentioned radicals are optionally mono- or polysubstituted by identical or different radicals from a group A4 consisting of $C_1$–$C_4$-alkylcarbonyl, $C_1$–$C_4$-alkylaminocarbonyl, $C_1$–$C_4$-alkoxy, $C_1$–$C_4$-alkylthio, $C_1$–$C_4$-alkylamino, $C_1$–$C_4$-alkylcarbonylamino, phenyl, furyl, pyrryl, thienyl, fluorine, chlorine, bromine, cyano, phenyloxy, phenylthio and phenylamino, where the ten first-mentioned radicals of group A4 are each optionally mono- or polysubstituted by identical or different radicals from the group B1 and the three last-mentioned radicals of group A4 are each optionally mono- or polysubstituted by identical or different radicals from the group B2, or are $OR^{10}$, $SR^{10}$ or $N(R^{10})_2$;

$R^{10}$ is hydrogen, $C_1$–$C_6$-alkyl, $C_2$–$C_6$-alkenyl, $C_2$–$C_6$-alkynyl, phenyl, $C_1$–$C_4$-alkylcarbonyl or $C_1$–$C_4$-alkylsulfonyl, where the six last-mentioned radicals are optionally mono- or polysubstituted by identical or different halogen atoms.

Very particular preference is given to compounds from the group (f) with the formula I in which $R^1$, $R^2$, $R^3$, $R^4$ and $R^6$ are each independently of one another $C_1$–$C_{10}$-alkyl, $C_2$–$C_{10}$-alkenyl, where the two last-mentioned radicals are optionally mono- or polysubstituted by identical or different radicals from a group A5 consisting of $C_1$–$C_4$-alkylcarbonyl, $C_1$–$C_4$-alkylaminocarbonyl, $C_1$–$C_4$-alkoxy, $C_1$–$C_4$-alkylthio, $C_1$–$C_4$-alkylamino, $C_1$–$C_4$-alkylcarbonylamino, $C_1$–$C_4$-alkylsulfonylamino, phenyl, fluorine, chlorine, bromine, cyano, phenyloxy, phenylthio and phenylamino, where the eight first-mentioned radicals of group A5 are each optionally mono- or polysubstituted by identical or different radicals from the group B1 and the three last-mentioned radicals of group A5 are each optionally mono- or polysubstituted by identical or different radicals from the group B2;

$R^5$ and $R^7$ are each independently of one another $C_1$–$C_{10}$-alkyl, $C_2$–$C_{10}$-alkenyl, where the two last-mentioned radicals are optionally mono- or polysubstituted by identical or different radicals from a group A6 consisting of $C_1$–$C_4$-alkylcarbonyl, $C_1$–$C_4$-alkylaminocarbonyl, $C_1$–$C_4$-alkoxy, $C_1$–$C_4$-alkylthio, $C_1$–$C_4$-alkylamino, $C_1$–$C_4$-alkylcarbonylamino, phenyl, fluorine, chlorine, bromine, cyano, phenyloxy, phenylthio and phenylamino, where the seven first-mentioned radicals of group A6 are each optionally mono- or polysubstituted by identical or different radicals from the group B1 and the three last-mentioned radicals of group A6 are each optionally mono- or polysubstituted by identical or different radicals from the group B2.

Particularly preferred compounds from the group (f) with the formula (I) are listed in the following Tables 1 to 5:

TABLE 1

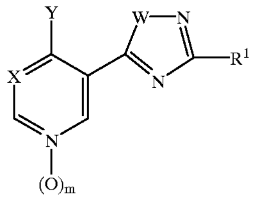

| No. | X | Y | m | W | $R^1$ | m.p. [° C.] |
|---|---|---|---|---|---|---|
| 1 | N | $CCl_3$ | 0 | O | $CH_3$ | |
| 2 | N | $CCl_3$ | 0 | O | $CH_2CH_3$ | |
| 3 | N | $CCl_3$ | 0 | O | $COOCH_2CH_3$ | |
| 4 | CH | $CCl_3$ | 0 | O | $CH_3$ | |
| 5 | CH | $CCl_3$ | 0 | O | $COOCH_2CH_3$ | |
| 6 | N | $(CF_2)_3CHF_2$ | 0 | O | $CH_3$ | |
| 7 | N | $(CF_2)_3CHF_2$ | 0 | O | $COOCH_2CH_3$ | |
| 8 | CH | $(CF_2)_3CHF_2$ | 0 | O | $CH_3$ | |
| 9 | CH | $(CF_2)_3CHF_2$ | 0 | O | $COOCH_2CH_3$ | |
| 10 | N | $(CF_2)_3CHF_2$ | 0 | S | $CH_2COOC(CH_3)_3$ | |
| 11 | N | $(CF_2)_3CHF_2$ | 0 | S | $CH_2CONHCH_3$ | |
| 12 | CH | $(CF_2)_3CHF_2$ | 0 | S | $(CH_2)_2CH_3$ | |
| 13 | CH | $(CF_2)_3CHF_2$ | 0 | S | $COOCH_2CH_3$ | |
| 14 | N | $(CF_2)_2CHF_2$ | 0 | O | $CH_2CH_3$ | |
| 15 | N | $(CF_2)_2CHF_2$ | 0 | O | $COOCH_2CH_3$ | |
| 16 | N | $(CF_2)_2CHF_2$ | 0 | O | OH | |
| 17 | N | $(CF_2)_2CHF_2$ | 0 | O | $OCH_3$ | |
| 18 | CH | $(CF_2)_2CHF_2$ | 0 | O | $CH_3$ | |
| 19 | CH | $(CF_2)_2CHF_2$ | 0 | O | $COOCH_2CH_3$ | |
| 20 | CH | $(CF_2)_2CHF_2$ | 0 | O | OH | |
| 21 | CH | $(CF_2)_2CHF_2$ | 0 | O | $NHCH_3$ | |
| 22 | N | $CF_2CF_3$ | 0 | O | $CH_3$ | |
| 23 | N | $CF_2CF_3$ | 0 | O | $CH_2CH_3$ | |
| 24 | N | $CF_2CF_3$ | 0 | O | $(CH_2)_2CH_3$ | |
| 25 | N | $CF_2CF_3$ | 0 | O | $CH(CH_3)_2$ | |
| 26 | N | $CF_2CF_3$ | 0 | O | Cyclo-$C_6H_{11}$ | |
| 27 | N | $CF_2CF_3$ | 0 | O | $CH_2C{=}CH_2$ | |
| 28 | N | $CF_2CF_3$ | 0 | O | $CH_2C{\equiv}CH$ | |
| 29 | N | $CF_2CF_3$ | 0 | O | $CH_2CH_2C{\equiv}CH$ | |
| 30 | N | $CF_2CF_3$ | 0 | O | $CH_2C{\equiv}CCH_2CH_3$ | |
| 31 | N | $CF_2CF_3$ | 0 | O | $(CH_2)_4C{\equiv}CH$ | |
| 32 | N | $CF_2CF_3$ | 0 | O | $CHFCF_3$ | |
| 33 | N | $CF_2CF_3$ | 0 | O | $COOCH_2CH_3$ | |
| 34 | N | $CF_2CF_3$ | 0 | O | $CH_2COOC(CH_3)_3$ | |
| 35 | N | $CF_2CF_3$ | 0 | O | $CH_2CONHCH_3$ | |
| 36 | N | $CF_2CF_3$ | 0 | O | $NH_2$ | |
| 37 | N | $CF_2CF_3$ | 0 | O | $NHCH_2CH_3$ | |
| 38 | CH | $CF_2CF_3$ | 0 | O | $CH_3$ | |
| 39 | CH | $CF_2CF_3$ | 0 | O | $CH_2CH_3$ | |
| 40 | CH | $CF_2CF_3$ | 0 | O | $(CH_2)_2CH_3$ | |
| 41 | CH | $CF_2CF_3$ | 0 | O | $CH(CH_3)_2$ | |
| 42 | CH | $CF_2CF_3$ | 0 | O | Cyclo-$C_6H_{11}$ | |
| 43 | CH | $CF_2CF_3$ | 0 | O | $CH_2C{=}CH_2$ | |
| 44 | CH | $CF_2CF_3$ | 0 | O | $CH_2COOC(CH_3)_3$ | |
| 45 | CH | $CF_2CF_3$ | 0 | O | $NH_2$ | |
| 46 | CH | $CF_2CF_3$ | 0 | O | $NHCOCH_3$ | |
| 47 | CH | $CF_2CF_3$ | 0 | O | $NHCOCH_2CH_3$ | |
| 48 | N | $CF_2CF_3$ | 0 | S | $CH_3$ | |
| 49 | N | $CF_2CF_3$ | 0 | S | $CH_2CH_3$ | |
| 50 | N | $CF_2CF_3$ | 0 | S | $(CH_2)_2CH_3$ | |
| 51 | N | $CF_2Cl$ | 0 | O | $CH_3$ | |
| 52 | N | $CF_2Cl$ | 0 | O | $CH_2CH_3$ | |
| 53 | N | $CF_2Cl$ | 0 | O | $(CH_2)_2CH_3$ | |
| 54 | N | $CF_2Cl$ | 0 | O | $CH(CH_3)_2$ | |
| 55 | N | $CF_2Cl$ | 0 | O | $CH_2COOC(CH_3)_3$ | |
| 56 | N | $CF_2Cl$ | 0 | O | $CH_2CONHCH_3$ | |
| 57 | N | $CF_2Cl$ | 0 | O | OH | |
| 58 | N | $CF_2Cl$ | 0 | O | $OCH_3$ | |

TABLE 1-continued

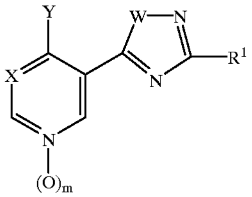

| No. | X | Y | m | W | $R^1$ | m.p. [° C.] |
|---|---|---|---|---|---|---|
| 59 | N | $CF_2Cl$ | 0 | O | $OCH_2CH_3$ | |
| 60 | N | $CF_2Cl$ | 0 | O | $NHCH_3$ | |
| 61 | CH | $CF_2Cl$ | 0 | O | $CH_3$ | |
| 62 | CH | $CF_2Cl$ | 0 | O | $CH_2CH_3$ | |
| 63 | CH | $CF_2Cl$ | 0 | O | $(CH_2)_2CH_3$ | |
| 64 | CH | $CF_2Cl$ | 0 | O | $CH(CH_3)_2$ | |
| 65 | CH | $CF_2Cl$ | 0 | O | $CH_2COOC(CH_3)_3$ | |
| 66 | CH | $CF_2Cl$ | 0 | O | $CH_2CONHCH_3$ | |
| 67 | CH | $CF_2Cl$ | 0 | O | OH | |
| 68 | CH | $CF_2Cl$ | 0 | O | $OCH_3$ | |
| 69 | CH | $CF_2Cl$ | 0 | O | $OCH_2CH_3$ | |
| 70 | CH | $CF_2Cl$ | 0 | O | $NHCH_3$ | |
| 71 | CH | $CF_2Cl$ | 0 | O | Cyclo-$C_6H_{11}$ | |
| 72 | CH | $CF_2Cl$ | 0 | O | $CH_2C{=}CH_2$ | |
| 73 | CH | $CF_2Cl$ | 0 | O | $COOCH_2CH_3$ | |
| 74 | CH | $CF_2Cl$ | 0 | O | $CH_2COOC(CH_3)_3$ | |
| 75 | CH | $CF_2Cl$ | 0 | O | $CH_2CONHCH_3$ | |
| 76 | CH | $CF_2Cl$ | 0 | O | $OCH_3$ | |
| 77 | CH | $CF_2Cl$ | 0 | O | $NHCH_3$ | |
| 78 | CH | $CF_3$ | 0 | O | $CH_3$ | oil |
| 79 | CH | $CF_3$ | 0 | O | $CH_2CH_3$ | oil |
| 80 | CH | $CF_3$ | 0 | O | $(CH_2)_2CH_3$ | oil |
| 81 | CH | $CF_3$ | 0 | O | $CH(CH_3)_2$ | oil |
| 82 | CH | $CF_3$ | 0 | O | Cyclo-$C_3H_5$ | oil |
| 83 | CH | $CF_3$ | 0 | O | $(CH_2)_3CH_3$ | oil |
| 84 | CH | $CF_3$ | 0 | O | $CH(CH_3)CH_2CH_3$ | oil |
| 85 | CH | $CF_3$ | 0 | O | $CH_2CH(CH_3)_2$ | oil |
| 86 | CH | $CF_3$ | 0 | O | $C(CH_3)_3$ | oil |
| 87 | CH | $CF_3$ | 0 | O | Cyclo-$C_4H_7$ | |
| 88 | CH | $CF_3$ | 0 | O | $(CH_2)_4CH_3$ | oil |
| 89 | CH | $CF_3$ | 0 | O | $CH(CH_3)(CH_2)_2CH_3$ | |
| 90 | CH | $CF_3$ | 0 | O | $(CH_2)_2CH(CH_3)_2$ | |
| 91 | CH | $CF_3$ | 0 | O | $CH_2C(CH_3)_3$ | |
| 92 | CH | $CF_3$ | 0 | O | Cyclo-$C_5H_9$ | oil |
| 93 | CH | $CF_3$ | 0 | O | $(CH_2)_5CH_3$ | |
| 94 | CH | $CF_3$ | 0 | O | $C(CH_2CH_3)_2CH_3$ | |
| 95 | CH | $CF_3$ | 0 | O | Cyclo-$C_6H_{11}$ | |
| 96 | CH | $CF_3$ | 0 | O | $(CH_2)_6CH_3$ | |
| 97 | CH | $CF_3$ | 0 | O | $CH(CH_3)(CH_2)_4CH_3$ | |
| 98 | CH | $CF_3$ | 0 | O | Cyclo-$C_7H_{13}$ | |
| 99 | CH | $CF_3$ | 0 | O | $CH_2$-cyclo-$C_6H_{11}$ | |
| 100 | CH | $CF_3$ | 0 | O | 2-Norbornyl | |
| 101 | CH | $CF_3$ | 0 | O | $(CH_2)_7CH_3$ | |
| 102 | CH | $CF_3$ | 0 | O | $CH(CH_2CH_3)(CH_2)_5CH_3$ | |
| 103 | CH | $CF_3$ | 0 | O | $(CH_2)_8CH_3$ | |
| 104 | CH | $CF_3$ | 0 | O | $(CH_2)_3$-cyclo-$C_6H_{11}$ | |
| 105 | CH | $CF_3$ | 0 | O | $(CH_2)_9CH_3$ | |
| 106 | CH | $CF_3$ | 0 | O | 1-Adamantyl | |
| 107 | CH | $CF_3$ | 0 | O | $(CH_2)_{10}CH_3$ | |
| 108 | CH | $CF_3$ | 0 | O | $(CH_2)_{11}CH_3$ | |
| 109 | CH | $CF_3$ | 0 | O | $CH(CH_3)(CH_2)_9CH_3$ | |
| 110 | CH | $CF_3$ | 0 | O | $(CH_2)_{12}CH_3$ | |
| 111 | CH | $CF_3$ | 0 | O | $(CH_2)_{13}CH_3$ | |
| 112 | CH | $CF_3$ | 0 | O | $(CH_2)_{14}CH_3$ | |
| 113 | CH | $CF_3$ | 0 | O | $(CH_2)_{15}CH_3$ | |
| 114 | CH | $CF_3$ | 0 | O | $(CH_2)_{17}CH_3$ | |
| 115 | CH | $CF_3$ | 0 | O | $(CH_2)_{19}CH_3$ | |
| 116 | CH | $CF_3$ | 0 | O | CHO | |
| 117 | CH | $CF_3$ | 0 | O | $CH{=}CH_2$ | oil |
| 118 | CH | $CF_3$ | 0 | O | $CH_2C{=}C(CH_3)_2$ | |
| 119 | CH | $CF_3$ | 0 | O | $CH_2CH_2C{=}CH_2$ | |
| 120 | CH | $CF_3$ | 0 | O | $CH_2C{=}CH_2$ | |
| 121 | CH | $CF_3$ | 0 | O | $C(CH_3){=}CH_2$ | |
| 122 | CH | $CF_3$ | 0 | O | (E)-$CH_2CH{=}CHCH_2CH_3$ | |
| 123 | CH | $CF_3$ | 0 | O | (Z)-$CH_2CH{=}CHCH_2CH_3$ | |
| 124 | CH | $CF_3$ | 0 | O | $(CH_2)_5C{=}CH_2$ | |

TABLE 1-continued

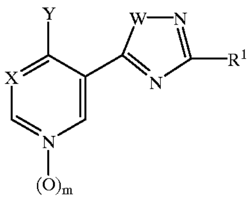

| No. | X | Y | m | W | $R^1$ | m.p. [° C.] |
|---|---|---|---|---|---|---|
| 125 | CH | $CF_3$ | 0 | O | $C(=CHCH_3)CH_3$ | 62–64 |
| 126 | CH | $CF_3$ | 0 | O | Geranyl | |
| 127 | CH | $CF_3$ | 0 | O | 3-Menthyl | |
| 128 | CH | $CF_3$ | 0 | O | $C\equiv CH$ | |
| 129 | CH | $CF_3$ | 0 | O | $CH_2C\equiv CH$ | |
| 130 | CH | $CF_3$ | 0 | O | $CH_2CH_2C\equiv CH$ | |
| 131 | CH | $CF_3$ | 0 | O | $CH_2CH_2C\equiv CH$ | |
| 132 | CH | $CF_3$ | 0 | O | $(CH_2)_4C\equiv CH$ | |
| 133 | CH | $CF_3$ | 0 | O | $CHFCF_3$ | oil |
| 134 | CH | $CF_3$ | 0 | O | $COOCH_2CH_3$ | oil |
| 135 | CH | $CF_3$ | 0 | O | $CH_2CH_2OH$ | oil |
| 136 | CH | $CF_3$ | 0 | O | $CH_2CH_2OCH_3$ | oil |
| 137 | CH | $CF_3$ | 0 | O | $CH_2COOC(CH_3)_3$ | oil |
| 138 | CH | $CF_3$ | 0 | O | $CH_2SC_6H_5$ | oil |
| 139 | CH | $CF_3$ | 0 | O | $CH_2CONHCH_3$ | 109–111 |
| 140 | CH | $CF_3$ | 0 | O | $CH_2CH(OH)CH_2OH$ | |
| 141 | CH | $CF_3$ | 0 | O | $CH_2COCH_3$ | |
| 142 | CH | $CF_3$ | 0 | O | $COCH_3$ | |
| 143 | CH | $CF_3$ | 0 | O | $CH_2OC_6H_5$ | |
| 144 | CH | $CF_3$ | 0 | O | $COC_6H_5$ | |
| 145 | CH | $CF_3$ | 0 | O | $CO(4\text{-}Cl)—C_6H_4$ | |
| 146 | CH | $CF_3$ | 0 | O | $CF_2CH_3$ | |
| 147 | CH | $CF_3$ | 0 | O | $CH_2CN$ | |
| 148 | CH | $CF_3$ | 0 | O | $CH_2CH_2CN$ | |
| 149 | CH | $CF_3$ | 0 | O | $CH_2CH(—O—)CH_2$ | |
| 150 | CH | $CF_3$ | 0 | O | $CH_2(4\text{-}OCH_3)C_6H_5$ | |
| 151 | CH | $CF_3$ | 0 | O | $CH_2$-cyclo-(4-Oxo)—$C_6H_8$ | |
| 152 | CH | $CF_3$ | 0 | O | $CH_2CH(OH)CH_2SC_6H_5$ | |
| 153 | CH | $CF_3$ | 0 | O | $CH_2CH_2Si(CH_3)_3$ | |
| 154 | CH | $CF_3$ | 0 | O | $CH=CF_2$ | |
| 155 | CH | $CF_3$ | 0 | O | $CCl=CHCl$ | |
| 156 | CH | $CF_3$ | 0 | O | 2-Pyridyl | 99–101 |
| 157 | CH | $CF_3$ | 0 | O | 2-Furyl | |
| 158 | CH | $CF_3$ | 0 | O | 2-Thienyl | 106–108 |
| 159 | CH | $CF_3$ | 0 | O | $CH_2C\equiv CCH_2CH_2OTHP$ | |
| 160 | CH | $CF_3$ | 0 | O | $CH_2CH_2Cl$ | oil |
| 161 | CH | $CF_3$ | 0 | O | $Si(CH_3)_3$ | |
| 162 | CH | $CF_3$ | 0 | O | $OC_6H_5$ | |
| 163 | CH | $CF_3$ | 0 | O | OH | |
| 164 | CH | $CF_3$ | 0 | O | $OCH_3$ | |
| 165 | CH | $CF_3$ | 0 | O | $OCH_2CH_3$ | |
| 166 | CH | $CF_3$ | 0 | O | $OCHF_2$ | |
| 167 | CH | $CF_3$ | 0 | O | $OCH_2C_6H_5$ | |
| 168 | CH | $CF_3$ | 0 | O | $CH_2SCH_3$ | 48–49 |
| 169 | CH | $CF_3$ | 0 | O | $SC_6H_5$ | |
| 170 | CH | $CF_3$ | 0 | O | $SeC_6H_5$ | |
| 171 | CH | $CF_3$ | 0 | O | $NH_2$ | 116–118 |
| 172 | CH | $CF_3$ | 0 | O | $NHCH_3$ | |
| 173 | CH | $CF_3$ | 0 | O | $NHCH_2CH_3$ | |
| 174 | CH | $CF_3$ | 0 | O | $N(CH_2CH_3)_2$ | |
| 175 | CH | $CF_3$ | 0 | O | $CONHCH_2C=CH_2$ | 105–107 |
| 176 | CH | $CF_3$ | 0 | O | Cl | |
| 177 | CH | $CF_3$ | 0 | O | Br | |
| 178 | CH | $CF_3$ | 0 | O | $CONH_2$ | 206–208 |
| 179 | CH | $CF_3$ | 0 | O | $NHCOCH_3$ | 129–131 |
| 180 | CH | $CF_3$ | 0 | O | $NHCOCH_2CH_3$ | |
| 181 | CH | $CF_3$ | 0 | O | $OSO_2CH_3$ | |
| 182 | CH | $CF_3$ | 0 | O | $SOCH_2(4\text{-}Br)—C_6H_4$ | |
| 183 | CH | $CF_3$ | 0 | O | $N(CH_3)COOCH_2C_6H_5$ | |
| 184 | CH | $CF_3$ | 0 | O | $NHNH_2$ | |
| 185 | CH | $CF_3$ | 0 | O | $NHN(CH_3)_2$ | |
| 186 | N | $CF_3$ | 0 | O | $CH_3$ | |
| 187 | N | $CF_3$ | 0 | O | $CH_2CH_3$ | oil |
| 188 | N | $CF_3$ | 0 | O | $(CH_2)_2CH_3$ | oil |
| 189 | N | $CF_3$ | 0 | O | $CH(CH_3)_2$ | oil |
| 190 | N | $CF_3$ | 0 | O | $(CH_2)_3CH_3$ | oil |

TABLE 1-continued

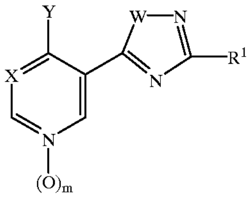

| No. | X | Y | m | W | $R^1$ | m.p. [° C.] |
|---|---|---|---|---|---|---|
| 191 | N | $CF_3$ | 0 | O | $CH_2CH(CH_3)_2$ | oil |
| 192 | N | $CF_3$ | 0 | O | $C(CH_3)_3$ | |
| 193 | N | $CF_3$ | 0 | O | $(CH_2)_4CH_3$ | oil |
| 194 | N | $CF_3$ | 0 | O | $CH(CH_3)(CH_2)_2CH_3$ | |
| 195 | N | $CF_3$ | 0 | O | $CH_2C(CH_3)_3$ | |
| 196 | N | $CF_3$ | 0 | O | Cyclo-$C_5H_9$ | |
| 197 | N | $CF_3$ | 0 | O | $(CH_2)_5CH_3$ | |
| 198 | N | $CF_3$ | 0 | O | Cyclo-$C_6H_{11}$ | |
| 199 | N | $CF_3$ | 0 | O | $CH(CH_3)(CH_2)_4CH_3$ | |
| 200 | N | $CF_3$ | 0 | O | $CH_2$-cyclo-$C_6H_{11}$ | |
| 201 | N | $CF_3$ | 0 | O | $(CH_2)_7CH_3$ | |
| 202 | N | $CF_3$ | 0 | O | $(CH_2)_8CH_3$ | |
| 203 | N | $CF_3$ | 0 | O | $(CH_2)_9CH_3$ | |
| 204 | N | $CF_3$ | 0 | O | $CH(CH_3)(CH_2)_9CH_3$ | |
| 205 | N | $CF_3$ | 0 | O | $(CH_2)_{15}CH_3$ | |
| 206 | N | $CF_3$ | 0 | O | $(CH_2)_{17}CH_3$ | |
| 207 | N | $CF_3$ | 0 | O | $(CH_2)_{19}CH_3$ | |
| 208 | N | $CF_3$ | 0 | O | $CH_2CH{=}C(CH_3)_2$ | |
| 209 | N | $CF_3$ | 0 | O | $CH_2CH_2CH{=}CH_2$ | |
| 210 | N | $CF_3$ | 0 | O | $CH_2CH{=}CH_2$ | |
| 211 | N | $CF_3$ | 0 | O | (Z)-$CH_2CH{=}CHCH_2CH_3$ | |
| 212 | N | $CF_3$ | 0 | O | $(CH_2)_5CH{=}CH_2$ | |
| 213 | N | $CF_3$ | 0 | O | $CH_2C{\equiv}CH$ | |
| 214 | N | $CF_3$ | 0 | O | $CH_2C{\equiv}CCH_2CH_3$ | |
| 215 | N | $CF_3$ | 0 | O | $CHFCF_3$ | |
| 216 | N | $CF_3$ | 0 | O | $COOCH_2CH_3$ | |
| 217 | N | $CF_3$ | 0 | O | $CH_2CH_2OH$ | |
| 218 | N | $CF_3$ | 0 | O | $CH_2CH_2OCH_3$ | |
| 219 | N | $CF_3$ | 0 | O | $CH_2COOC(CH_3)_3$ | |
| 220 | N | $CF_3$ | 0 | O | $CH_2SC_6H_5$ | |
| 221 | N | $CF_3$ | 0 | O | $CH_2CONHCH_3$ | |
| 222 | N | $CF_3$ | 0 | O | $CH_2CH(OH)CH_2OH$ | |
| 223 | N | $CF_3$ | 0 | O | CHO | |
| 224 | N | $CF_3$ | 0 | O | $COCH_3$ | |
| 225 | N | $CF_3$ | 0 | O | $CH_2OC_6H_5$ | |
| 226 | N | $CF_3$ | 0 | O | $COC_6H_5$ | |
| 227 | N | $CF_3$ | 0 | O | $CF_2CH_3$ | |
| 228 | N | $CF_3$ | 0 | O | $CH_2CN$ | |
| 229 | N | $CF_3$ | 0 | O | $CH_2CH_2CN$ | |
| 230 | N | $CF_3$ | 0 | O | $CH{=}CF_2$ | |
| 231 | N | $CF_3$ | 0 | O | 2-Furyl | |
| 232 | N | $CF_3$ | 0 | O | $CH_2C{\equiv}C{-}I$ | |
| 233 | N | $CF_3$ | 0 | O | OH | |
| 234 | N | $CF_3$ | 0 | O | $OCH_3$ | |
| 235 | N | $CF_3$ | 0 | O | $OCH_2CH_3$ | |
| 236 | N | $CF_3$ | 0 | O | $OCHF_2$ | |
| 237 | N | $CF_3$ | 0 | O | $OCH_2C_6H_5$ | |
| 238 | N | $CF_3$ | 0 | O | $SC_6H_5$ | |
| 239 | N | $CF_3$ | 0 | O | $NH_2$ | |
| 240 | N | $CF_3$ | 0 | O | $NHCH_3$ | |
| 241 | N | $CF_3$ | 0 | O | $NHCH_2CH_3$ | |
| 242 | N | $CF_3$ | 0 | O | $N(CH_2CH_3)_2$ | |
| 243 | N | $CF_3$ | 0 | O | $N(CH_2CN)_2$ | |
| 244 | N | $CF_3$ | 0 | O | $N(CH_3)_2$ | |
| 245 | N | $CF_3$ | 0 | O | $NHCOCH_3$ | |
| 246 | N | $CF_3$ | 0 | O | $NHCOCH_2CH_3$ | |
| 247 | N | $CF_3$ | 0 | O | $OSO_2CH_3$ | |
| 248 | N | $CF_3$ | 0 | O | $NHNH_2$ | |
| 249 | CH | $CF_3$ | 0 | S | $CH_3$ | |
| 250 | CH | $CF_3$ | 0 | S | $CH_2CH_3$ | |
| 251 | CH | $CF_3$ | 0 | S | $(CH_2)_2CH_3$ | |
| 252 | CH | $CF_3$ | 0 | S | CHO | |
| 253 | CH | $CF_3$ | 0 | S | $CHFCF_3$ | |
| 254 | CH | $CF_3$ | 0 | S | $CH_2C{\equiv}CH$ | |
| 255 | CH | $CF_3$ | 0 | S | $COOCH_2CH_3$ | |
| 256 | CH | $CF_3$ | 0 | S | $CH_2COOC(CH_3)_3$ | |

TABLE 1-continued

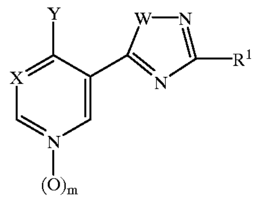

| No. | X | Y | m | W | $R^1$ | m.p. [° C.] |
|---|---|---|---|---|---|---|
| 257 | CH | $CF_3$ | 0 | S | $CH_2CN$ | |
| 258 | CH | $CF_3$ | 0 | S | $SeC_6H_5$ | |
| 259 | N | $CF_3$ | 0 | S | $CH_3$ | |
| 260 | N | $CF_3$ | 0 | S | $CH_2CH_3$ | |
| 261 | N | $CF_3$ | 0 | S | $(CH_2)_2CH_3$ | |
| 262 | N | $CF_3$ | 0 | S | $CHFCF_3$ | |
| 263 | N | $CF_3$ | 0 | S | $CH_2CH_2OH$ | |
| 264 | N | $CF_3$ | 0 | S | $CH_2COOC(CH_3)_3$ | |
| 265 | CH | $CH_2CH_2Cl$ | 0 | O | $CH_3$ | |
| 266 | CH | $CH_2CH_2Cl$ | 0 | O | $CH_2CH_3$ | |
| 267 | CH | $CH_2CH_2Cl$ | 0 | O | $(CH_2)_2CH_3$ | |
| 268 | CH | $CH_2CH_2Cl$ | 0 | O | $CH(CH_3)_2$ | |
| 269 | CH | $CH_2CH_2Cl$ | 0 | O | $CH_2SC_6H_5$ | |
| 270 | CH | $CH_2CH_2Cl$ | 0 | O | $CH_2CONHCH_3$ | |
| 271 | CH | $CH_2CH_2Cl$ | 0 | O | $NH_2$ | |
| 272 | CH | $CH_2CH_2Cl$ | 0 | O | $NHCH_2CH_3$ | |
| 273 | N | $CH_2CH_2Cl$ | 0 | O | $CH_2CH_3$ | |
| 274 | N | $CH_2CH_2Cl$ | 0 | O | $NH_2$ | |
| 275 | N | $CH_2Cl$ | 0 | O | $CH_3$ | |
| 276 | CH | $CH_2Cl$ | 0 | O | $CH_3$ | |
| 277 | CH | $CHF_2$ | 0 | O | $CH_3$ | |
| 278 | CH | $CHF_2$ | 0 | O | $CH_2CH_3$ | |
| 279 | CH | $CHF_2$ | 0 | O | $(CH_2)_2CH_3$ | |
| 280 | CH | $CHF_2$ | 0 | O | $CH_2CH{=}CH_2$ | |
| 281 | CH | $CHF_2$ | 0 | O | $C(CH_3){=}CH_2$ | |
| 282 | CH | $CHF_2$ | 0 | O | $COOCH_2CH_3$ | |
| 283 | CH | $CHF_2$ | 0 | O | $CH_2CONHCH_3$ | |
| 284 | CH | $CHF_2$ | 0 | O | $CF_2CH_3$ | |
| 285 | CH | $CHF_2$ | 0 | O | CHO | |
| 286 | CH | $CHF_2$ | 0 | O | $NH_2$ | |
| 287 | CH | $CHF_2$ | 0 | O | Cl | |
| 288 | CH | $CHF_2$ | 0 | O | $NHCOCH_3$ | |
| 289 | CH | $CHF_2$ | 0 | O | $NHNH_2$ | |
| 290 | N | $CHF_2$ | 0 | O | $CH_3$ | |
| 291 | N | $CHF_2$ | 0 | O | $CH_2CH_3$ | |
| 292 | N | $CHF_2$ | 0 | O | $CH(CH_3)(CH_2)_4CH_3$ | |
| 293 | N | $CHF_2$ | 0 | O | $CH_2CH{=}CH_2$ | |
| 294 | N | $CHF_2$ | 0 | O | $COOCH_2CH_3$ | |
| 295 | N | $CHF_2$ | 0 | O | $NH_2$ | |
| 296 | CH | $CF_3$ | 1 | O | $CH_3$ | |
| 297 | CH | $CF_3$ | 1 | O | $COOCH_2CH_3$ | |
| 298 | CH | $CF_3$ | 1 | O | $CH_2COOC(CH_3)_3$ | |
| 299 | CH | $CF_3$ | 1 | O | $CHFCF_3$ | |
| 300 | N | $CF_3$ | 0 | O | $CH_2NHSO_2CH_3$ | |
| 301 | N | $CF_3$ | 0 | O | $(CH_2)_2NHSO_2CH_3$ | |
| 302 | N | $CF_3$ | 0 | O | $CH_2NHSO_2CH_2CH_3$ | |
| 303 | N | $CF_3$ | 0 | O | $CH_2NHSO_2CH_2C_6H_5$ | |
| 304 | CH | $CF_3$ | 0 | O | $(CH_2)_4NHSO_2CF_3$ | |
| 305 | CH | $CF_3$ | 0 | O | $(CH_2)_2S(CH_2)_2CH_3$ | |
| 306 | CH | $CF_3$ | 0 | O | $(CH_2)_4S(CH_2)_4OCH_3$ | |
| 307 | CH | $CF_3$ | 0 | S | $(CH_2)_2S(CH_2)_2CN$ | |
| 308 | CH | $CF_3$ | 0 | S | $CH_2NHSO_2CH_2CH_3$ | |
| 309 | CH | $CF_3$ | 0 | S | $CH_2NHSO_2CH_2C_6H_5$ | |
| 310 | CH | $CF_3$ | 0 | S | $(CH_2)_2NHSO_2CH_3$ | |
| 311 | CH | $CF_3$ | 0 | S | $CH_2NHSO_2CH_3$ | |
| 312 | CH | $CF_3$ | 0 | S | $CH(CH_3)CH_2NHC_6H_5$ | |
| 313 | CH | $CF_3$ | 0 | S | $(CH_2)_2S(2\text{-F})—C_6H_4$ | |
| 314 | CH | $CF_3$ | 0 | S | $(CH_2)_6NHCH_2)_6OCH_3$ | |
| 315 | CH | $CF_3$ | 0 | S | $(CH_2)_2NH—(2\text{-F})—C_6H_4$ | |
| 316 | CH | $CF_3$ | 0 | S | $(CH_2)_3NHCH_2CN$ | |
| 317 | CH | $CF_3$ | 0 | S | $(CH_2)_2O(3\text{-Cl})—C_6H_4$ | |
| 318 | CH | $CF_3$ | 0 | S | $(CH_2)_6NHCH_2CF_3$ | |
| 319 | CH | $CF_3$ | 0 | S | $(CH_2)_2O(3\text{-}CH_3)—C_6H_4$ | |
| 320 | CH | $CF_3$ | 0 | O | $CH_2NHC_6H_5$ | |
| 321 | CH | $CF_3$ | 0 | O | $(CH_2)_4S(2\text{-Br})—C_6H_4$ | |
| 322 | CH | $CF_3$ | 0 | O | $(CH_2)_6NH(CH_2)_2OCH_3$ | |

TABLE 1-continued

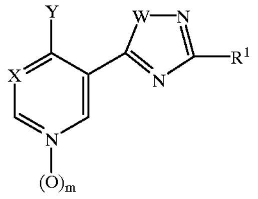

| No. | X | Y | m | W | $R^1$ | m.p. [° C.] |
|---|---|---|---|---|---|---|
| 323 | CH | $CF_3$ | 0 | O | $(CH_2)_2NH(CH_2)_4OCH_3$ | |
| 324 | CH | $CF_3$ | 0 | O | $(CH_2)_3NH$—(4-CN)—$C_6H_4$ | |
| 325 | CH | $CF_3$ | 0 | O | $(CH_2)_2O(3\text{-}CH_3)$—$C_6H_4$ | |
| 326 | CH | $CF_3$ | 0 | O | $(CH_2)_4NHCH_2CF_3$ | |
| 327 | CH | $CF_3$ | 0 | O | $(CH_2)_4NHCH_2CN$ | |
| 328 | CH | $CF_3$ | 0 | O | $(CH_2)_3O(4\text{-}OCH_3)$—$C_6H_4$ | |
| 329 | CH | $CF_3$ | 0 | O | $CH_2SO_2$-tert-$C_4H_9$ | oil |
| 330 | CH | $CF_3$ | 0 | O | $CH_2SO_2$—(4-F)—$C_6H_4$ | oil |
| 331 | CH | $CF_3$ | 0 | O | $CH_2SO_2$—$C_6H_5$ | oil |
| 332 | CH | $CF_3$ | 0 | O | $CH_2SOCH_3$ | 63 |
| 333 | CH | $CF_3$ | 0 | O | $CH_2SO$—$C_6H_5$ | oil |
| 334 | CH | $CF_3$ | 0 | O | $CH_2CONH(CH_2)_2CH_3$ | 80–82 |
| 335 | CH | $CF_3$ | 0 | O | $(4\text{-}OCF_3)$—$C_6H_4$ | 57–59 |
| 336 | CH | $CF_3$ | 0 | O | $CH_2OCH_3$ | oil |
| 337 | CH | $CF_3$ | 0 | O | 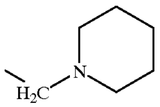 | 53–54 |
| 338 | CH | $CF_3$ | 0 | O | 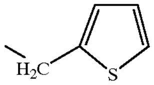 | oil |
| 339 | CH | $CF_3$ | 0 | O | $CH_2CH_2OCH_2CH_3$ | oil |
| 340 | CH | $CF_3$ | 0 | O | $CH_2CH_2NC_6H_5$ | 80–83 |
| 341 | CH | $CF_3$ | 0 | O | 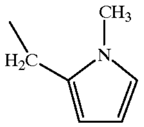 | 80–81 |
| 342 | CH | $CF_3$ | 0 | O | 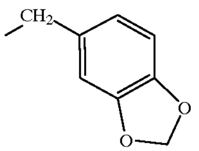 | 110–111 |
| 343 | CH | $CF_3$ | 0 | O | $CH_2CH_2O(CO)$—(4-Cl)—$C_6H_4$ | 80–82 |
| 344 | CH | $CF_3$ | 0 | O | $CH_2$—$(4\text{-}OCH_3)$—$C_6H_4$ | 54–55 |
| 345 | CH | $CF_3$ | 0 | O | $CH_2$—(3-Cl)—$C_6H_4$ | 51–52 |
| 346 | CH | $CF_3$ | 0 | O | $CH_2$-cyclo-$C_3H_5$ | oil |
| 347 | CH | $CF_3$ | 0 | O | $CH_2$—$(4\text{-}C_6H_5)$—$C_6H_4$ | oil |
| 348 | CH | $CF_3$ | 0 | O | 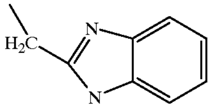 | 143–144 |
| 349 | CH | $CF_3$ | 0 | O | $CH_2CH_2O(CO)$—$(2,6\text{-}F_2)$—$C_6H_3$ | 57–58 |
| 350 | CH | $CF_3$ | 0 | O | $CH_2CH_2O(CO)$—$(4\text{-}NO_2)$—$C_6H_4$ | 80–81 |
| 351 | CH | $CF_3$ | 0 | O | $CH_2$—$(2,6\text{-}Cl_2)$—$C_6H_3$ | 91–92 |
| 352 | CH | $CF_3$ | 0 | O | $CH_2CH_2OSO_2CH_3$ | oil |
| 353 | CH | $CF_3$ | 0 | O | $CH_2CH_2O(CO)$-tert-$C_4H_9$ | oil |
| 354 | CH | $CF_3$ | 0 | O | $CH_2$—(3-F)—$C_6H_4$ | 50–51 |
| 355 | CH | $CF_3$ | 0 | O | $CH_2CONCH_2C{\equiv}CH$ | 129–131 |
| 356 | CH | $CF_3$ | 0 | O | $CH_2CH_2O(CO)$-cyclo-$C_3H_7$ | oil |

TABLE 1-continued

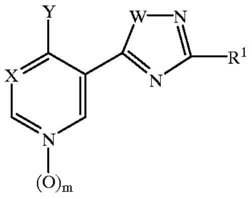

| No. | X | Y | m | W | $R^1$ | m.p. [° C.] |
|---|---|---|---|---|---|---|
| 357 | CH | $CF_3$ | 0 | O | $CH_2CH_2O(CO)CH_3$ | oil |
| 358 | CH | $CF_3$ | 0 | O | $CH_2$—$[2,4\text{-}(CH_3)_2]$—$C_6H_3$ | 85–86 |
| 359 | CH | $CF_3$ | 0 | O | $CH_2CONCH_2CH{=}CH_2$ | 210–212 |
| 360 | CH | $CF_3$ | 0 | O | $CH_2CON(CH_2CH_3)_2$ | oil |
| 361 | CH | $CF_3$ | 0 | O | $CH_2CON(CH_2)_3CH_3$ | 77–79 |
| 362 | CH | $CF_3$ | 0 | O | $CH_2CONCH_2$—(2-furyl) | 139–141 |
| 363 | CH | $CF_3$ | 0 | O | $CH_2CONCH(CH_3)_2$ | 112–114 |
| 364 | CH | $CF_3$ | 0 | O | $CH_2CONCH(CH_3)[(CH_2)_4CH_3]$ | 73–75 |
| 365 | CH | $CF_3$ | 0 | O | $CH_2CONCH_2CH_2C_6H_5$ | 120–122 |
| 366 | CH | $CF_3$ | 0 | O | $CH_2CONCH_2CH_2OCH_2CH_3$ | 78 |
| 367 | CH | $CF_3$ | 0 | O | $CH_2CONCH_2CF_3$ | 176–178 |
| 368 | CH | $CF_3$ | 0 | O | $CH_2CONCH(CH_3)[(CH_2)_5CH_3]$ | 85–86 |
| 369 | CH | $CF_3$ | 0 | O | 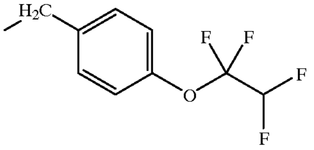 | oil |
| 370 | CH | $CF_3$ | 0 | O | 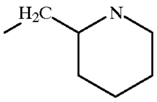 | oil |
| 371 | CH | $CF_3$ | 0 | O | $CH_2CH_2$—(1-pyrryl) | oil |
| 372 | CH | $CF_3$ | 0 | O | $CH_2CH_2C_6H_5$ | oil |
| 373 | CH | $CF_3$ | 0 | O | $CH_2Cl$ | 53–54 |
| 374 | CH | $CF_3$ | 0 | O | $(CH_2)_3OH$ | 38–39 |
| 375 | CH | $CF_3$ | 0 | O | $CH_2CONCH(CH_3)[(CH_2)_2]CH_3$ | 68–69 |
| 376 | CH | $CF_3$ | 0 | O | $CH_2CH(OCH_3)_2$ | oil |
| 377 | CH | $CF_3$ | 0 | O | $CH_2CONCH_2C(CH_3)_3$ | oil |
| 378 | CH | $CF_3$ | 0 | O | $CH_2CONC(CH_3)_2(CH_2CH_3)$ | oil |
| 379 | CH | $CF_3$ | 0 | O | $CH_2CONCH_2CH_2$-cyclo-$C_6H_{11}$ | 82–85 |
| 380 | CH | $CF_3$ | 0 | O | $CH_2CONCH(CH_3)$(1-naphthyl) | 142–146 |
| 381 | CH | $CF_3$ | 0 | O | $(CH_2)_3Cl$ | oil |
| 382 | CH | $CF_3$ | 0 | O | $CH_2CON$-tert-$C_4H_9$ | oil |
| 383 | CH | $CF_3$ | 0 | O | $CH_2CON(\text{iso-}C_3H_7)_2$ | 70–72 |
| 384 | CH | $CF_3$ | 0 | O | $CH_2CON(CH_2)_7CH_3$ | 79–81 |
| 385 | CH | $CF_3$ | 0 | O | $CH_2CON$-cyclo-$C_6H_{11}$ | 119–121 |
| 386 | CH | $CF_3$ | 0 | O | $CH_2CONCH_2CH_2$—(4-Cl)—$C_6H_4$ | 120–121 |
| 387 | CH | $CF_3$ | 0 | O | $CH_2CONCH_2$-(2-thienyl) | 137–139 |
| 388 | CH | $CF_3$ | 0 | O | 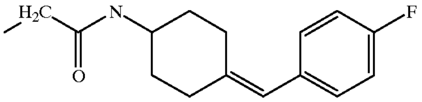 | 151–153 |
| 389 | CH | $CF_3$ | 0 | O | $CH_2CONHCH(CH_3)(CH_2CH_3)$ | 87–89 |
| 390 | CH | $CF_3$ | 0 | O | $(CH_2)_3SCH_3$ | oil |
| 391 | CH | $CF_3$ | 0 | O | $(CH_2)_3SOCH_3$ | oil |
| 392 | CH | $CF_3$ | 0 | O | $CH_2CONC(CH_3)_2(C{\equiv}CH)$ | 111–113 |
| 393 | CH | $CF_3$ | 0 | O | $CH_2CONCH(CH_3)CH_2CH_2CH(CH_3)_2$ | 72–74 |
| 394 | CH | $CF_3$ | 0 | O | 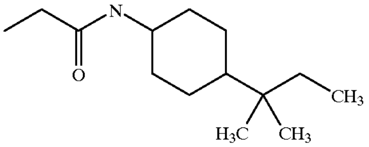 | oil |

TABLE 1-continued

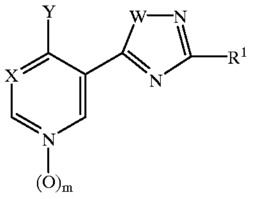

| No. | X | Y | m | W | $R^1$ | m.p. [° C.] |
|---|---|---|---|---|---|---|
| 395 | CH | $CF_3$ | 0 | O | $CH_2CON$-cyclo-$C_5H_9$ | 110–112 |
| 396 | CH | $CF_3$ | 0 | O | $CH_2CON(CH_2)_4CH_3$ | 75–77 |
| 397 | CH | $CF_3$ | 0 | O | 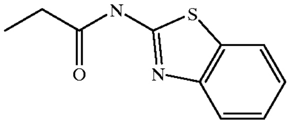 | 190–192 |
| 398 | CH | $CF_3$ | 0 | O | $CH_2CON(3\text{-}CF_3)C_6H_4$ | 136–138 |
| 399 | CH | $CF_3$ | 0 | O | $CH_2CON$-cyclo-$C_8H_{17}$ | 115–117 |
| 400 | CH | $CF_3$ | 0 | O | 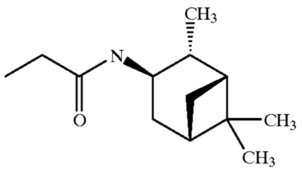 | oil |
| 401 | CH | $CF_3$ | 0 | O | $CH_2CON$-Adamantyl | oil |
| 402 | CH | $CF_3$ | 0 | O | $CH_2CON(CH_2CH_2CH_3)_2$ | oil |
| 403 | CH | $CF_3$ | 0 | O | $CH_2CONCH(CH_3)[(4\text{-}F)—C_6H_4]$ | 111–113 |
| 404 | CH | $CF_3$ | 0 | O | $CH_2CONCH_2CH(CH_3)_2$ | 91–93 |
| 405 | CH | $CF_3$ | 0 | O | 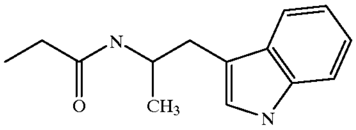 | Oil |
| 406 | CH | $CF_3$ | 0 | O | $CH_2CONCH_2CH_2OC_6H_5$ | 99–101 |
| 407 | CH | $CF_3$ | 0 | O | $CH_2CH{=}NOCH_3$ | oil |
| 408 | CH | $CF_3$ | 0 | O | $CH_2CONCH_2CH_2—[3,4\text{-}(OCH_3)_2]C_6H_3$ | 123–125 |
| 409 | CH | $CF_3$ | 0 | O | $CH_2CON—(2\text{-}Cl)C_6H_4$ | 138–140 |
| 410 | CH | $CF_3$ | 0 | O | $CH_2CON—(2\text{-}SCH_3)C_6H_4$ | 136–138 |
| 411 | CH | $CF_3$ | 0 | O | 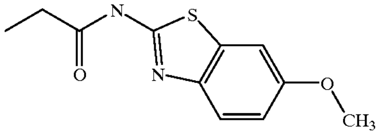 | 222–225 |
| 412 | CH | $CF_3$ | 0 | O | 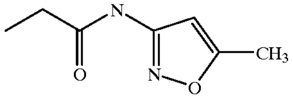 | 207–209 |
| 413 | CH | $CF_3$ | 0 | O | $CH_2CON—(3\text{-}Br)C_6H_4$ | 129–131 |
| 414 | CH | $CF_3$ | 0 | O | $CH_2CON—N—(2,4,6\text{-}Cl_3)C_6H_2$ | 153–155 |
| 415 | CH | $CF_3$ | 0 | O | $CH_2CON—(4\text{-}I)C_6H_4$ | 143–145 |
| 416 | CH | $CF_3$ | 0 | O | $CH_2CON—NCOCH_2$(3-Thienyl) | 185–187 |
| 417 | CH | $CF_3$ | 0 | O | $CH_2CH_2CHO$ | oil |
| 418 | CH | $CF_3$ | 0 | O | $CH_2CON(CH_3)[(CH_2)_3CH_3]$ | oil |
| 419 | CH | $CF_3$ | 0 | O | $CH_2CON—(3,5\text{-}Cl_2\text{-}2,4\text{-}F_2)C_6H$ | 166–167 |
| 420 | CH | $CF_3$ | 0 | O | $CH_2CON—C_6H_5$ | 215–217 |
| 421 | CH | $CF_3$ | 0 | O | $CH_2CON(CH_3)(C_6H_{11})$ | oil |
| 422 | CH | $CF_3$ | 0 | O | $CH_2CON(CH_2CH_3)(CH_2CH{=}CH_2)$ | oil |

TABLE 1-continued

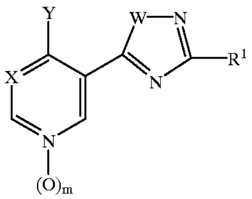

| No. | X | Y | m | W | $R^1$ | m.p. [° C.] |
|---|---|---|---|---|---|---|
| 423 | CH | $CF_3$ | 0 | O | $CH_2CON(CH_2CH_3)[CH(CH_3)_2]$ | oil |
| 424 | CH | $CF_3$ | 0 | O | $CH_2CONCH(CH_3)[(CH_3)_2]$ | 108–110 |
| 425 | CH | $CF_3$ | 0 | O | $CH_2CON(CH_2CH_3)[CH_2C({=}CH_2)(CH_3)]$ | oil |
| 426 | CH | $CF_3$ | 0 | O | $CH_2CONCH_2$(4-tert-$C_4H_9)C_6H_4$ | oil |
| 427 | CH | $CF_3$ | 0 | O | $CH_2CONCH(CH_3)$(tert-$C_4H_9$) | oil |
| 428 | CH | $CF_3$ | 0 | O | $CH_2CONCH(CH_3)[CH_2CH(CH_3)(CH_2CH_3)]$ | oil |
| 429 | CH | $CF_3$ | 0 | O | $CH_2CONCH_2COOCH_2CH_3$ | 103–105 |
| 430 | CH | $CF_3$ | 0 | O | $CH_2CON[(CH_2)_2CH_3](CH_2$-cyclo-$C_3H_7)$ | oil |
| 431 | CH | $CF_3$ | 0 | O | $CH_2CONCH(CH_3)CH_2CH_2CH(CH_3)_2$ | 80–82 |
| 432 | CH | $CF_3$ | 0 | O | $CH_2CONCH(CH_2CH_3)[CH_2CH(CH_3)_2]$ | oil |
| 433 | CH | $CF_3$ | 0 | O | $CH_2C{=}O$—(1-Piperidinyl) | oil |
| 434 | CH | $CF_3$ | 0 | O | 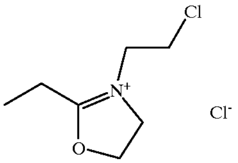 | 180–182 |
| 435 | CH | $CF_3$ | 0 | O | $CH_2CONCH_2C({=}CH_2)(CH_3)$ | 86–87 |
| 436 | CH | $CF_3$ | 0 | O | $CH_2CONCH[CH(CH_3)_2](COOCH_3)$ | oil |
| 437 | CH | $CF_3$ | 0 | O | $CH_2CONCH_2$-cyclo-$C_3H_7$ | oil |
| 438 | CH | $CF_3$ | 0 | O | $CH_2CON(CH_2)_5OH$ | oil |
| 439 | CH | $CF_3$ | 0 | O | $CH_2CON(CH_3)(CH_2CO_2CH_3)$ | oil |
| 440 | CH | $CF_3$ | 0 | O | $CH_2CON(CH_3)(CH_2CN)$ | oil |
| 441 | CH | $CF_3$ | 0 | O | $CH_2CONCH[CH_2CH(CH_3)_2](CO_2CH_3)$ | oil |
| 442 | CH | $CF_3$ | 0 | O | $CH_2CON$-(1-Piperidinyl) | oil |
| 443 | CH | $CF_3$ | 0 | O | $CH_2CONCH_2CH_2OCH_3$ | 97–99 |
| 444 | CH | $CF_3$ | 0 | O | $CH_2CH_2SC_6H_5$ | oil |
| 445 | CH | $CF_3$ | 0 | O | $CH_2CH_2SCH_3$ | oil |
| 446 | CH | $CF_3$ | 0 | O | $CH_2CH_2SCH_2C_6H_5$ | oil |
| 447 | CH | $CF_3$ | 0 | O | 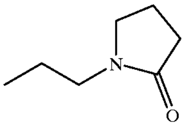 | oil |
| 448 | CH | $CF_3$ | 0 | O | $CH_2CON$—(2-OH)$C_6H_4$ | 162–164 |
| 449 | CH | $CF_3$ | 0 | O | $CH_2CON$—(3-OH)$C_6H_4$ | oil |
| 450 | CH | $CF_3$ | 0 | O | $CH_2CON$—(2-$CH_3$)$C_6H_4$ | 163–164 |
| 451 | CH | $CF_3$ | 0 | O | $CH_2CON$—(3-$NO_2$)$C_6H_4$ | 176–178 |
| 452 | CH | $CF_3$ | 0 | O | $CH_2CON$—(3-$OCF_2CHFCl$)$C_6H_4$ | 120–121 |
| 453 | CH | $CF_3$ | 0 | O | $CH_2CON$—(3-$CF_3$-4-F)$C_6H_3$ | 168–170 |
| 454 | CH | $CF_3$ | 0 | O | $CH_2CON$—(2,4-$Cl_2$)$C_6H_3$ | 120–122 |
| 455 | CH | $CF_3$ | 0 | O | $CH_2CON$—(2-F,4.Cl)$C_6H_3$ | 148–151 |
| 456 | CH | $CF_3$ | 0 | O | $CH_2CON$—[2,4-$(CH_3)_2$]$C_6H_3$ | 123–125 |
| 457 | CH | $CF_3$ | 0 | O | $CH_2CON$—[2,3-$(CH_3)_2$]$C_6H_3$ | waxy |
| 458 | CH | $CF_3$ | 0 | O | 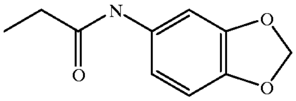 | waxy |
| 459 | CH | $CF_3$ | 0 | O | $CH_2CON$—(2-$CH_3$-3-Cl)$C_6H_3$ | 160–162 |
| 460 | CH | $CF_3$ | 0 | O | $CH_2CON(CH_2CH_3)(C_6H_5)$ | oil |

TABLE 1-continued

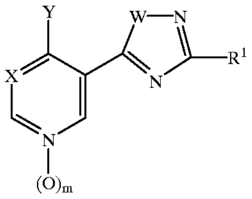

| No. | X | Y | m | W | $R^1$ | m.p. [° C.] |
|---|---|---|---|---|---|---|
| 461 | CH | $CF_3$ | 0 | O | 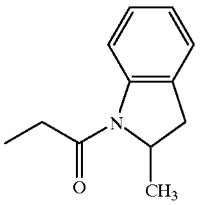 | 124–126 |
| 462 | CH | $CF_3$ | 0 | O | $CH_2CON(2\text{-}OCH_3\text{-}5\text{-}Ph)C_6H_3$ | 167–169 |
| 463 | CH | $CF_3$ | 0 | O | 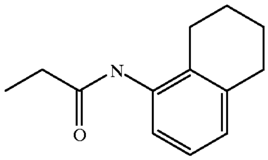 | 157–158 |
| 464 | CH | $CF_3$ | 0 | O | $CH_2CON—(3\text{-}NO_2\text{-}4\text{-}Cl)C_6H_3$ | oil |
| 465 | CH | $CF_3$ | 0 | O | $CH_2CON—(2\text{-}Cl\text{-}4\text{-}CH_3)C_6H_3$ | 106–108 |
| 466 | CH | $CF_3$ | 0 | O | $CH_2CON—(3\text{-}OCH_2CH_3)C_6H_4$ | waxy |
| 467 | CH | $CF_3$ | 0 | O | 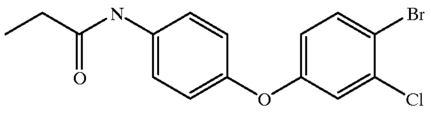 | 169–171 |
| 468 | CH | $CF_3$ | 0 | O | $CH_2CON—(4\text{-}CH_3)C_6H_4$ | 139–141 |
| 469 | CH | $CF_3$ | 0 | O | $CH_2CON$—(1-Naphthyl) | 155–157 |
| 470 | CH | $CF_3$ | 0 | O | $CH_2CON—(3\text{-}I)C_6H_4$ | 135–137 |
| 471 | CH | $CF_3$ | 0 | O | $CH_2CON—(2\text{-}OCH_2CH_3)C_6H_4$ | 138 |
| 472 | CH | $CF_3$ | 0 | O | $CH_2CON—(2\text{-}OCH_3)C_6H_4$ | 130–132 |
| 473 | CH | $CF_3$ | 0 | O | $CH_2CON—[3,5\text{-}(OCH_3)_2]C_6H_3$ | 130–132 |
| 474 | CH | $CF_3$ | 0 | O | $CH_2CON—(4\text{-}Cl)C_6H_4$ | 139–141 |
| 475 | CH | $CF_3$ | 0 | O | $CH_2CON—(3\text{-}CH_3)C_6H_4$ | oil |
| 476 | CH | $CF_3$ | 0 | O | $CH_2CON—(3\text{-}OCH_3)C_6H_4$ | oil |
| 477 | CH | $CF_3$ | 0 | O | $CH_2CON—(4\text{-}CH_2CH_3)C_6H_4$ | 122–123 |
| 478 | CH | $CF_3$ | 0 | O | $CH_2CON—(4\text{-}CF_3)C_6H_4$ | 151–152 |
| 479 | CH | $CF_3$ | 0 | O | $CH_2CON—(2\text{-}CH_3\text{-}4\text{-}Cl)C_6H_3$ | 165–167 |
| 480 | CH | $CF_3$ | 0 | O | $CH_2CH_2NCH_2C_6H_5$ | oil |
| 481 | CH | $CF_3$ | 0 | O | $CH_2CH_2NCH_2$—(3-Pyridyl) | oil |
| 482 | CH | $CF_3$ | 0 | O | $CH_2CH{=}NOCH_2CH_3$ | oil |
| 483 | CH | $CF_3$ | 0 | O | $CH_2CH{=}NOC_6H_5$ | oil |
| 484 | CH | $CF_3$ | 0 | O | $CH_2CON—(4\text{-}NO_2)C_6H_4$ | 181–183 |
| 485 | CH | $CF_3$ | 0 | O | $CH_2CON—(2\text{-}CH_3\text{-}4\text{-}NO_2)C_6H_3$ | 129–131 |
| 486 | CH | $CF_3$ | 0 | O | $CH_2CON—(2\text{-}Cl\text{-}3\text{-}CF_3)C_6H_3$ | 136 |
| 487 | CH | $CF_3$ | 0 | O | $CH_2CON—(2\text{-}CN\text{-}4\text{-}Cl)C_6H_3$ | 157–159 |
| 488 | CH | $CF_3$ | 0 | O | $CH_2CON—(3,5\text{-}Cl_2)C_6H_3$ | 167–169 |
| 489 | CH | $CF_3$ | 0 | O | $CH_2CON—(3,5\text{-}Cl_2\text{-}4\text{-}OCF_2CHF_2)C_6H_2$ | 132–134 |
| 490 | CH | $CF_3$ | 0 | O | $CH_2CON—(2,4,5\text{-}Cl_3)C_6H_2$ | 146 |
| 491 | CH | $CF_3$ | 0 | O | $CH_2CON—(3,5\text{-}Cl_2\text{-}4\text{-}OCF_2CHFCF_3)C_6H_2$ | 124–126 |
| 492 | CH | $CF_3$ | 0 | O | $CH_2CON—(2\text{-}CF_3\text{-}4\text{-}Cl)C_6H_3$ | 136 |

TABLE 1-continued
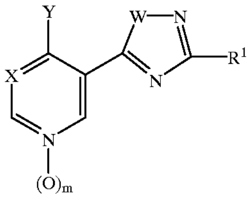
| No. | X | Y | m | W | $R^1$ | m.p. [° C.] |
|---|---|---|---|---|---|---|
| 493 | CH | $CF_3$ | 0 | O | 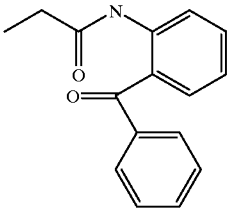 | oil |
| 494 | CH | $CF_3$ | 0 | O | 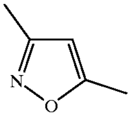 | 91–93 |
| 495 | CH | $CF_3$ | 0 | O | 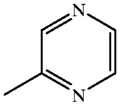 | 123–125 |
| 496 | CH | $CF_3$ | 0 | O | 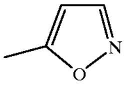 | 81–83 |
| 497 | CH | $CF_3$ | 0 | O | 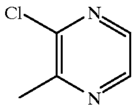 | 113–115 |
| 498 | CH | $CF_3$ | 0 | O | COOH | 155–157 |
| 499 | CH | $CF_3$ | 0 | O | 4-F-$C_6H_4$ | 104–106 |
| 500 | CH | $CF_3$ | 0 | O | $CON(C_2H_5)_2$ | oil |
| 501 | CH | $CF_3$ | 0 | O | $CONCH(CH_3)_2$ | oil |
| 502 | CH | $CF_3$ | 0 | O | $CON(CH_3)_2$ | 52–54 |
| 503 | CH | $CF_3$ | 0 | O | $CONHCH_2CCH$ | 105–107 |
| 504 | CH | $CF_3$ | 0 | O | CONH-cyclo-$C_3H_5$ | 101–103 |
| 505 | CH | $CF_3$ | 0 | O | $CONH_2$ | 206–208 |
| 506 | CH | $CF_3$ | 0 | O | 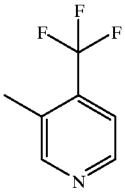 | 72–74 |
| 507 | CH | $CF_3$ | 0 | O | 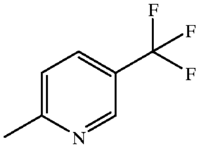 | 98–100 |

TABLE 1-continued

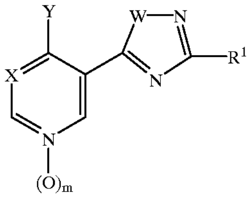

| No. | X | Y | m | W | $R^1$ | m.p. [° C.] |
|---|---|---|---|---|---|---|
| 508 | CH | $CF_3$ | 0 | O | 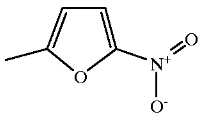 | 108–110 |
| 509 | CH | $CF_3$ | 0 | O | 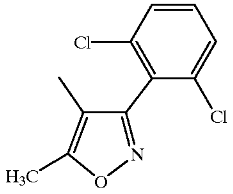 | 140–142 |
| 510 | CH | $CF_3$ | 0 | O | $CONHCH_3$ | 127–129 |
| 511 | CH | $CF_3$ | 0 | O | $CONHCH_2CH{=}CH_2$ | oil |
| 512 | CH | $CF_3$ | 0 | O | $CON(CH_2CN)_2$ | 90–92 |
| 513 | CH | $CF_3$ | 0 | O | $4\text{-}(t\text{-}C_4H_9)\text{—}C_6H_4$ | 64–66 |
| 514 | CH | $CF_3$ | 0 | O | $4\text{-}CF_3\text{—}C_6H_4$ | 89–91 |
| 515 | CH | $CF_3$ | 0 | O | $4\text{-}CH_3\text{-}3\text{-}F\text{—}C_6H_3$ | 104–106 |
| 516 | CH | $CF_3$ | 0 | O | $2,4\text{-di-}Cl\text{—}C_6H_3$ | 70–72 |
| 517 | CH | $CF_3$ | 0 | O | $4\text{-}(NHSO_2CH_3)\text{—}C_6H_4$ | 204–206 |
| 518 | CH | $CF_3$ | 0 | O | $2,6\text{-di-}Cl\text{—}C_6H_3$ | 139–141 |
| 519 | CH | $CF_3$ | 0 | O | $COOCH_2C_6H_5$ | 83–85 |
| 520 | CH | $CF_3$ | 0 | O | $CONHC_3H_7$ | oil |
| 521 | CH | $CF_3$ | 0 | O | $3,5\text{-di-}Br\text{-}4\text{-}(OCH_3)\text{—}C_6H_2$ | 132–134 |
| 522 | CH | $CF_3$ | 0 | O | $CHCl_2$ | oil |
| 523 | CH | $CF_3$ | 0 | O | $CCl_3$ | oil |
| 524 | CH | $CF_3$ | 0 | O | $CH(OCH_3)_2$ | oil |
| 525 | CH | $CF_3$ | 0 | O | $3\text{-}CF_3\text{—}C_6H_4$ | 57–59 |
| 526 | CH | $CF_3$ | 0 | O | $CON(CH_2)_5$ | oil |
| 527 | CH | $CF_3$ | 0 | O | $CON(CH_3)CH_2C_6H_5$ | oil |
| 528 | CH | $CF_3$ | 0 | O | $CONHCH_2C_6H_5$ | 96–98 |
| 529 | CH | $CF_3$ | 0 | O | 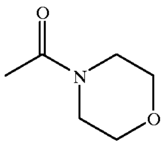 | oil |
| 530 | CH | $CF_3$ | 0 | O | $CONH\text{-}n\text{-}C_6H_{13}$ | oil |
| 531 | CH | $CF_3$ | 0 | O | $CON(CH_2CH_3)CH_2C_6H_5$ | oil |
| 532 | CH | $CF_3$ | 0 | O | $CONH\text{-}c\text{-}C_6H_{11}$ | 115–117 |
| 533 | CH | $CF_3$ | 0 | O | $CON(n\text{-}C_4H_9)_2$ | oil |
| 534 | CH | $CF_3$ | 0 | O | 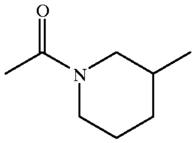 | oil |
| 535 | CH | $CF_3$ | 0 | O | $CONH\text{-}i\text{-}C_4H_9$ | oil |

TABLE 1-continued

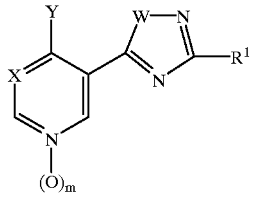

| No. | X | Y | m | W | $R^1$ | m.p. [° C.] |
|---|---|---|---|---|---|---|
| 536 | CH | $CF_3$ | 0 | O | 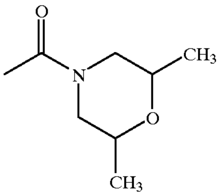 | oil |
| 537 | CH | $CF_3$ | 0 | O | $CON(CH_2)_4$ | 68–70 |
| 538 | CH | $CF_3$ | 0 | O | $CON(CH_3)n\text{-}C_6H_{13}$ | oil |
| 539 | CH | $CF_3$ | 0 | O | 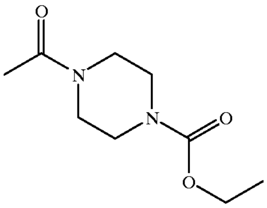 | oil |
| 540 | CH | $CF_3$ | 0 | O | $CON(CH_3)CH_2CH_3$ | oil |
| 541 | CH | $CF_3$ | 0 | O | $CONHOCH_3$ | oil |
| 542 | CH | $CF_3$ | 0 | O | 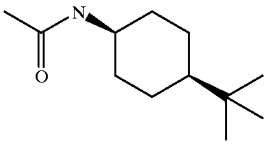 | oil |
| 543 | CH | $CF_3$ | 0 | O | $CON(CH_3)CH_2CH_2CH_3$ | oil |
| 544 | CH | $CF_3$ | 0 | O | $CONHCH_2CH(OCH_3)_2$ | oil |
| 545 | CH | $CF_3$ | 0 | O | $CONH\text{-}t\text{-}C_4H_9$ | 113–115 |
| 546 | CH | $CF_3$ | 0 | O | $CONHCH_2\text{-}4\text{-}Cl—C_6H_4$ | oil |
| 547 | CH | $CF_3$ | 0 | O | $CONHCH(CH_3)C_6H_5$ | oil |
| 548 | CH | $CF_3$ | 0 | O | $CONHCH_2CH_2OCH_3$ | 92–94 |
| 549 | CH | $CF_3$ | 0 | O | 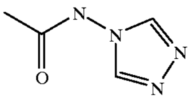 | 190–192 |
| 550 | CH | $CF_3$ | 0 | O | $CONHC(CH_3)_2CCH$ | 90–92 |
| 551 | CH | $CF_3$ | 0 | O | $CONHCH_2$-2-Furyl | 93–95 |
| 552 | CH | $CF_3$ | 0 | O | $CON(CH_2)_3$ | 91–93 |
| 553 | CH | $CF_3$ | 0 | O | $CONHCH_2\text{-}c\text{-}C_3H_5$ | oil |
| 554 | CH | $CF_3$ | 0 | O | $CONHC(CH_3)_2CH_2CH_3$ | oil |
| 555 | CH | $CF_3$ | 0 | O | $CONH(CH_2)_3C_6H_5$ | oil |
| 556 | CH | $CF_3$ | 0 | O | $CONHCH_2$-3-Pyridyl | 132–134 |
| 557 | CH | $CF_3$ | 0 | O | $CON(CH_3)\text{-}n\text{-}C_4H_9$ | oil |
| 558 | CH | $CF_3$ | 0 | O | $CON(CH_2CH_3)\text{-}i\text{-}C_3H_7$ | oil |
| 559 | CH | $CF_3$ | 0 | O | 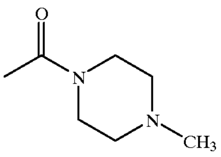 | oil |

TABLE 1-continued

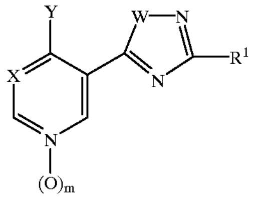

| No. | X | Y | m | W | $R^1$ | m.p. [° C.] |
|---|---|---|---|---|---|---|
| 560 | CH | $CF_3$ | 0 | O | $CONHCH_2CH_2Cl$ | oil |
| 561 | CH | $CF_3$ | 0 | O | $CONHCH_2CN$ | 152–157 |
| 562 | CH | $CF_3$ | 0 | O | $CON(CH_3)OCH_3$ | oil |
| 563 | CH | $CF_3$ | 0 | O | $CON(CH_3)CH_2CH{=}CH_2$ | oil |
| 564 | CH | $CF_3$ | 0 | O | $CONHCH_2COOCH_3$ | oil |
| 565 | CH | $CF_3$ | 0 | O | $CON(CH_3)$-i-$C_3H_7$ | oil |
| 566 | CH | $CF_3$ | 0 | O | $CON(CH_3)CH_2CH_2CN$ | oil |
| 567 | CH | $CF_3$ | 0 | O | $CON(CH_3)CH_2CH(OCH_3)_2$ | oil |
| 568 | CH | $CF_3$ | 0 | O | $CON(CH_3)CH_2CH(—CH_2CH_2O—)$ | oil |
| 569 | CH | $CF_3$ | 0 | O | $CONHCH_2C({=}CH_2)CHH_3$ | oil |
| 570 | CH | $CF_3$ | 0 | O | $CON(CH_2CH_3)CH_2CH{=}CH_2$ | oil |
| 571 | CH | $CF_3$ | 0 | O | $CONHC_6H_5$ | 83–85 |
| 572 | CH | $CF_3$ | 0 | O | $CON(CH_3)CH_2CCH$ | oil |
| 573 | CH | $CF_3$ | 0 | O | $CON(CH_3)CH_2CN$ | oil |
| 574 | CH | $CF_3$ | 0 | O | $CON(CH_3)CH_2CH_2N(CH_3)_2$ | oil |
| 575 | CH | $CF_3$ | 0 | O | $CONHOCH_2CH_3$ | 114–116 |
| 576 | CH | $CF_3$ | 0 | O | $CONHCH_2CF_3$ | 74–76 |
| 577 | CH | $CF_3$ | 0 | O | $CON(CH_2CH_2Cl)_2$ | oil |
| 578 | CH | $CF_3$ | 0 | O | CONH-c-$C_4H_7$ | oil |
| 579 | CH | $CF_3$ | 0 | O | $CON(CH_2CH_2CH_3)CH_2$-c-$C_3H_5$ | oil |
| 580 | CH | $CF_3$ | 0 | O | $CON(CH_3)$-c-$C_6H_{11}$ | oil |
| 581 | CH | $CF_3$ | 0 | O | $CON(CH_2CH_3)CH_2C({=}CH_2)CH_3$ | oil |
| 582 | CH | $CF_3$ | 0 | O | $CONHOCH_2CH{=}CH_2$ | 90–92 |
| 583 | CH | $CF_3$ | 0 | O | $CONHOCH_2C_6H_5$ | 126–128 |
| 584 | CH | $CF_3$ | 0 | O | $CON(CH_3)CH_2COOCH_3$ | oil |
| 585 | CH | $CF_3$ | 0 | O | $COONHCH_3$ | 230–232 |
| 586 | CH | $CF_3$ | 0 | O | $CONHCH_2CH_3$ | 83–85 |
| 587 | CH | $CF_3$ | 0 | O | $CONHCH(CH_3)COOCH_3$ | 104–106 |
| 588 | CH | $CF_3$ | 0 | O | CONHCH(i-$C_3H_7$)$COOCH_3$ | oil |
| 589 | CH | $CF_3$ | 0 | O | $CON(CH_3)CH_2CON(CH_3)_2$ | oil |
| 590 | CH | $CF_3$ | 0 | O | $CON(CH_3)$-t-$C_4H_9$ | oil |
| 591 | CH | $CF_3$ | 0 | O | CONHO-t-$C_4H_9$ | 103–105 |
| 592 | CH | $CF_3$ | 0 | O | $CON(CH_3)CH$(i-$C_3H_7$)$COOCH_3$ | oil |
| 593 | CH | $CF_3$ | 0 | O | $CH(OCH_2CH_3)_2$ | oil |
| 594 | CH | $CF_3$ | 0 | O | 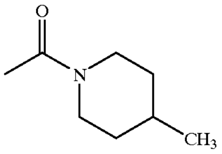 | oil |
| 595 | CH | $CF_3$ | 0 | O | 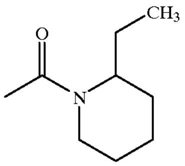 | oil |
| 596 | CH | $CF_3$ | 0 | O | 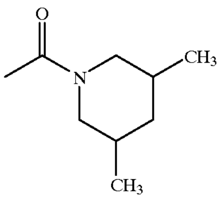 | oil |

TABLE 1-continued

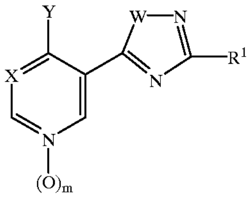

| No. | X | Y | m | W | $R^1$ | m.p. [° C.] |
|---|---|---|---|---|---|---|
| 597 | CH | $CF_3$ | 0 | O | 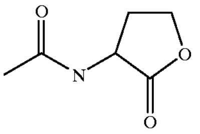 | oil |
| 598 | CH | $CF_3$ | 0 | O | 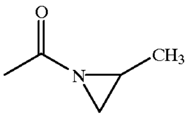 | oil |
| 599 | CH | $CF_3$ | 0 | O | $CONHCH_2CONHCH_3$ | 101–103 |
| 600 | CH | $CF_3$ | 0 | O | $CON(CH_2)_7$ | oil |
| 601 | CH | $CF_3$ | 0 | O | $CON(CH_2)_6$ | oil |
| 602 | CH | $CF_3$ | 0 | O | $CON(CH_2CH_3)CH_2CH_2OCH_3$ | oil |
| 603 | CH | $CF_3$ | 0 | O | 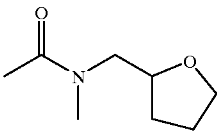 | oil |
| 604 | CH | $CF_3$ | 0 | O | 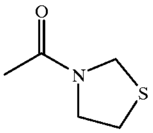 | oil |
| 605 | CH | $CF_3$ | 0 | O | 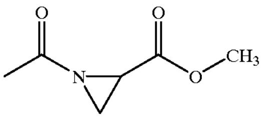 | oil |
| 606 | CH | $CF_3$ | 0 | O | $CON(CH_2CH_3)CH_2CH_2CN$ | oil |
| 607 | CH | $CF_3$ | 0 | O | 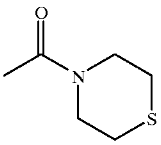 | oil |
| 608 | CH | $CF_3$ | 0 | O | $CON(CH_2CH_3)\text{-n-}C_4H_9$ | oil |
| 609 | CH | $CF_3$ | 0 | O | 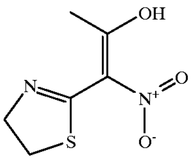 | 179–181 |
| 610 | CH | $CF_3$ | 0 | O | $CONHCH(CH_3)CONHCH_3$ | 136–138 |
| 611 | CH | $CF_3$ | 0 | O | $COON(CH_2)_4$ | 64–66 |
| 612 | CH | $CF_3$ | 0 | O | $CONHCH_2CON(CH_3)_2$ | 107–109 |
| 613 | CH | $CF_3$ | 0 | O | $CON(CH_2COOCH_2CH_3)_2$ | oil |

TABLE 1-continued

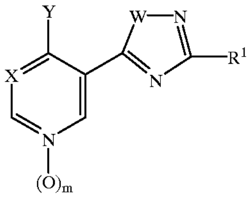

| No. | X | Y | m | W | $R^1$ | m.p. [° C.] |
|---|---|---|---|---|---|---|
| 614 | CH | $CF_3$ | 0 | O | 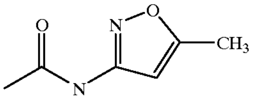 | 180–182 |
| 615 | CH | $CF_3$ | 0 | O | 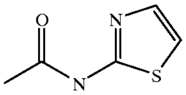 | 221–223 |
| 616 | CH | $CF_3$ | 0 | O | 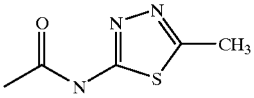 | 234–236 |
| 617 | CH | $CF_3$ | 0 | O | 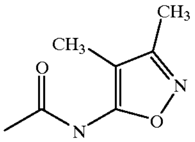 | oil |
| 618 | CH | $CF_3$ | 0 | O | $CON(CH_3)CH_2$-6-Cl-3-pyridyl | oil |
| 619 | CH | $CF_3$ | 0 | O | 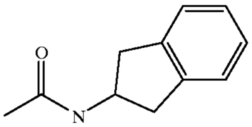 | 105–107 |
| 620 | CH | $CF_3$ | 0 | O | $CONHCH(CH_3)CH(OCH_3)_2$ | oil |
| 621 | CH | $CF_3$ | 0 | O | $CONHCH_2CH_2SCH_3$ | oil |
| 622 | CH | $CF_3$ | 0 | O | $CONHCH(CH_3)CH_2OCH_3$ | 70–72 |
| 623 | CH | $CF_3$ | 0 | O | $CONHCH_2CH_2NHCOCH_3$ | 124–126 |
| 624 | CH | $CF_3$ | 0 | O | $CONH(CH_2)_3OCH_2CH_3$ | oil |
| 625 | CH | $CF_3$ | 0 | O | $CON(CH_2CH_3)CH_2CH_2CH_3$ | oil |
| 626 | CH | $CF_3$ | 0 | O | $CON(CH_2CH_3)CH_2OCH_3$ | oil |
| 627 | CH | $CF_3$ | 0 | O | $CONHCH_2CH_2SCH_2CH_3$ | oil |
| 628 | CH | $CF_3$ | 0 | O | $CONHCH_2CH_2OCH_2CH_3$ | 59–61 |
| 629 | CH | $CF_3$ | 0 | O | 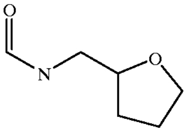 | oil |
| 630 | CH | $CF_3$ | 0 | O | 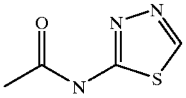 | 174–176 |
| 631 | CH | $CF_3$ | 0 | O | $CONHCH(CH_3)CH(OCH_3)_2$ | oil |
| 632 | CH | $CF_3$ | 0 | O | $CONHCH_2CH_2SCH_3$ | oil |
| 633 | CH | $CF_3$ | 0 | O | $CONHCH(CH_3)CH_2OCH_3$ | 70–72 |
| 634 | CH | $CF_3$ | 0 | O | $CONHCH_2CH_2NHCOCH_3$ | 124–126 |
| 635 | CH | $CF_3$ | 0 | O | $CONH(CH_2)_3OCH_2CH_3$ | oil |
| 636 | CH | $CF_3$ | 0 | O | $CON(CH_2CH_3)CH_2CH_2CH_3$ | oil |

TABLE 1-continued

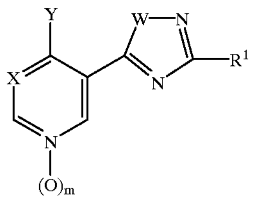

| No. | X | Y | m | W | $R^1$ | m.p. [° C.] |
|---|---|---|---|---|---|---|
| 637 | CH | $CF_3$ | 0 | O | $CON(CH_2CH_3)CH_2OCH_3$ | oil |
| 638 | CH | $CF_3$ | 0 | O | $CONHCH_2CH_2SCH_2CH_3$ | oil |
| 639 | CH | $CF_3$ | 0 | O | $CONHCH(CH_3)CH_2COOCH_2CH_3$ | oil |
| 640 | CH | $CF_3$ | 0 | O | CONH-4-$COOCH_3$—$C_6H_4$ | 189–191 |
| 641 | CH | $CF_3$ | 0 | O | CONH-4-$CONH_2$—$C_6H_4$ | 265–267 |
| 642 | CH | $CF_3$ | 0 | O | $CONHCH_2CH_2Br$ | oil |
| 643 | CH | $CF_3$ | 0 | O | $CONHCH_2CH{=}CHCH_2Cl$ | oil |
| 644 | CH | $CF_3$ | 0 | O | CONH-4-$CONHCH_3$—$C_6H_4$ | 219–221 |
| 645 | CH | $CF_3$ | 0 | O | $CONHCH_2CH_2CH_2Br$ | oil |
| 646 | CH | $CF_3$ | 0 | O | $CONHCH_2CH_2CH_2OCH_3$ | oil |
| 647 | CH | $CF_3$ | 0 | O | CONH-4-$CH_2CH_3$—$C_6H_4$ | 97–99 |
| 648 | CH | $CF_3$ | 0 | O | $CONHCH_2CH_2OCH(CH_3)_2$ | oil |
| 649 | CH | $CF_3$ | 0 | O | $CONHCH_2CH_2CH_2OCH_2CH_3$ | oil |
| 650 | CH | $CF_3$ | 0 | O | 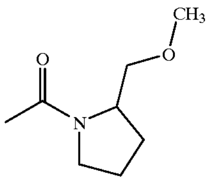 | oil |
| 651 | CH | $CF_3$ | 0 | O | 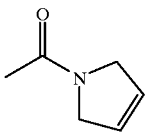 | 64–66 |
| 652 | CH | $CF_3$ | 0 | O | 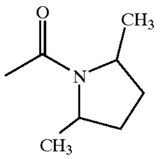 | oil |
| 653 | CH | $CF_3$ | 0 | O | 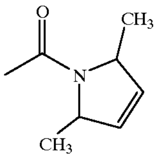 | oil |
| 654 | CH | $CF_3$ | 0 | O | $CH_2CON(CH_3)CH_2CH_3$ | oil |
| 655 | CH | $CF_3$ | 0 | O | $CH_2CON(CH_3)_2$ | 58–60 |
| 656 | CH | $CF_3$ | 0 | O | $CH_2CON(CH_2)_4$ | 101–103 |
| 657 | CH | $CF_3$ | 0 | O | 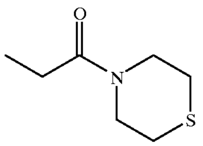 | oil |

TABLE 1-continued

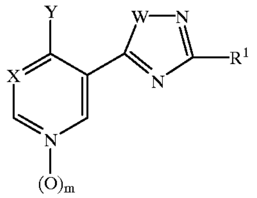

| No. | X | Y | m | W | $R^1$ | m.p. [° C.] |
|---|---|---|---|---|---|---|
| 658 | CH | $CF_3$ | 0 | O | 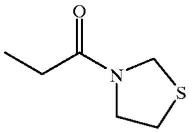 | 90–92 |
| 659 | CH | $CF_3$ | 0 | O | $CH_2CONHCH_2CH_3$ | 104–106 |
| 660 | CH | $CF_3$ | 0 | O | $CH_2CON(CH_3)CH_2CH_2OH$ | oil |
| 661 | CH | $CF_3$ | 0 | O | $CH_2CON(CH_3)CH_2CH_2CH_3$ | oil |
| 662 | CH | $CF_3$ | 0 | O | $CH_2CON(CH_3)CH_2CH(—OCH_2CH_2O—)$ | oil |
| 663 | CH | $CF_3$ | 0 | O | $CH_2CONHCH_2CH_3$ | 104–106 |
| 664 | CH | $CF_3$ | 0 | O | $CH_2CON(CH_3)CH_2CH_2OH$ | oil |
| 665 | CH | $CF_3$ | 0 | O | $CH_2CON(CH_3)CH_2CH_2CH_3$ | oil |
| 667 | CH | $CF_3$ | 0 | O | $CH_2CON(CH_3)CH_2CH(—OCH_2CH_2O—)$ | oil |
| 668 | CH | $CF_3$ | 0 | O | 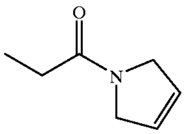 | 79–81 |
| 669 | CH | $CF_3$ | 0 | O | $CH_2CONHCH_2CH_2SCH_3$ | 65–67 |
| 670 | CH | $CF_3$ | 0 | O | $CH_2CONHCH(CH_3)CH_2OCH_3$ | 86–88 |
| 671 | CH | $CF_3$ | 0 | O | $CON(CH_3)CH_2CH_2OCO$-c-$C_4H_7$ | oil |
| 672 | CH | $CF_3$ | 0 | O | $CH_2CONHCH_2CH_2Br$ | 87–89 |
| 673 | CH | $CF_3$ | 0 | O | $CON(CH_3)CH_2CH_2OCOC_6H_5$ | oil |
| 674 | CH | $CF_3$ | 0 | O | $CON(CH_3)CH_2CH_2OCO$-c-$C_3H_5$ | oil |
| 675 | CH | $CF_3$ | 0 | O | CONH-2-$CH_3$—$C_6H_4$ | 104–106 |
| 676 | CH | $CF_3$ | 0 | O | $CH_2CON$(i-$C_3H_7$)-4-F—$C_6H_4$ | 102–104 |
| 677 | CH | $CF_3$ | 0 | O | 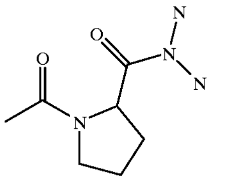 | oil |
| 678 | CH | $CF_3$ | 0 | O | 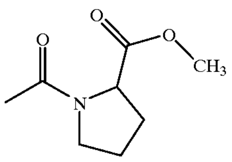 | oil |
| 679 | CH | $CF_3$ | 0 | O | $CON(CH_3)CH_2CH_2OCONHC_6H_5$ | 100–102 |
| 680 | CH | $CF_3$ | 0 | O | $CON(CH_3)CH_2CH_2OCONHCH_2CH_3$ | oil |
| 681 | CH | $CF_3$ | 0 | O | $CON(CH_3)CH_2CH_2OSO_2CH_3$ | oil |
| 682 | CH | $CF_3$ | 0 | O | $CH_2CONH$-c-$C_4H_7$ | 133–135 |
| 683 | CH | $CF_3$ | 0 | O | $CH_2CONHCH_2CN$ | 158–160 |

TABLE 2

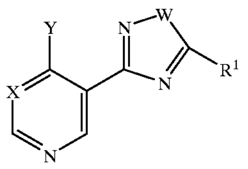

| No. | X | Y | W | $R^1$ | m.p. [° C.] |
|---|---|---|---|---|---|
| 684 | N | $(CF_2)_3$—$CHF_2$ | O | $CH_3$ | |
| 685 | N | $(CF_2)_2$—$CF_3$ | O | $CH_2CH_3$ | |
| 686 | N | $(CF_2)_2$—$CF_3$ | O | $COOCH_2CH_3$ | |
| 687 | N | $(CF_2)_2$—$CF_3$ | O | OH | |
| 688 | N | $(CF_2)_2$—$CF_3$ | O | $OCH_3$ | |
| 689 | N | $CF_2CF_3$ | O | $CH_3$ | |
| 690 | N | $CF_2CF_3$ | O | $CH_2CH_3$ | |
| 691 | N | $CF_2CF_3$ | S | $CH_3$ | |
| 692 | N | $CF_2CF_3$ | S | $CH_2CH_3$ | |
| 693 | N | $CF_2CF_3$ | S | $(CH_2)_2CH_3$ | |
| 694 | CH | $CF_3$ | O | $CH_3$ | oil |
| 695 | CH | $CF_3$ | O | $CH_2CH_3$ | |
| 696 | CH | $CF_3$ | O | $(CH_2)_2CH_3$ | |
| 697 | CH | $CF_3$ | O | $CH(CH_3)_2$ | |
| 698 | CH | $CF_3$ | O | $(CH_2)_3CH_3$ | |
| 699 | CH | $CF_3$ | O | $CH(CH_3)CH_2CH_3$ | |
| 700 | CH | $CF_3$ | O | $CH_2CH(CH_3)_2$ | |
| 701 | CH | $CF_3$ | O | $C(CH_3)_3$ | oil |
| 702 | CH | $CF_3$ | O | $(CH_2)_4CH_3$ | |
| 703 | CH | $CF_3$ | O | $CH(CH_3)(CH_2)_2$—$CH_3$ | |
| 704 | CH | $CF_3$ | O | $(CH_2)_2CH(CH_3)_2$ | |
| 705 | CH | $CF_3$ | O | $CH_2C(CH_3)_3$ | |
| 706 | CH | $CF_3$ | O | cyclo-$C_5H_9$ | |
| 707 | CH | $CF_3$ | O | cyclo-$C_6H_{11}$ | |
| 708 | CH | $CF_3$ | O | CHO | |
| 709 | CH | $CF_3$ | O | $CH{=}CH_2$ | |
| 710 | CH | $CF_3$ | O | $CH_2CH{=}C(CH_3)_2$ | |
| 711 | CH | $CF_3$ | O | $CH_2CH{=}CH_2$ | |
| 712 | CH | $CF_3$ | O | $C(CH_3){=}CH_2$ | |
| 713 | CH | $CF_3$ | O | $(CH_2)_5C{=}CH_2$ | |
| 714 | CH | $CF_3$ | O | $C({=}CHCH_3)CH_3$ | |
| 715 | CH | $CF_3$ | O | $CH_2C{\equiv}CH$ | |
| 716 | CH | $CF_3$ | O | $CH_2CH_2C{\equiv}CH$ | |
| 717 | CH | $CF_3$ | O | $CH_2C{\equiv}CCH_2CH_3$ | |
| 718 | CH | $CF_3$ | O | $(CH_2)_4C{\equiv}CH$ | |
| 719 | CH | $CF_3$ | O | $CHFCF_3$ | |
| 720 | CH | $CF_3$ | O | $COOCH_2CH_3$ | |
| 721 | CH | $CF_3$ | O | $CH_2CH_2OH$ | |
| 722 | CH | $CF_3$ | O | $CH_2CH_2OCH_3$ | |
| 723 | CH | $CF_3$ | O | $CH_2COOC(CH_3)_3$ | |
| 724 | CH | $CF_3$ | O | $CH_2SC_6H_5$ | |
| 725 | CH | $CF_3$ | O | $CH_2CONHCH_3$ | |
| 726 | CH | $CF_3$ | O | $CH_2CH(OH)$—$CH_2OH$ | |
| 727 | CH | $CF_3$ | O | $CH_2COCH_3$ | |
| 728 | CH | $CF_3$ | O | $COCH_3$ | |
| 729 | CH | $CF_3$ | O | $CH_2OC_6H_5$ | |
| 730 | CH | $CF_3$ | O | $COC_6H_5$ | |
| 731 | CH | $CF_3$ | O | $CF_2CH_3$ | |
| 732 | CH | $CF_3$ | O | $CH_2CN$ | |
| 733 | CH | $CF_3$ | O | $CH_2CH$(—O—)$CH_2$ | |
| 734 | CH | $CF_3$ | O | $CH_2(4\text{-}OCH_3)$—$C_6H_5$ | |
| 735 | CH | $CF_3$ | O | $CH_2CH(OH)CH_2S$—$C_6H_5$ | |
| 736 | CH | $CF_3$ | O | $CH{=}CF_2$ | |
| 737 | CH | $CF_3$ | O | $CCl{=}CHCl$ | |
| 738 | CH | $CF_3$ | O | 2-Pyridyl | |
| 739 | CH | $CF_3$ | O | $OC_6H_5$ | |
| 740 | CH | $CF_3$ | O | OH | |
| 741 | CH | $CF_3$ | O | $OCH_3$ | |
| 742 | CH | $CF_3$ | O | $OCH_2CH_3$ | |

TABLE 2-continued

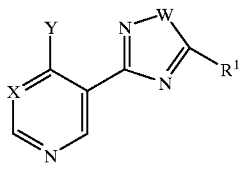

| No. | X | Y | W | $R^1$ | m.p. [° C.] |
|---|---|---|---|---|---|
| 743 | CH | $CF_3$ | O | $OCHF_2$ | |
| 744 | CH | $CF_3$ | O | $OCH_2C_6H_5$ | |
| 745 | CH | $CF_3$ | O | $SCH_3$ | |
| 746 | CH | $CF_3$ | O | $SC_6H_5$ | |
| 747 | CH | $CF_3$ | O | $NH_2$ | |
| 748 | CH | $CF_3$ | O | $NHCH_3$ | |
| 749 | CH | $CF_3$ | O | $NHCH_2CH_3$ | |
| 750 | CH | $CF_3$ | O | $N(CH_2CH_3)_2$ | |
| 751 | CH | $CF_3$ | O | $N(CH_2CN)_2$ | |
| 752 | CH | $CF_3$ | O | $N(CH_3)_2$ | |
| 753 | CH | $CF_3$ | O | $NHCOCH_3$ | |
| 754 | CH | $CF_3$ | O | $NHCOCH_2CH_3$ | |
| 755 | CH | $CF_3$ | O | $OSO_2CH_3$ | |
| 756 | CH | $CF_3$ | O | $SOCH_2(4\text{-}Br)$—$C_6H_4$ | |
| 757 | CH | $CF_3$ | O | $N(CH_3)COOCH_2$—$C_6H_5$ | |
| 758 | N | $CF_3$ | O | $CH_3$ | |
| 759 | N | $CF_3$ | O | $CH_2CH_3$ | |
| 760 | N | $CF_3$ | O | $(CH_2)_2CH_3$ | |
| 761 | N | $CF_3$ | O | $CH(CH_3)_2$ | |
| 762 | N | $CF_3$ | O | $(CH_2)_3CH_3$ | |
| 763 | N | $CF_3$ | O | $CH_2CH(CH_3)_2$ | |
| 764 | N | $CF_3$ | O | $C(CH_3)_3$ | |
| 765 | N | $CF_3$ | O | $CH_2C(CH_3)_3$ | |
| 766 | N | $CF_3$ | O | cyclo-$C_5H_9$ | |
| 767 | N | $CF_3$ | O | cyclo-$C_6H_{11}$ | |
| 768 | N | $CF_3$ | O | $CH_2C{=}C(CH_3)_2$ | |
| 769 | N | $CF_3$ | O | $CH_2CH_2C{=}CH_2$ | |
| 770 | N | $CF_3$ | O | $CH_2CH{=}CH_2$ | |
| 771 | N | $CF_3$ | O | $(CH_2)_5CH{=}CH_2$ | |
| 772 | N | $CF_3$ | O | $CH_2C{\equiv}CH$ | |
| 773 | N | $CF_3$ | O | $CH_2C{\equiv}CCH_2CH_3$ | |
| 774 | N | $CF_3$ | O | $CHFCF_3$ | |
| 775 | N | $CF_3$ | O | $COOCH_2CH_3$ | |
| 776 | N | $CF_3$ | O | $CH_2CH_2OH$ | |
| 777 | N | $CF_3$ | O | $CH_2CH_2OCH_3$ | |
| 778 | N | $CF_3$ | O | $CH_2COOC(CH_3)_3$ | |
| 779 | N | $CF_3$ | O | $CH_2SC_6H_5$ | |
| 780 | N | $CF_3$ | O | $CH_2CONHCH_3$ | |
| 781 | N | $CF_3$ | O | $CH_2CH(OH)$—$CH_2OH$ | |
| 782 | N | $CF_3$ | O | CHO | |
| 783 | N | $CF_3$ | O | $COCH_3$ | |
| 784 | N | $CF_3$ | O | $CH_2OC_6H_5$ | |
| 785 | N | $CF_3$ | O | $COC_6H_5$ | |
| 786 | N | $CF_3$ | O | $CF_2CH_3$ | |
| 787 | N | $CF_3$ | O | $CH_2CN$ | |
| 788 | N | $CF_3$ | O | $CH_2CH_2CN$ | |
| 789 | N | $CF_3$ | O | $CH{=}CF_2$ | |
| 790 | N | $CF_3$ | O | 2-Furyl | |
| 791 | N | $CF_3$ | O | OH | |
| 792 | N | $CF_3$ | O | $OCH_3$ | |
| 793 | N | $CF_3$ | O | $OCH_2CH_3$ | |
| 794 | N | $CF_3$ | O | $OCHF_2$ | |
| 795 | N | $CF_3$ | O | $OCH_2C_6H_5$ | |
| 796 | N | $CF_3$ | O | $NH_2$ | |
| 797 | N | $CF_3$ | O | $NHCH_3$ | |
| 798 | N | $CF_3$ | O | $NHCH_2CH_3$ | |
| 799 | N | $CF_3$ | O | $N(CH_2CH_3)_2$ | |
| 800 | N | $CF_3$ | O | $N(CH_2CN)_2$ | |
| 801 | N | $CF_3$ | O | $N(CH_3)_2$ | |
| 802 | N | $CF_3$ | O | $NHCOCH_3$ | |
| 803 | N | $CF_3$ | O | $NHCOCH_2CH_3$ | |
| 804 | N | $CF_3$ | O | $OSO_2CH_3$ | |
| 805 | CH | $CF_3$ | S | $CH_3$ | |
| 806 | CH | $CF_3$ | S | $CH_2CH_3$ | |
| 807 | CH | $CF_3$ | S | $(CH_2)_2CH_3$ | |

TABLE 2-continued

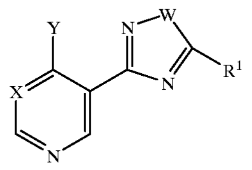

| No. | X | Y | W | $R^1$ | m.p. [° C.] |
|---|---|---|---|---|---|
| 808 | CH | $CF_3$ | S | CHO | |
| 809 | CH | $CF_3$ | S | $CHFCF_3$ | |
| 810 | CH | $CF_3$ | S | $CH_2C{\equiv}CH$ | |
| 811 | CH | $CF_3$ | S | $COOCH_2CH_3$ | |
| 812 | CH | $CF_3$ | S | $CH_2COOC(CH_3)_3$ | |
| 813 | CH | $CF_3$ | S | $CH_2CN$ | |
| 814 | N | $CF_3$ | S | $CH_3$ | |
| 815 | N | $CF_3$ | S | $CH_2CH_3$ | |
| 816 | N | $CF_3$ | S | $(CH_2)_2CH_3$ | |
| 817 | N | $CF_3$ | S | $CHFCF_3$ | |
| 818 | N | $CF_3$ | S | $CH_2CH_2OH$ | |
| 819 | N | $CF_3$ | S | $CH_2COOC(CH_3)_3$ | |
| 820 | N | $CH_2CH_2$—Cl | O | $CH_2CH_3$ | |
| 821 | N | $CH_2CH_2$—Cl | O | $NH_2$ | |
| 822 | N | $CH_2Cl$ | O | $CH_3$ | |

TABLE 2-continued

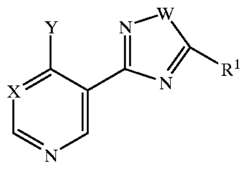

| No. | X | Y | W | $R^1$ | m.p. [° C.] |
|---|---|---|---|---|---|
| 823 | CH | $CHF_2$ | O | $CH_3$ | |
| 824 | CH | $CHF_2$ | O | $CH_2CH_3$ | |
| 825 | CH | $CHF_2$ | O | $(CH_2)_2CH_3$ | |
| 826 | CH | $CHF_2$ | O | $CH_2C{=}CH_2$ | |
| 827 | CH | $CHF_2$ | O | $C(CH_3){=}CH_2$ | |
| 828 | CH | $CHF_2$ | O | $COOCH_2CH_3$ | |
| 829 | CH | $CHF_2$ | O | $CH_2CONHCH_3$ | |
| 830 | CH | $CHF_2$ | O | $CF_2CH_3$ | |
| 831 | CH | $CHF_2$ | O | CHO | |
| 832 | CH | $CHF_2$ | O | $NH_2$ | |
| 833 | CH | $CHF_2$ | O | $NHCOCH_3$ | |
| 834 | N | $CHF_2$ | O | $CH_3$ | |
| 835 | N | $CHF_2$ | O | $CH_2CH_3$ | |
| 836 | N | $CHF_2$ | O | $CH(CH_3)(CH_2)_4$—$CH_3$ | |
| 837 | N | $CHF_2$ | O | $CH_2CH{=}CH_2$ | |
| 838 | N | $CHF_2$ | O | $COOCH_2CH_3$ | |
| 839 | N | $CHF_2$ | O | $NH_2$ | |

TABLE 3

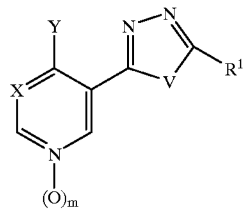

| No. | X | Y | m | V | $R^1$ | m.p. [° C.] |
|---|---|---|---|---|---|---|
| 840 | N | $(CF_2)_3CHF_2$ | 0 | O | $CH_3$ | |
| 841 | N | $(CF_2)_2CF_3$ | 0 | O | $CH_2CH_3$ | |
| 842 | N | $(CF_2)_2CF_3$ | 0 | O | $COOCH_2CH_3$ | |
| 843 | N | $(CF_2)_2CF_3$ | 0 | O | SH | |
| 844 | N | $(CF_2)_2CF_3$ | 0 | O | $SCH_3$ | |
| 845 | N | $(CF_2)_2CF_3$ | 0 | O | $SCH_2C{\equiv}CH$ | |
| 846 | N | $CF_2CF_3$ | 0 | O | $CH_3$ | |
| 847 | N | $CF_2CF_3$ | 0 | O | $CH_2CH_3$ | |
| 848 | N | $CF_3$ | 0 | O | $CH_3$ | |
| 849 | N | $CF_3$ | 0 | O | $CH_2CH_3$ | |
| 850 | N | $CF_3$ | 0 | O | $(CH_2)_2CH_3$ | |
| 851 | N | $CF_3$ | 0 | O | $CH(CH_3)_2$ | |
| 852 | N | $CF_3$ | 0 | O | $(CH_2)_3CH_3$ | |
| 853 | N | $CF_3$ | 0 | O | $CH_2CH(CH_3)_2$ | |
| 854 | N | $CF_3$ | 0 | O | $C(CH_3)_3$ | |
| 855 | N | $CF_3$ | 0 | O | $CH_2C(CH_3)_3$ | |
| 856 | N | $CF_3$ | 0 | O | Cyclo-$C_5H_9$ | |
| 857 | N | $CF_3$ | 0 | O | Cyclo-$C_6H_{11}$ | |
| 858 | N | $CF_3$ | 0 | O | $CH_2CH{=}C(CH_3)_2$ | |
| 859 | N | $CF_3$ | 0 | O | $CH_2CH_2CH{=}CH_2$ | |
| 860 | N | $CF_3$ | 0 | O | $CH_2CH{=}CH_2$ | |
| 861 | N | $CF_3$ | 0 | O | $(CH_2)_5CH{=}CH_2$ | |
| 862 | N | $CF_3$ | 0 | O | $CH_2C{\equiv}CH$ | |

TABLE 3-continued

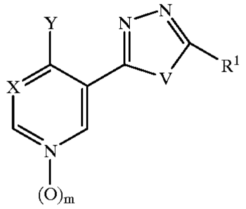

| No. | X | Y | m | V | $R^1$ | m.p. [° C.] |
|---|---|---|---|---|---|---|
| 863 | N | $CF_3$ | 0 | O | $CH_2C{\equiv}CCH_2CH_3$ | |
| 864 | N | $CF_3$ | 0 | O | $CHFCF_3$ | |
| 865 | N | $CF_3$ | 0 | O | $COOCH_2CH_3$ | |
| 866 | N | $CF_3$ | 0 | O | $CH_2CH_2OH$ | |
| 867 | N | $CF_3$ | 0 | O | $CH_2CH_2OCH_3$ | |
| 868 | N | $CF_3$ | 0 | O | $CH_2COOC(CH_3)_3$ | |
| 869 | N | $CF_3$ | 0 | O | $CH_2SPh$ | |
| 870 | N | $CF_3$ | 0 | O | $CH_2CONHCH_3$ | |
| 871 | N | $CF_3$ | 0 | O | $CH_2CH(OH)CH_2OH$ | |
| 872 | N | $CF_3$ | 0 | O | CHO | |
| 873 | N | $CF_3$ | 0 | O | $COCH_3$ | |
| 874 | N | $CF_3$ | 0 | O | $CH_2OC_6H_5$ | |
| 875 | N | $CF_3$ | 0 | O | COPh | |
| 876 | N | $CF_3$ | 0 | O | $CF_2CH_3$ | |
| 877 | N | $CF_3$ | 0 | O | $CH_2CN$ | |
| 878 | N | $CF_3$ | 0 | O | $CH_2CH_2CN$ | |
| 879 | N | $CF_3$ | 0 | O | $CH{=}CF_2$ | |
| 880 | N | $CF_3$ | 0 | O | 2-Furyl | |
| 881 | N | $CF_3$ | 0 | O | OH | |
| 882 | N | $CF_3$ | 0 | O | $OCH_3$ | |
| 883 | N | $CF_3$ | 0 | O | $OCH_2CH_3$ | |
| 884 | N | $CF_3$ | 0 | O | $OCHF_2$ | |
| 885 | N | $CF_3$ | 0 | O | $OCH_2Ph$ | |
| 886 | N | $CF_3$ | 0 | O | $NH_2$ | |
| 887 | N | $CF_3$ | 0 | O | $NHCH_3$ | |
| 888 | N | $CF_3$ | 0 | O | $NHCH_2CH_3$ | |
| 889 | N | $CF_3$ | 0 | O | $N(CH_2CH_3)_2$ | |
| 890 | N | $CF_3$ | 0 | O | $N(CH_2CN)_2$ | |
| 891 | N | $CF_3$ | 0 | O | $N(CH_3)_2$ | |
| 892 | N | $CF_3$ | 0 | O | $NHCOCH_3$ | |
| 893 | N | $CF_3$ | 0 | O | $NHCOCH_2CH_3$ | |
| 894 | N | $CF_3$ | 0 | O | $OSO_2CH_3$ | |
| 895 | N | $CH_2CH_2Cl$ | 0 | O | $CH_2CH_3$ | |
| 896 | N | $CH_2CH_2Cl$ | 0 | O | $NH_2$ | |
| 897 | N | $CH_2Cl$ | 0 | O | $CH_3$ | |
| 898 | N | $CHF_2$ | 0 | O | $CH_3$ | |
| 899 | N | $CHF_2$ | 0 | O | $CH_2CH_3$ | |
| 900 | N | $CHF_2$ | 0 | O | $CH(CH_3)(CH_2)_4CH_3$ | |
| 901 | N | $CHF_2$ | 0 | O | $CH_2CH{=}CH_2$ | |
| 902 | N | $CHF_2$ | 0 | O | $COOCH_2CH_3$ | |
| 903 | N | $CHF_2$ | 0 | O | $NH_2$ | |
| 904 | CH | $CF_3$ | 0 | O | $CH_3$ | 60–61 |
| 905 | CH | $CF_3$ | 1 | O | $CH_3$ | |
| 906 | CH | $CF_3$ | 0 | O | $CH_2CH_3$ | oil |
| 907 | CH | $CF_3$ | 1 | O | $CH_2CH_3$ | oil |
| 908 | CH | $CF_3$ | 0 | O | $(CH_2)_2CH_3$ | oil |
| 909 | CH | $CF_3$ | 1 | O | $(CH_2)_2CH_3$ | oil |
| 910 | CH | $CF_3$ | 0 | O | $CH(CH_3)_2$ | |
| 911 | CH | $CF_3$ | 1 | O | $CH(CH_3)_2$ | |
| 912 | CH | $CF_3$ | 0 | O | $(CH_2)_3CH_3$ | |
| 913 | CH | $CF_3$ | 1 | O | $(CH_2)_3CH_3$ | |
| 914 | CH | $CF_3$ | 0 | O | $CH(CH_3)CH_2CH_3$ | |
| 915 | CH | $CF_3$ | 1 | O | $CH(CH_3)CH_2CH_3$ | |
| 916 | CH | $CF_3$ | 0 | O | $CH_2CH(CH_3)_2$ | |
| 917 | CH | $CF_3$ | 1 | O | $CH_2CH(CH_3)_2$ | |
| 918 | CH | $CF_3$ | 0 | O | $C(CH_3)_3$ | |
| 919 | CH | $CF_3$ | 1 | O | $C(CH_3)_3$ | |
| 920 | CH | $CF_3$ | 0 | O | $(CH_2)_4CH_3$ | |
| 921 | CH | $CF_3$ | 1 | O | $(CH_2)_4CH_3$ | |
| 922 | CH | $CF_3$ | 0 | O | $CH(CH_3)(CH_2)_2CH_3$ | |
| 923 | CH | $CF_3$ | 0 | O | $(CH_2)_2CH(CH_3)_2$ | |
| 924 | CH | $CF_3$ | 0 | O | $CH_2C(CH_3)_3$ | |
| 925 | CH | $CF_3$ | 0 | O | cyclo-$C_5H_9$ | |
| 926 | CH | $CF_3$ | 0 | O | cyclo-$C_6H_{11}$ | |
| 927 | CH | $CF_3$ | 0 | O | $CH_2$(3-Thienyl) | oil |
| 928 | CH | $CF_3$ | 0 | O | CHO | |

TABLE 3-continued

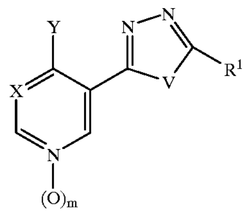

| No. | X | Y | m | V | $R^1$ | m.p. [° C.] |
|---|---|---|---|---|---|---|
| 929 | CH | $CF_3$ | 0 | O | $CH{=}CH_2$ | |
| 930 | CH | $CF_3$ | 0 | O | $CH_2Ph$ | 61–63 |
| 931 | CH | $CF_3$ | 0 | O | $CH_2CH{=}C(CH_3)_2$ | |
| 932 | CH | $CF_3$ | 0 | O | $CH_2CH{=}CH_2$ | |
| 933 | CH | $CF_3$ | 0 | O | $C(CH_3){=}CH_2$ | |
| 934 | CH | $CF_3$ | 0 | O | $(CH_2)_5C{=}CH_2$ | |
| 935 | CH | $CF_3$ | 0 | O | $C({=}CHCH_3)CH_3$ | |
| 936 | CH | $CF_3$ | 0 | O | $CH_2C{\equiv}CH$ | |
| 937 | CH | $CF_3$ | 0 | O | $CH_2CH_2C{\equiv}CH_2$ | |
| 938 | CH | $CF_3$ | 0 | O | $CH_2C{\equiv}CCH_2CH_3$ | |
| 939 | CH | $CF_3$ | 0 | O | $(CH_2)_4C{\equiv}CH$ | |
| 940 | CH | $CF_3$ | 0 | O | $CHFCF_3$ | |
| 941 | CH | $CF_3$ | 0 | O | $COOCH_2CH_3$ | |
| 942 | CH | $CF_3$ | 0 | O | $CH_2CH_2OH$ | |
| 943 | CH | $CF_3$ | 0 | O | $CH_2CH_2OCH_3$ | |
| 944 | CH | $CF_3$ | 0 | O | $CH_2COOC(CH_3)_3$ | |
| 945 | CH | $CF_3$ | 0 | O | $CH_2SPh$ | |
| 946 | CH | $CF_3$ | 0 | O | $CH_2CONHCH_3$ | |
| 947 | CH | $CF_3$ | 0 | O | $CH_2CH(OH)CH_2OH$ | |
| 948 | CH | $CF_3$ | 0 | O | $CH_2COCH_3$ | |
| 949 | CH | $CF_3$ | 0 | O | $COCH_3$ | |
| 950 | CH | $CF_3$ | 0 | O | $CH_2Oph$ | |
| 951 | CH | $CF_3$ | 0 | O | COPh | |
| 952 | CH | $CF_3$ | 0 | O | $CF_2CH_3$ | |
| 953 | CH | $CF_3$ | 0 | O | $CH_2CN$ | oil |
| 954 | CH | $CF_3$ | 0 | O | $CH_2CH(—O—)CH_2$ | |
| 955 | CH | $CF_3$ | 0 | O | $CH_2(4\text{-}OCH_3)Ph$ | |
| 956 | CH | $CF_3$ | 0 | O | $CH_2CH(OH)CH_2SPh$ | |
| 957 | CH | $CF_3$ | 0 | O | $CH{=}CF_2$ | |
| 958 | CH | $CF_3$ | 0 | O | $CCl{=}CHCl$ | |
| 959 | CH | $CF_3$ | 0 | O | Ph | 120–121 |
| 960 | CH | $CF_3$ | 0 | O | 2-Thienyl | 87–89 |
| 961 | CH | $CF_3$ | 0 | O | Oph | |
| 962 | CH | $CF_3$ | 0 | O | OH | |
| 963 | CH | $CF_3$ | 0 | O | $OCH_3$ | |
| 964 | CH | $CF_3$ | 0 | O | $OCH_2CH_3$ | |
| 965 | CH | $CF_3$ | 0 | O | $OCHF_2$ | |
| 966 | CH | $CF_3$ | 0 | O | $OCH_2Ph$ | |
| 967 | CH | $CF_3$ | 0 | O | $SCH_3$ | |
| 968 | CH | $CF_3$ | 0 | O | SPh | |
| 969 | CH | $CF_3$ | 0 | O | $NH_2$ | 190–191 |
| 970 | CH | $CF_3$ | 0 | O | $NHCH_3$ | |
| 971 | CH | $CF_3$ | 0 | O | $NHCH_2CH_3$ | |
| 972 | CH | $CF_3$ | 0 | O | $N(CH_2CH_3)_2$ | |
| 973 | CH | $CF_3$ | 0 | O | $N(CH_2CN)_2$ | |
| 974 | CH | $CF_3$ | 0 | O | $N(CH_3)_2$ | |
| 975 | CH | $CF_3$ | 0 | O | $NHCOCH_3$ | |
| 976 | CH | $CF_3$ | 0 | O | $NHCOCH_2CH_3$ | |
| 977 | CH | $CF_3$ | 0 | O | $OSO_2CH_3$ | |
| 978 | CH | $CF_3$ | 0 | O | $SOCH_2(4\text{-}Br)—C_6H_4$ | |
| 979 | CH | $CF_3$ | 0 | O | $N(CH_3)COOCH_2Ph$ | |
| 980 | CH | $CF_3$ | 0 | $NCH_3$ | $CH_3$ | |
| 981 | CH | $CF_3$ | 0 | $NCH_2CH_3$ | $CH_3$ | |
| 982 | CH | $CF_3$ | 0 | $NCH_2CH_3$ | $CH_2CH_3$ | |
| 983 | CH | $CF_3$ | 0 | $NCH_2CN$ | $CH_2CH_3$ | |
| 984 | CH | $CF_3$ | 0 | $NCH_2OCH_3$ | $NHCH_3$ | |
| 985 | CH | $CF_3$ | 0 | $NCH_2OCH_2CH_3$ | CN | |
| 986 | CH | $CF_3$ | 0 | $NCH_2CH{=}CH_2$ | $CH_3$ | |
| 987 | CH | $CF_3$ | 0 | $NCH_2CH{=}CF_2$ | $SCH_3$ | |
| 988 | CH | $CF_3$ | 0 | $NCH_2OCH_3$ | $SCH_2CH_3$ | |
| 989 | CH | $CF_3$ | 0 | $NCH_2OCH_3$ | $SCH_2Ph$ | |
| 990 | CH | $CHF_2$ | 0 | O | $CH_3$ | |
| 991 | CH | $CHF_2$ | 0 | O | $CH_2CH_3$ | |
| 992 | CH | $CHF_2$ | 0 | O | $(CH_2)_2CH_3$ | |
| 993 | CH | $CHF_2$ | 0 | O | $CH_2CH{=}CH_2$ | |
| 994 | CH | $CHF_2$ | 0 | O | $C(CH_3){=}CH_2$ | |

TABLE 3-continued

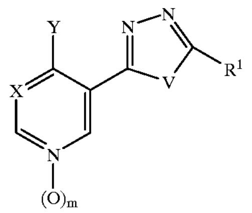

| No. | X | Y | m | V | $R^1$ | m.p. [° C.] |
|---|---|---|---|---|---|---|
| 995 | CH | $CHF_2$ | 0 | O | $COOCH_2CH_3$ | |
| 996 | CH | $CHF_2$ | 0 | O | $CH_2CONHCH_3$ | |
| 997 | CH | $CHF_2$ | 0 | O | $CF_2CH_3$ | |
| 998 | CH | $CHF_2$ | 0 | O | CHO | |
| 999 | CH | $CHF_2$ | 0 | O | $NH_2$ | |
| 1000 | CH | $CHF_2$ | 0 | O | $NHCOCH_3$ | |
| 1001 | N | $CF_2CF_3$ | 0 | S | $CH_3$ | |
| 1002 | N | $CF_2CF_3$ | 0 | S | $CH_2CH_3$ | |
| 1003 | N | $CF_2CF_3$ | 0 | S | $(CH_2)_2CH_3$ | |
| 1004 | N | $CF_3$ | 0 | S | $CH_3$ | |
| 1005 | N | $CF_3$ | 0 | S | $CH_2CH_3$ | |
| 1006 | N | $CF_3$ | 0 | S | $(CH_2)_2CH_3$ | |
| 1007 | N | $CF_3$ | 0 | S | $CHFCF_3$ | |
| 1008 | N | $CF_3$ | 0 | S | $CH_2CH_2OH$ | |
| 1009 | N | $CF_3$ | 0 | S | $CH_2COOC(CH_3)_3$ | |
| 1010 | CH | $CF_3$ | 0 | S | $CH_3$ | |
| 1011 | CH | $CF_3$ | 0 | S | $CH_2CH_3$ | |
| 1012 | CH | $CF_3$ | 0 | S | $(CH_2)_2CH_3$ | |
| 1013 | CH | $CF_3$ | 0 | S | CHO | |
| 1014 | CH | $CF_3$ | 0 | S | $CHFCF_3$ | |
| 1015 | CH | $CF_3$ | 0 | S | $CH_2C{\equiv}CH$ | |
| 1016 | CH | $CF_3$ | 0 | S | $COOCH_2CH_3$ | |
| 1017 | CH | $CF_3$ | 0 | S | $CH_2COOC(CH_3)_3$ | |
| 1018 | CH | $CF_3$ | 0 | S | $CH_2CN$ | |

TABLE 4

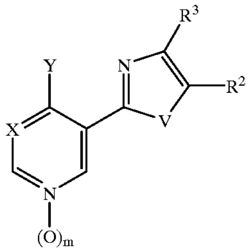

| No. | X | Y | m | V | $R^2$ | $R^3$ | m.p. [° C.] |
|---|---|---|---|---|---|---|---|
| 1019 | N | $(CF_2)_3CHF_2$ | 0 | S | H | $CH_2CH_3$ | |
| 1020 | N | $CF_2CF_2CF_3$ | 0 | S | H | $CH_2CH_3$ | |
| 1021 | N | $CF_2CF_3$ | 0 | S | H | $CH_2CH_3$ | |
| 1022 | N | $CH_2CH_2Cl$ | 0 | S | H | $CH_2CH_3$ | |
| 1023 | N | $CH_2Cl$ | 0 | S | H | $CH_2CH_3$ | |
| 1024 | N | $CF_3$ | 0 | S | $CH_2CH_3$ | $CH_2CH_3$ | |
| 1025 | N | $CF_3$ | 0 | S | $(CH_2)_2CH_3$ | H | |
| 1026 | N | $CF_3$ | 0 | S | $CH(CH_3)_2$ | H | |
| 1027 | N | $CF_3$ | 0 | S | $CH_2CH(CH_3)_2$ | H | |
| 1028 | N | $CF_3$ | 0 | S | $C(CH_3)_3$ | H | |
| 1029 | CH | $CF_3$ | 0 | S | H | $CH_3$ | oil |
| 1030 | CH | $CF_3$ | 0 | S | H | $CH_2CH_3$ | oil |
| 1031 | CH | $CF_3$ | 0 | S | H | $C(CH_3)_3$ | oil |
| 1032 | CH | $CF_3$ | 0 | S | $CH_2CH_3$ | $COOCH_2CH_3$ | |
| 1033 | CH | $CF_3$ | 0 | S | $(CH_2)_2CH_3$ | $COOCH_2CH_3$ | |
| 1034 | CH | $CF_3$ | 0 | S | $CH(CH_3)_2$ | $COOCH_2CH_3$ | |
| 1035 | CH | $CF_3$ | 0 | S | $CH(CH_3)_2$ | $CONHCH_2CH_3$ | |
| 1036 | CH | $CF_3$ | 0 | S | $CH(CH_3)_2$ | $CONHCH_2CH_3$ | |
| 1037 | CH | $CF_3$ | 0 | S | $CH(CH_3)_2$ | $CON(CH_2CH_3)_2$ | |
| 1038 | CH | $CF_3$ | 0 | S | $CH(CH_3)_2$ | CONH-cyclo-$C_3H_7$ | |
| 1039 | CH | $CF_3$ | 0 | S | $C(CH_3)_3$ | $COOCH_2CH_3$ | |

TABLE 4-continued

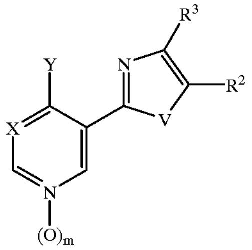

| No. | X | Y | m | V | $R^2$ | $R^3$ | m.p. [° C.] |
|---|---|---|---|---|---|---|---|
| 1040 | CH | $CF_3$ | 0 | S | H | $CONHCH_2CH_3$ | |
| 1041 | CH | $CF_3$ | 0 | S | H | $CON(CH_2CH_3)_2$ | |
| 1042 | CH | $CF_3$ | 0 | S | H | $COOCH_2CH_3$ | oil |
| 1043 | CH | $CF_3$ | 0 | S | H | $CH_2COOCH_2CH_3$ | oil |
| 1044 | CH | $CF_3$ | 0 | S | H | $CH_2CHO$ | |
| 1045 | CH | $CF_3$ | 0 | S | H | $CH_2OCH_3$ | |
| 1046 | CH | $CF_3$ | 0 | S | H | $CH_2OCH_2Ph$ | |
| 1047 | CH | $CF_3$ | 0 | S | H | H | |
| 1048 | CH | $CF_3$ | 0 | S | cyclo-$C_5H_9$ | H | |
| 1049 | CH | $CF_3$ | 0 | S | $CON(CH_3)_2$ | $CH_3$ | oil |
| 1050 | CH | $CF_3$ | 0 | S | $CH_3$ | $CH_2CH_2OH$ | |
| 1051 | CH | $CF_3$ | 0 | S | $CH_3$ | $CH_2CH_2OCH_3$ | |
| 1052 | CH | $CF_3$ | 0 | S | $CH_3$ | $CH_2CH_2OCH_2Ph$ | |
| 1053 | CH | $CF_3$ | 0 | S | $CH_3$ | $CH_2CH_2SPh$ | |
| 1054 | CH | $CF_3$ | 0 | S | $CH_3$ | $CH_3$ | oil |
| 1055 | CH | $CF_3$ | 0 | S | $CH_3$ | $CH_2CH_2CHO$ | |
| 1055 | CH | $CF_3$ | 0 | S | $CH_3$ | $CH_2CH_2CHNPh$ | |
| 1057 | CH | $CF_3$ | 0 | S | $CH_3$ | $CH_2CH_2CONH_2$ | |
| 1058 | CH | $CF_3$ | 0 | S | H | $(4\text{-}CF_3O)C_6H_4$ | 120–121 |
| 1059 | CH | $CF_3$ | 0 | S | $CH_2C{\equiv}CH$ | H | |
| 1060 | CH | $CF_3$ | 0 | S | $CH_2CH_2C{\equiv}CH$ | H | |
| 1061 | CH | $CF_3$ | 0 | S | $CH_2C{\equiv}CCH_2CH_3$ | H | |
| 1062 | CH | $CF_3$ | 0 | S | $CH_2CH{=}C(CH_3)_2$ | H | |
| 1063 | CH | $CF_3$ | 0 | S | $CH_2CH_2CH{=}CH_2$ | H | |
| 1064 | CH | $CF_3$ | 0 | S | $CH_2CH{=}CH_2$ | H | |
| 1065 | CH | $CF_3$ | 0 | S | $C(CH_3){=}CH_2$ | H | |
| 1066 | CH | $CF_3$ | 0 | S | $CHFCF_3$ | H | |
| 1067 | CH | $CF_3$ | 0 | S | $COOCH_2CH_3$ | H | |
| 1068 | CH | $CF_3$ | 0 | S | $CH_2CH_2OH$ | H | |
| 1069 | CH | $CF_3$ | 0 | S | $CH_2CH_2OCH_3$ | H | |
| 1070 | CH | $CF_3$ | 0 | S | $CH_2COOC(CH_3)_3$ | H | |
| 1071 | CH | $CF_3$ | 0 | S | $CH_2COCH_3$ | H | |
| 1072 | CH | $CF_3$ | 0 | S | COCH3 | H | |
| 1073 | CH | $CF_3$ | 0 | S | $CH_2Oph$ | H | |
| 1074 | CH | $CF_3$ | 0 | S | COPh | H | |
| 1075 | CH | $CF_3$ | 0 | S | $CO(4\text{-}Cl)\text{-}C_6H_4$ | H | |
| 1076 | CH | $CF_3$ | 0 | S | $CF_2CH_3$ | H | |
| 1077 | CH | $CF_3$ | 0 | S | $CH_2CN$ | H | |
| 1078 | CH | $CF_3$ | 0 | S | $CH_2CH_2CN$ | H | |
| 1079 | N | $CF_3$ | 0 | S | H | H | |
| 1080 | N | $CF_3$ | 0 | S | H | $CH_2CH_2CN$ | |
| 1081 | N | $CF_3$ | 0 | S | H | $CH_2CO_2C(CH_3)_3$ | |
| 1082 | N | $CF_3$ | 0 | S | H | $CH_2CHO$ | |
| 1083 | N | $CF_3$ | 0 | S | H | $CH_2CH_2OH$ | |
| 1084 | N | $CF_3$ | 0 | S | H | $CH_2CH_2OCH_3$ | |
| 1085 | N | $CF_3$ | 0 | S | cyclo-$C_5H_9$ | H | |
| 1086 | N | $CF_3$ | 0 | S | $CH_3$ | $COOCH_2CH_3$ | |
| 1087 | N | $CF_3$ | 0 | S | $CH_3$ | COOH | |
| 1088 | N | $CF_3$ | 0 | S | $CH_3$ | $CONH_2$ | |
| 1089 | N | $CF_3$ | 0 | S | $CH_3$ | $CONHCH_2CH_3$ | |
| 1090 | N | $CF_3$ | 0 | S | $CH_3$ | $CON(CH_2CH_3)_2$ | |
| 1091 | N | $CF_3$ | 0 | S | $CH_3$ | $CONHCH_3$ | |
| 1092 | N | $CF_3$ | 0 | S | $CH_3$ | $CONHCH_2CN$ | |
| 1093 | N | $CF_3$ | 0 | S | $CH_3$ | $CON(CH_2CN)_2$ | |
| 1094 | N | $CF_3$ | 0 | S | $CH_3$ | $CON(CH_3)_2$ | |
| 1095 | N | $CF_3$ | 0 | S | $CH_2C{\equiv}CH$ | $OCH_2CH_3$ | |
| 1096 | N | $CF_3$ | 0 | S | $CH_2CH_2C{\equiv}CH$ | $OCH_2CH_3$ | |
| 1097 | N | $CF_3$ | 0 | S | $CH_2C{\equiv}CCH_2CH_3$ | $OCH_2CH_3$ | |
| 1098 | N | $CF_3$ | 0 | S | $CH_2CH{=}C(CH_3)_2$ | $OCH_2CH_3$ | |
| 1099 | N | $CF_3$ | 0 | S | $CH_2CH_2CH{=}CH_2$ | $OCH_2CH_3$ | |
| 1100 | N | $CF_3$ | 0 | S | $CH_2CH{=}CH_2$ | $OCH_2CH_3$ | |
| 1101 | N | $CF_3$ | 0 | S | $C(CH_3){=}CH_2$ | $OCH_2CH_3$ | |

TABLE 4-continued

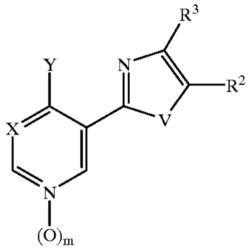

| No. | X | Y | m | V | $R^2$ | $R^3$ | m.p. [° C.] |
|---|---|---|---|---|---|---|---|
| 1102 | N | $CF_3$ | 0 | S | $CHFCF_3$ | $OCH_2CH_3$ | |
| 1103 | N | $CF_3$ | 0 | S | $COOCH_2CH_3$ | $OCH_2CH_3$ | |
| 1104 | N | $CF_3$ | 0 | S | $CH_2CH_2OH$ | $OCH_2CH_3$ | |
| 1105 | N | $CF_3$ | 0 | S | $CH_2CH_2OCH_3$ | $OCH_2CH_3$ | |
| 1106 | N | $CF_3$ | 0 | S | $CH_2COOC(CH_3)_3$ | $OCH_2CH_3$ | |
| 1107 | N | $CF_3$ | 0 | S | $CH_2COCH_3$ | H | |
| 1108 | N | $CF_3$ | 0 | S | $COCH_3$ | H | |
| 1109 | N | $CF_3$ | 0 | S | $CH_2Oph$ | H | |
| 1110 | N | $CF_3$ | 0 | S | COPh | H | |
| 1111 | N | $CF_3$ | 0 | S | CO(4-Cl)-$C_6H_4$ | H | |
| 1112 | N | $CF_3$ | 0 | S | $CF_2CH_3$ | H | |
| 1113 | N | $CF_3$ | 0 | S | $CH_2CN$ | H | |
| 1114 | N | $CF_3$ | 0 | S | $CH_2CH_2CN$ | H | |
| 1115 | CH | $CF_3$ | 0 | O | $CH_2CH_3$ | $CH_2CH_3$ | |
| 1116 | CH | $CF_3$ | 0 | O | $(CH_2)_2CH_3$ | H | |
| 1117 | CH | $CF_3$ | 0 | O | H | $CH_2CH_3$ | oil |
| 1118 | CH | $CF_3$ | 0 | O | $CH(CH_3)_2$ | $COOCH_2CH_3$ | |
| 1119 | CH | $CF_3$ | 0 | O | $CH(CH_3)_2$ | COOH | |
| 1120 | CH | $CF_3$ | 0 | O | $CH(CH_3)_2$ | $CONH_2$ | |
| 1121 | CH | $CF_3$ | 0 | O | $CH(CH_3)_2$ | $CH_3$ | |
| 1122 | CH | $CF_3$ | 0 | O | $C(CH_3)_3$ | H | |
| 1123 | CH | $CF_3$ | 0 | O | H | $CH_3$ | |
| 1124 | CH | $CF_3$ | 0 | O | H | cyclo-$C_5H_9$ | |
| 1125 | CH | $CF_3$ | 0 | O | H | $CH_2CH_2CH_3$ | |
| 1126 | CH | $CF_3$ | 0 | O | H | Ph | 103–104 |
| 1127 | CH | $CF_3$ | 0 | O | H | 2-Pyridyl | |
| 1128 | CH | $CF_3$ | 0 | O | H | 2-Furyl | |
| 1129 | CH | $CF_3$ | 0 | O | cyclo-$C_5H_9$ | H | |
| 1130 | CH | $CF_3$ | 0 | O | $CH_3$ | $COOCH_2CH_3$ | |
| 1131 | CH | $CF_3$ | 0 | O | $CH_3$ | COOH | |
| 1132 | CH | $CF_3$ | 0 | O | $CH_3$ | $CONH_2$ | |
| 1133 | CH | $CF_3$ | 0 | O | $CH_3$ | $CONHCH_2CH_3$ | |
| 1134 | CH | $CF_3$ | 0 | O | $CH_3$ | $CON(CH_2CH_3)_2$ | |
| 1135 | CH | $CF_3$ | 0 | O | $CH_3$ | $CONHCH_3$ | |
| 1136 | CH | $CF_3$ | 0 | O | $CH_3$ | $CONHCH_2CN$ | |
| 1137 | CH | $CF_3$ | 0 | O | $CH_3$ | $CON(CH_2CN)_2$ | |
| 1138 | CH | $CF_3$ | 0 | O | $CH_3$ | $CON(CH_3)_2$ | |
| 1139 | CH | $CF_3$ | 0 | O | $CH_2C{\equiv}CH$ | H | |
| 1140 | CH | $CF_3$ | 0 | O | $CH_2CH_2C{\equiv}CH$ | H | |
| 1141 | CH | $CF_3$ | 0 | O | $CH_2C{\equiv}CCH_2CH_3$ | H | |
| 1142 | CH | $CF_3$ | 0 | O | $CH_2CH{=}C(CH_3)_2$ | H | |
| 1143 | CH | $CF_3$ | 0 | O | $CH_2CH_2C{=}CH$ | H | |
| 1144 | CH | $CF_3$ | 0 | O | $CH_2CH{=}CH_2$ | H | |
| 1145 | CH | $CF_3$ | 0 | O | $C(CH_3){=}CH_2$ | H | |
| 1146 | CH | $CF_3$ | 0 | O | $CHFCF_3$ | H | |
| 1147 | CH | $CF_3$ | 0 | O | $COOCH_2CH_3$ | H | |
| 1148 | CH | $CF_3$ | 0 | O | $CH_2CH_2OH$ | H | |
| 1149 | CH | $CF_3$ | 0 | O | $CH_2CH_2OCH_3$ | H | |
| 1150 | CH | $CF_3$ | 0 | O | $CH_2COOC(CH_3)_3$ H | | |
| 1151 | CH | $CF_3$ | 0 | O | $CH_2COCH_3$ | H | |
| 1152 | CH | $CF_3$ | 0 | O | $COCH_3$ | H | |
| 1153 | CH | $CF_3$ | 0 | O | $CH_2OPh$ | H | |
| 1154 | CH | $CF_3$ | 0 | O | COPh | H | |
| 1155 | CH | $CF_3$ | 0 | O | CO(4-Cl)-$C_6H_4$ | H | |
| 1156 | CH | $CF_3$ | 0 | O | $CF_2CH_3$ | H | |
| 1157 | CH | $CF_3$ | 0 | O | $CH_2CN$ | H | |
| 1158 | CH | $CF_3$ | 0 | O | $CH_2CH_2CN$ | H | |
| 1159 | N | $CF_3$ | 0 | O | $CH_2CH_3$ | $CH_2CH_3$ | |
| 1160 | N | $CF_3$ | 0 | O | $(CH_2)_2CH_3$ | H | |
| 1161 | N | $CF_3$ | 0 | O | $CH(CH_3)_2$ | $CONH_2$ | |
| 1162 | N | $CF_3$ | 0 | O | $CH(CH_3)_2$ | $CH_3$ | |
| 1163 | N | $CF_3$ | 0 | O | $C(CH_3)_3$ | H | |

TABLE 4-continued

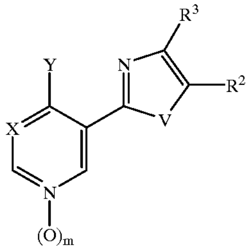

| No. | X | Y | m | V | $R^2$ | $R^3$ | m.p. [° C.] |
|---|---|---|---|---|---|---|---|
| 1164 | N | $CF_3$ | 0 | O | H | $CH_3$ | |
| 1165 | N | $CF_3$ | 0 | O | H | $CH_2CH_3$ | |
| 1166 | N | $CF_3$ | 0 | O | H | $CH_2CH_2CH_3$ | |
| 1167 | N | $CF_3$ | 0 | O | H | Ph | |
| 1168 | N | $CF_3$ | 0 | O | H | 2-Pyridyl | |
| 1169 | N | $CF_3$ | 0 | O | H | 2-Furyl | |
| 1170 | N | $CF_3$ | 0 | O | cyclo-$C_5H_9$ | H | |
| 1171 | N | $CF_3$ | 0 | O | $CH_3$ | $COOCH_2CH_3$ | |
| 1172 | N | $CF_3$ | 0 | O | $CH_3$ | COOH | |
| 1173 | N | $CF_3$ | 0 | O | $CH_3$ | $CONH_2$ | |
| 1174 | N | $CF_3$ | 0 | O | $CH_3$ | $CONHCH_2CH_3$ | |
| 1175 | N | $CF_3$ | 0 | O | $CH_3$ | $CON(CH_2CH_3)_2$ | |
| 1176 | N | $CF_3$ | 0 | O | $CH_3$ | $CONHCH_3$ | |
| 1177 | N | $CF_3$ | 0 | O | $CH_3$ | $CONHCH_2CN$ | |
| 1178 | N | $CF_3$ | 0 | O | $CH_3$ | $CON(CH_2CN)2$ | |
| 1179 | N | $CF_3$ | 0 | O | $CH_3$ | $CON(CH_3)_2$ | |
| 1180 | N | $CF_3$ | 0 | O | $CH_2C{\equiv}CH$ | H | |
| 1181 | N | $CF_3$ | 0 | O | $CH_2CH_2C{\equiv}CH$ | H | |
| 1182 | N | $CF_3$ | 0 | O | $CH_2C{\equiv}CCH_2CH_3$ | H | |
| 1183 | N | $CF_3$ | 0 | O | $CH_2CH{=}C(CH_3)_2$ | H | |
| 1184 | N | $CF_3$ | 0 | O | $CH_2CH_2CH{=}CH_2$ | H | |
| 1185 | N | $CF_3$ | 0 | O | $CH_2CH{=}CH_2$ | H | |
| 1186 | N | $CF_3$ | 0 | O | $C(CH_3){=}CH_2$ | H | |
| 1187 | N | $CF_3$ | 0 | O | $CHFCF_3$ | H | |
| 1188 | N | $CF_3$ | 0 | O | $COOCH_2CH_3$ | H | |
| 1189 | N | $CF_3$ | 0 | O | $CH_2CH_2OH$ | H | |
| 1190 | N | $CF_3$ | 0 | O | $CH_2CH_2OCH_3$ | H | |
| 1191 | N | $CF_3$ | 0 | O | $CH_2COOC(CH_3)_3$ | H | |
| 1192 | N | $CF_3$ | 0 | O | $CH_2COCH_3$ | H | |
| 1193 | N | $CF_3$ | 0 | O | $COCH_3$ | H | |
| 1194 | N | $CF_3$ | 0 | O | $CH_2Oph$ | H | |
| 1195 | N | $CF_3$ | 0 | O | COPh | H | |
| 1196 | N | $CF_3$ | 0 | O | CO(4-Cl)-$C_6H_4$ | H | |
| 1197 | N | $CF_3$ | 0 | O | $CF_2CH_3$ | H | |
| 1198 | N | $CF_3$ | 0 | O | $CH_2CN$ | H | |
| 1199 | N | $CF_3$ | 0 | O | $CH_2CH_2CN$ | H | |
| 1200 | N | $CF_3$ | 0 | O | $CH_2NHSO_2CH_3$ | $CH_3$ | |
| 1201 | N | $CF_3$ | 0 | O | $(CH_2)_2NHSO_2$—$CH_3$ | $CH_3$ | |
| 1202 | N | $CF_3$ | 0 | O | $CH_2NHSO_2CH_2$—$CH_3$ | $CH_3$ | |
| 1203 | N | $CF_3$ | 0 | O | H | $CH_2NHSO_2CH_2Ph$ | |
| 1204 | CH | $CF_3$ | 0 | O | $(CH_2)_4NHSO_2$—$CF_3$ | $CH_3$ | |
| 1205 | CH | $CF_3$ | 0 | O | $(CH_2)_2S(CH_2)_2$—$CH_3$ | $CH_2CH_2CH_3$ | |
| 1206 | CH | $CF_3$ | 0 | O | $(CH_2)_4S(CH_2)_4$—$OCH_3$ | $CH_3$ | |
| 1207 | CH | $CF_3$ | 0 | S | $CH_3$ | $(CH_2)_2S(CH_2)_2CN$ | |
| 1208 | CH | $CF_3$ | 0 | S | $CH_2NHSO_2$—$CH_2CH_3$ | $CH_3$ | |
| 1209 | CH | $CF_3$ | 0 | S | $CH_2NHSO_2$—$CH_2Ph$ | $CH_2CH_2CH_3$ | |
| 1210 | CH | $CF_3$ | 0 | S | $(CH_2)_2NHSO_2$—$CH_3$ | $CF_3$ | |
| 1211 | CH | $CF_3$ | 0 | S | H | $CH_2NHSO_2CH_3$ | |
| 1212 | CH | $CF_3$ | 0 | S | $CH(CH_3)CH_2NH$—Ph | $CF_3$ | |
| 1213 | CH | $CF_3$ | 0 | S | $(CH_2)_2S$(2-F)—$C_6H_4$ | $CH_2CH_2CH_3$ | |
| 1214 | CH | $CF_3$ | 0 | S | $(CH_2)_6NHCH_2)_6$—$OCH_3$ | $CF_3$ | |
| 1215 | CH | $CF_3$ | 0 | S | H | $(CH_2)_2$NH-(2-F)— | |

TABLE 4-continued

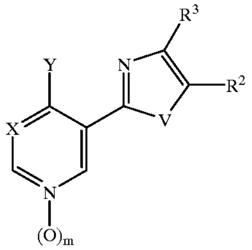

| No. | X | Y | m | V | $R^2$ | $R^3$ | m.p. [° C.] |
|---|---|---|---|---|---|---|---|
| | | | | | | $C_6H_4$ | |
| 1216 | CH | $CF_3$ | 0 | S | $(CH_2)_3NHCH_2CN$ | H | |
| 1217 | CH | $CF_3$ | 0 | S | $(CH_2)_2O(3\text{-}Cl)$—$C_6H_4$ | $CH_3$ | |
| 1218 | CH | $CF_3$ | 0 | S | $CF_3$ | $(CH_2)_6NHCH_2CF_3$ | |
| 1219 | CH | $CF_3$ | 0 | S | $CH_3$ | $(CH_2)_2O(3\text{-}CH_3)$—$C_6H_4$ | |
| 1220 | CH | $CF_3$ | 0 | O | H | $CH_2NHPh$ | |
| 1221 | CH | $CF_3$ | 0 | O | $CH_3$ | $(CH_2)_4S(2\text{-}Br)$—$C_6H_4$ | |
| 1222 | CH | $CF_3$ | 0 | O | $(CH_2)_6NH(CH_2)_2OCH_3$ | $CH_3$ | |
| 1223 | CH | $CF_3$ | 0 | O | $(CH_2)_2NH(CH_2)_4OCH_3$ | H | |
| 1224 | CH | $CF_3$ | 0 | O | $CF_3$ | $(CH_2)_3NH\text{-}(4\text{-}CN)$—$C_6H_4$ | |
| 1225 | CH | $CF_3$ | 0 | O | $(CH_2)_4NHCH_2$—$CF_3$ | $CH_3$ | |
| 1226 | CH | $CF_3$ | 0 | O | $C_2F_5$ | $(CH_2)_2O(3\text{-}CH_3)$—$C_6H_4$ | |
| 1227 | CH | $CF_3$ | 0 | O | $(CH_2)_4NHCH_2CN$ | H | |
| 1228 | CH | $CF_3$ | 0 | O | $(CH_2)_3O(4\text{-}Cl)$—$C_6H_4$ | $C_2F_5$ | |

TABLE 5

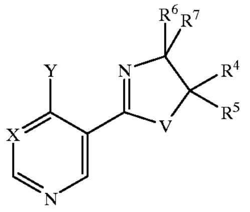

| No. | X | Y | V | $R^4$ | $R^5$ | $R^6$ | $R^7$ | m.p. [° C.] |
|---|---|---|---|---|---|---|---|---|
| 1229 | CH | $CF_3$ | O | H | H | H | H | oil |
| 1230 | CH | $CF_3$ | O | H | H | $CH_3$ | H | oil |
| 1231 | CH | $CF_3$ | O | H | H | $CH_2CH_3$ | H | oil |
| 1232 | CH | $CF_3$ | O | H | H | $CH(CH_3)_2$ | H | |
| 1233 | CH | $CF_3$ | O | H | H | $CH_2CH(CH_3)_2$ | H | |
| 1234 | CH | $CF_3$ | O | H | H | $CH(CH_3)CH_2$—$CH_3$ | H | |
| 1235 | CH | $CF_3$ | O | H | H | $CH_2OH$ | H | |
| 1236 | CH | $CF_3$ | O | H | H | $CH(OH)CH_3$ | H | |
| 1237 | CH | $CF_3$ | O | H | H | $CH_2SH$ | H | |
| 1238 | CH | $CF_3$ | O | H | H | $CH_2CH_2SCH_3$ | H | |
| 1239 | CH | $CF_3$ | O | H | H | $(CH_2)_3NH_2$ | H | |
| 1240 | CH | $CF_3$ | O | H | H | $(CH_2)_4NH_2$ | H | |
| 1241 | CH | $CF_3$ | O | H | H | $CH{=}CH_2$ | H | |
| 1242 | CH | $CF_3$ | O | H | H | $(CH_2)_2$—$COOCH_3$ | H | |
| 1243 | CH | $CF_3$ | O | H | H | $(CH_2)_2COOH$ | H | |
| 1244 | CH | $CF_3$ | O | H | H | $(CH_2)_2CONH_2$ | H | |
| 1245 | CH | $CF_3$ | S | $CH_3$ | $CH_3$ | H | H | |
| 1246 | CH | $CF_3$ | O | H | H | $CH_3$ | $CH_3$ | oil |
| 1247 | CH | $CF_3$ | O | H | H | $CH_2COOCH_3$ | H | |
| 1248 | CH | $CF_3$ | O | H | H | $CH_2COOH$ | H | |

TABLE 5-continued

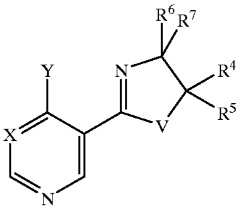

| No. | X | Y | V | $R^4$ | $R^5$ | $R^6$ | $R^7$ | m.p. [° C.] |
|---|---|---|---|---|---|---|---|---|
| 1249 | CH | $CF_3$ | O | H | H | $CH_2CONH_2$ | H | |
| 1250 | CH | $CF_3$ | O | H | H | $CH_2Ph$ | H | |
| 1251 | CH | $CF_3$ | O | H | H | $CH_2$-(4-OH)—$C_6H_4$ | H | |
| 1252 | CH | $CF_3$ | O | H | H | $CH_2$-(3-indolyl) | H | |
| 1253 | CH | $CF_3$ | O | $CH_3$ | $CH_3$ | H | H | oil |
| 1254 | CH | $CF_3$ | O | $CH_3$ | H | H | H | oil |
| 1255 | CH | $CF_3$ | O | $CH_3$ | H | H | Ph | |
| 1256 | CH | $CF_3$ | O | H | | $(CH_2)_4$ | H | |
| 1257 | CH | $CF_3$ | NH | H | | $(CH_2)_4$ | H | |
| 1258 | CH | $CF_3$ | $NCH_3$ | H | | $(CH_2)_4$ | H | |
| 1259 | CH | $CF_3$ | $NCH_2$—$C_6H_4$ | H | | $(CH_2)_4$ | H | |
| 1260 | CH | $CF_3$ | NCH—$(CH_3)_2$ | H | | $(CH_2)_4$ | H | |
| 1261 | CH | $CF_3$ | O | Ph | H | Ph | H | |
| 1262 | CH | $CF_3$ | NH | Ph | H | Ph | H | |
| 1263 | CH | $CF_3$ | $NCH_3$ | Ph | H | Ph | H | |
| 1264 | CH | $CF_3$ | $NCH_2$—$C_6H_4$ | Ph | H | Ph | H | |
| 1265 | N | $CF_3$ | O | H | H | $CH_2CH_3$ | H | oil |
| 1266 | N | $CF_3$ | O | H | H | $CH(CH_3)_2$ | H | |
| 1267 | N | $CF_3$ | O | H | H | $CH_2CH(CH_3)_2$ | H | |
| 1268 | N | $CF_3$ | O | H | H | $CH_2COOH$ | H | |
| 1269 | N | $CF_3$ | O | H | H | $CH_2COOCH_3$ | H | |
| 1270 | N | $CF_3$ | O | H | H | $CH_2CONH_2$ | H | |
| 1271 | N | $CF_3$ | O | $CH_3$ | $CH_3$ | H | H | |
| 1272 | N | $CF_3$ | O | H | $(CH_2)_4$ | | H | |
| 1273 | N | $CF_3$ | O | H | H | $CH_2CH_2SCH_3$ | H | |
| 1274 | CH | $CF_3$ | S | H | H | H | H | oil |

TABLE 6

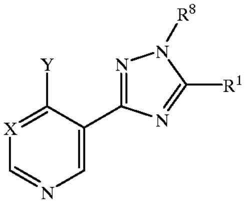

| No. | X | Y | $R^8$ | $R^1$ | m.p. [° C.] |
|---|---|---|---|---|---|
| 1275 | CH | $CF_3$ | $CH_3$ | SH | 209–210 |
| 1276 | CH | $CF_3$ | $CH_3$ | $SCH_3$ | |
| 1277 | CH | $CF_3$ | $CH_3$ | $SCH_2CH_3$ | |
| 1278 | CH | $CF_3$ | $CH_3$ | $S(CH_2)_2CH_3$ | |
| 1279 | CH | $CF_3$ | $CH_3$ | $SCH(CH_3)_2$ | |
| 1280 | CH | $CF_3$ | $CH_3$ | SPh | |
| 1281 | CH | $CF_3$ | $CH_3$ | $S(CH_2)_3CH_3$ | |
| 1282 | CH | $CF_3$ | $CH_3$ | $SCH(CH_3)CH_2CH_3$ | |
| 1283 | CH | $CF_3$ | $CH_3$ | $SCH_2CH(CH_3)_2$ | |
| 1284 | CH | $CF_3$ | $CH_3$ | OH | 119–120 |
| 1285 | CH | $CF_3$ | $CH_3$ | $OCH_3$ | |
| 1286 | CH | $CF_3$ | $CH_3$ | $OCH_2CH_3$ | |
| 1287 | CH | $CF_3$ | $CH_3$ | $OCHF_2$ | |
| 1288 | CH | $CF_3$ | $CH_3$ | $OCH_2Ph$ | |

TABLE 6-continued

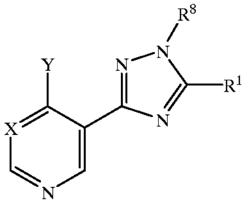

| No. | X | Y | $R^8$ | $R^1$ | m.p. [° C.] |
|---|---|---|---|---|---|
| 1289 | CH | $CF_3$ | $CH_3$ | OCONHPh | |
| 1290 | CH | $CF_3$ | $CH_3$ | OCONH-(4-F)—$C_6H_4$ | |
| 1291 | CH | $CF_3$ | $CH_3$ | OCONH-(3,5-di-Cl)—$C_6H_3$ | |
| 1292 | CH | $CF_3$ | $CH_2CN$ | $OCH_3$ | |
| 1293 | CH | $CF_3$ | $CH_2CN$ | $OCH_2CH_3$ | |
| 1294 | CH | $CF_3$ | $CH_2CN$ | $OCHF_2$ | |
| 1295 | CH | $CF_3$ | $CH_2CN$ | $OCH_2Ph$ | |
| 1296 | CH | $CF_3$ | $CH_2CN$ | OCONHPh | |
| 1297 | CH | $CF_3$ | $CH_2CN$ | OCONH-(4-F)—$C_6H_4$ | |
| 1298 | CH | $CF_3$ | $CH_2OCH_2CH_3$ | $OCH_3$ | |
| 1299 | CH | $CF_3$ | $CH_2OCH_2CH_3$ | $OCH_2CH_3$ | |
| 1300 | CH | $CF_3$ | $CH_2OCH_2CH_3$ | $OCHF_2$ | |
| 1301 | CH | $CF_3$ | $CH_2OCH_2CH_3$ | $OCH_2Ph$ | |
| 1302 | CH | $CF_3$ | $CH_2OCH_2CH_3$ | OCONHPh | |
| 1303 | CH | $CF_3$ | H | $CH_3$ | 203–204 |

TABLE 6-continued

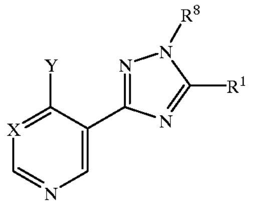

| No. | X | Y | $R^8$ | $R^1$ | m.p. [° C.] |
|---|---|---|---|---|---|
| 1304 | CH | $CF_3$ | H | $CH_2CH_3$ | 134–135 |
| 1305 | CH | $CF_3$ | H | $(CH_2)_2CH_3$ | |
| 1306 | CH | $CF_3$ | H | $CH(CH_3)_2$ | |
| 1307 | CH | $CF_3$ | H | Cyclo-$C_3H_5$ | |
| 1308 | CH | $CF_3$ | H | $(CH_2)_3CH_3$ | |
| 1309 | CH | $CF_3$ | H | $CH(CH_3)CH_2CH_3$ | |
| 1310 | CH | $CF_3$ | H | $CH_2CH(CH_3)_2$ | |
| 1311 | CH | $CF_3$ | H | $CH{=}CH_2$ | |
| 1312 | CH | $CF_3$ | H | $CH_2CH{=}C(CH_3)_2$ | |
| 1313 | CH | $CF_3$ | H | $CH_2CH_2CH{=}CH_2$ | |
| 1314 | CH | $CF_3$ | H | $CH_2CH{=}CH_2$ | |
| 1315 | CH | $CF_3$ | H | $C(CH_3){=}CH_2$ | |
| 1316 | CH | $CF_3$ | H | $CHFCF_3$ | |
| 1317 | CH | $CF_3$ | H | $COOCH_2CH_3$ | |
| 1318 | CH | $CF_3$ | H | $CH_2CH_2OH$ | |
| 1319 | CH | $CF_3$ | H | $CH_2CH_2OCH_3$ | |
| 1320 | CH | $CF_3$ | H | $CH_2COOC(CH_3)_3$ | |
| 1321 | CH | $CF_3$ | $CH_3$ | $CH_2COOC(CH_3)_3$ | |
| 1322 | CH | $CF_3$ | $CH_2CN$ | $CH_2COOC(CH_3)_3$ | |
| 1323 | CH | $CF_3$ | $CH_2OCH_2CH_3$ | $CH_2COOC(CH_3)_3$ | |
| 1324 | CH | $CF_3$ | H | $CH_2SPh$ | |
| 1325 | CH | $CF_3$ | H | $CH_2CONHCH_3$ | |
| 1326 | CH | $CF_3$ | H | $CH_2COCH_3$ | |
| 1327 | CH | $CF_3$ | H | COCH3 | |
| 1328 | CH | $CF_3$ | H | $CH_2Oph$ | |
| 1329 | CH | $CF_3$ | H | COPh | |
| 1330 | CH | $CF_3$ | H | CO(3-Cl)—$C_6H_4$ | |
| 1331 | CH | $CF_3$ | H | $CF_2CH_3$ | |
| 1332 | CH | $CF_3$ | H | $CH_2CN$ | |
| 1333 | CH | $CF_3$ | H | $CH_2CH_2CN$ | |
| 1334 | CH | $CF_3$ | H | $CH_2CH(—O—)CH_2$ | |
| 1336 | CH | $CF_3$ | H | $CH_2(4\text{-}OCH_3)Ph$ | |
| 1337 | N | $CF_3$ | $CH_3$ | SH | |
| 1338 | N | $CF_3$ | $CH_3$ | $SCH_3$ | |
| 1339 | N | $CF_3$ | $CH_3$ | $SCH_2CH_3$ | |
| 1340 | N | $CF_3$ | $CH_3$ | SPh | |
| 1341 | N | $CF_3$ | $CH_3$ | $SCH_2CH(CH_3)_2$ | |
| 1342 | N | $CF_3$ | $CH_3$ | OH | |
| 1343 | N | $CF_3$ | $CH_3$ | $OCH_3$ | |
| 1344 | N | $CF_3$ | $CH_3$ | $OCH_2CH_3$ | |
| 1345 | N | $CF_3$ | $CH_3$ | $OCH_2Ph$ | |
| 1346 | N | $CF_3$ | $CH_3$ | OCONHPh | |
| 1347 | N | $CF_3$ | $CH_2CN$ | $OCH_3$ | |
| 1348 | N | $CF_3$ | $CH_2CN$ | $OCH_2CH_3$ | |
| 1349 | N | $CF_3$ | $CH_2CN$ | $OCH_2Ph$ | |
| 1350 | N | $CF_3$ | $CH_2CN$ | OCONHPh | |
| 1351 | N | $CF_3$ | $CH_2OCH_2CH_3$ | $OCH_3$ | |
| 1352 | N | $CF_3$ | $CH_2OCH_2CH_3$ | $OCH_2Ph$ | |
| 1353 | N | $CF_3$ | $CH_2OCH_2CH_3$ | OCONHPh | |
| 1354 | N | $CF_3$ | H | $CH_3$ | |
| 1355 | N | $CF_3$ | H | $CH_2CH_3$ | |
| 1356 | N | $CF_3$ | H | $(CH_2)_2CH_3$ | |
| 1357 | N | $CF_3$ | H | $CH(CH_3)_2$ | |
| 1358 | N | $CF_3$ | H | $(CH_2)_3CH_3$ | |
| 1359 | N | $CF_3$ | H | $CH(CH_3)CH_2CH_3$ | |
| 1360 | N | $CF_3$ | H | $CH_2CH(CH_3)_2$ | |
| 1361 | N | $CF_3$ | H | $CH_2C{=}C(CH_3)_2$ | |
| 1362 | N | $CF_3$ | H | $CH_2CH{=}CH_2$ | |
| 1363 | N | $CF_3$ | H | $C(CH_3)H{=}CH_2$ | |
| 1364 | N | $CF_3$ | H | $COOCH_2CH_3$ | |
| 1365 | N | $CF_3$ | H | $CH_2CH_2OH$ | |
| 1366 | N | $CF_3$ | H | $CH_2CH_2OCH_3$ | |
| 1367 | N | $CF_3$ | H | $CH_2COOC(CH_3)_3$ | |
| 1368 | N | $CF_3$ | H | $CH_2SPh$ | |

TABLE 6-continued

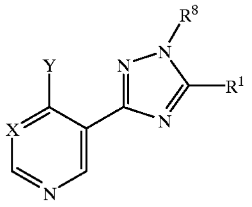

| No. | X | Y | $R^8$ | $R^1$ | m.p. [° C.] |
|---|---|---|---|---|---|
| 1369 | N | $CF_3$ | H | $CH_2CONHCH_3$ | |
| 1370 | N | $CF_3$ | H | $CH_2COCH_3$ | |
| 1371 | N | $CF_3$ | H | $COCH_3$ | |
| 1372 | N | $CF_3$ | H | $CH_2Oph$ | |
| 1373 | N | $CF_3$ | H | COPh | |
| 1374 | N | $CF_3$ | H | $CH_2CN$ | |
| 1375 | N | $CF_3$ | H | $CH_2CH_2CN$ | |
| 1376 | CH | $CF_3$ | $CH_3$ | $CH_2CH_3$ | oil |

The insecticidally active compounds used according to the invention are known and commercially available.

Deltamethrin, endosulfan, triazaphos, amitraz, piperonyl butoxide and Bacillus thuringiensis, for example, are obtainable from Hoechst Schering AgrEvo GmbH, Berlin, Germany.

The compounds are furthermore described in detail in The Pesticide Manual, 11th ed., British Crop Protection Council, Farnham 1997. Instructions for their preparation are likewise given in this publication.

Baculum viruses are described, for example, in J. Ind. Microbiol. & Biotech. 1997, 19,192.

The compounds of group (f) are described in WO-A98/57 969, with preparation processes and use examples.

These sources and the literature cited therein are expressly referred to herewith; they are incorporated into this description by reference.

The insecticides used according to the invention are usually obtainable as commercial formulations. However, they can be formulated, if appropriate, in various ways, depending on the biological and/or chemical physical parameters which prevail. Possible formulations are, for example:

wettable powders (WP), emulsifiable concentrates (EC), aqueous solutions (SL), emulsions, sprayable solutions, oil- or water-based dispersions (SC), suspoemulsions (SE), dusting agents (DP), seed-dressing products, granules in the form of microgranules, spray granules, coated granules and adsorption granules, water-dispersible granules (WG), ULV formulations, microcapsules, waxes or baits.

These individual types of formulation are known in principle and are described, for example, in:

Winnacker-Küchler, "Chemische Technologie" [Chemical Technology], Volume 7, C. Hauser Verlag Munich, 4th ed. 1986; van Falkenberg, "Pesticides Formulations", Marcel Dekker N. Y., 2nd ed. 1972–73; K. Martens, "Spray Drying Handbook", 3rd ed. 1979, G. Goodwin Ltd. London.

The formulation auxiliaries required, such as inert materials, surfactants, solvents and other additives, are likewise known and are described, for example, in:

Watkins, "Handbook of Insecticide Dust Diluents and Carriers", 2nd ed., Darland Books, Caldwell N.J.; H.v. Olphen, "Introduction to Clay Colloid Chemistry", 2nd ed., J. Wiley & Sons, N.Y.; Marsden, "Solvents Guide", 2nd ed., lnterscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-Active Ethylene Oxide Adducts], Wiss. Verlagsgesell, Stuttgart 1967; Winnacker-Küchler, "Chemische Technologie", Volume 7, C. Hauser Verlag Munich, 4th ed. 1986.

Based on these formulations, it is also possible to produce combinations with other pesticidally active compounds, fertilizers and/or growth regulators, for example in the form of a readymix or a tank mix. Wettable powders are preparations, uniformly dispersible in water, which contain, beside the active compound and in addition to a diluent or inert material, wetting agents, for example polyethoxylated alkylphenols, polyethoxylated fatty alcohols, alkyl- or alkylphenolsulfonates, and dispersing agents, for example sodium ligninsulfonate or sodium 2,2'-dinaphthylmethane-6,6'-disulfonate.

Emulsifiable concentrates are prepared by dissolving the active compound in an organic solvent, for example butanol, cyclohexanone, dimethylformamide, xylene or higher-boiling aromatics or hydrocarbons, with addition of one or more emulsifiers. As emulsifiers, the following can be used, for example: calcium salts of alkylarylsulfonates, such as Ca dodecylbenzenesulfonate, or nonionic emulsifiers such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusting agents are obtained by grinding the active compound with finely divided solid substances, for example talc, natural clays such as kaolin, bentonite, pyrophillite or diatomaceous earth. Granules can be prepared either by atomizing the active compound onto adsorptive, granulated inert material or by applying active compound concentrates onto the surface of carriers such as sand or kaolinites, or of granulated inert material, by means of adhesives, for example polyvinyl alcohol or sodium polyacrylate, or alternatively mineral oils. Suitable active compounds can also be granulated in the fashion conventional for the preparation of fertilizer lgranules, if desired as a mixture with fertilizers.

In wettable powders, the concentration of active compound is, for example, from approximately 10 to 90% by weight, the remainder to 100% by weight being composed of customary formulation components. In the case of emulsifiable concentrates, the concentration of active compound may be from approximately 5 to 80% by weight. Formulations in dust form comprise at most from 5 to 20% by weight of active compound, sprayable solutions from about 2 to 20% by weight. In the case of granules, the content of active compound depends partly on whether the active compound is in liquid or solid form and on which granulation auxiliaries, fillers, etc. are being used.

In addition, the abovementioned formulations of active compound comprise, if appropriate, the tackifiers, wetting agents, dispersants, emulsifiers, penetrants, solvents, fillers or carriers which are customary in each case.

The concentrates, which are in the commercially customary form, are if appropriate diluted in the customary manner for their use, for example using water in the case of wettable powders, emulsifiable concentrates, dispersions and some microgranules. Dust and granule preparations, and also sprayable solutions, are normally not diluted any further with other inert substances before being used.

The application rate required varies with the external conditions, such as temperature and humidity among others. It can fluctuate within wide limits, for example between 0.1 g/ha and 1.0 kg/ha or more of active compound, but is preferably between 0.1 g/ha and 0.3 kg/ha. Owing to the synergistic effects between Bt cotton and insecticide, particular preference is given to application rates of from 0.5 to 50 g/ha.

For pyrethroids (b), application rates of from 0.1 to 10 g/ha are preferred and particular preference is given to application rates of from 0.1 to 6.0 g/ha.

The active compounds according to the invention may be present in their commercially customary formulations, and in the application forms prepared from these formulations, as mixtures with other active compounds, such as insecticides, attractants, sterilants, acaricides, nematicides, fungicides, growth regulators or herbicides.

Other preferred co-components for mixtures are 1. from the group of phosphorus compounds azamethiphos, azinphos-ethyl-, azinphosmethyl, bromophos, bromophosiethyl, cadusafos (F67825), chlorethoxyphos, chlorfenvinphos, chlormephos, chlorpyrifos-methyl, demeton, demeton-S-methyl, demeton-S-methyl sulfone, dialifos, diazinon, dichlorvos, dicrotophos, dimethoate, disulfoton, EPN, ethion, ethoprophos, etrimfos, famphur, fenamiphos, fenitriothion, fensulfothion, fenthion, fonofos, formothion, fosthiazate (ASC-66824), isozophos, isothioate, isoxathion, methacrifos, methidathion, salithion, mevinphos, naled, omethoate, oxydemeton-methyl, phenthoate, phorate, phosalone, phosfolan, phosphocarb (BAS-301), phosmet, phosphamidon, phoxim, pirimiphos, primiphos-ethyl, pirimiphos-methyl, propaphos, proetamphos, prothiofos, pyraclofos, pyridapenthion, quinalphos, sulprofos, temephos, terbufos, tebupirimfos, tetrachlorvinphos, thiometon, triazophos, trichlorphon, vamidothion;
2. from the group of carbamates alanycarb, 2-sec-butylphenyl methylcarbamate (BPMC), carbosulfan, cloethocarb, benfuracarb, ethiofencarb, furathiocarb, HCN-801, isoprocarb, methomyl, 5-methyl-m-cumenyl butyryl(methyl)carbamate, oxamyl, propoxur, thiodicarb, thiofanox, 1-methylthio(ethylideneamino) N-methyl-N-(morpholinothio)carbamate (UC 51717), triazamate;
3. from the group of carboxylic acid esters acrinathrin, allethrin, alphametrin, 5-benzyl-3-fuiylmethyl (E)-(1R)-cis, 2,2-di-methyl-3-(2-oxothiolan-3-ylidenemethyl) cyclopropanecarboxylate, beta-cyfluthrin, beta-cypermethrin, bioallethrin, bioallethrin ((S)-cyclopentyl isomer), bioresmethrin, biphenthrin, (RS)-1-cyario-1-(6-phenoxy-2-pyridyl)-methyl (1RS)-trans-3-(4-tert-butylphenyl)-2,2-dirnethylcyclopropane-carboxylate (NCI 85193), cycloprothrin, cythithrin, cyphenothrin, empenthrin, esfenvalerate, fenfluthrin, flucythrinate, flumethrin, fluvalinate (D isomer), imiprothrin (S-41311), pgrmethrin, phenothrin ((R) isomer), prallethrin, pyrethrins (naturally occurring products), resmethrin, tefluthrin, tetramethrin, theta-cypermethrin (TD-2344), transfluthrin, zeta-cypermethrin (F-56701);
4. from the group of amidines chlordimeform;
5. from the group of tin compounds cyhexatin;
6. others ABG-9008, acetamiprid, *Anagrapha falcitera*, AKD-1022, AKD-3059, ANS-118, *Bacillus thuringiensis, Beauveria bassianeai*, bensultap, bifenazate (D-2341), binapacryl, BJL-932, bromopropylates, BTG-504, BTG-505, buprofezin, camphechlor, cartap, chlorobenzilates, chlorfluazuron, 2-(4-chlorophenyl)-4,5-diphenylthiophene (UBI-T 930), chlorfentezines, chromafenozides, (ANS-118), CG-216, CG-217, CG-234, A-184699, (2-naphthylmethyl) cyclopropanecarboxylate (Ro12-0470), cyromazin, diacloden (thiamethoxam), ethyl N-(3,5-dichloro-4-(1,1,2,3,3,3-hexafluoro-1-propyloxy)phenyl)carbamoyl)-2-chlorobenzocarboximidate, DDT, dicofol, diflubenzuron, N-(2,3-dihydro-3-methyl-1,3-thiazol-2-ylidene)-2,4-xylidene, dinobuton, dinocap, diofenolan, DPX-062, emamcetinbenzoates (MK-244), endosulfan, ethiproles, (sulfethiproles), ethofenprox, etoxazoles (YI-5301), fenoxycarb, fluazuron, flumites, (flufenzines, SZI-121), 2-fluoro-5-(4-(4-ethoxyphenyl)4-methyl-1-pentyl) diphenyl ether (MTI 800), granulosis and nuclear polyhedrosis viruses, fenpyroximates, fenthiocarb, flubenzimines, flucycloxuron, flufenoxuron, fluferiprox (ICI-A5683), fluproxyfen, gamma-HCH, halofenocides (RH-0345), halofenprox (MTI-732), hexaflumuron (DE-473), hexythiazox, HOI-9004, hydramethylnon (AC 217300), lufenuron, indoxacarb (DPX-MP062), kanemites (AKD-2023), M-020, MIT446, ivermectin, M-020, methoxyfenocides (Intrepid, RH-2485), milbemectin, NC-196, neemgard, nitenpyram (TI-304), 2-nitromethyl-4,5-dihydro-6H-thiazine (DS 52618), 2-nitromethyl-3,4-dihydrothiazole (SD 35651), 2-nitromethylene-1,2-thiazinan-3-ylcarbamaldehyde (WL 108477), pyriproxyfen (S-71639), NC-196, NC-1111, NNI-9768, novaluron (MCW-275), OK-9701, OK-9601, OK-9602, propargites, pymethrozines, pyridaben, pyrimidifen (SU-8801), RH-0345, RH-2485, RYI-210, S-1283, S-1833, SB7242, SI-8601, silafluofen, silomadines (CG-177), SU-9118, tebufenpyrad (MK-239), teflubenzuron, tetradifon, tetrasul, thiacloprid, thiocyclam, TI-435, tolfenpyrad (OMI-88), triflumuron, verbutin, vertalec (Mykotal), YI-5301.

The active compound content of the use forms prepared from the commercial formulations can be from 0.00000001 to 95% by weight, preferably between 0.00001 and 1% by weight, of active compound.

Owing to the synergistic effects with the Bt cotton plants and with one another, in particular mixtures of the active compounds used according to the invention can be employed in more dilute formulations.

Formulations of mixtures of pyrothroids and organophosphorus compounds contain correspondingly, for example, preferably from 0.05 to 0.01% by weight of pyrethroid and from 0.25 to 0.20% by weight of organophosphorus compound, particularly preferably from 0.01 to 0.001% by weight of pyrethroid and from 0.2 to 0.1% by weight of organophosphorus compound.

For mixtures of pyrethroids and endosulfan, preference is given to a ratio of from 0.05 to 0.01% by weight of pyrethroid to from 0.7 to 0.2% by weight of endosulfan, and particular preference is given to from 0.01 to 0.001% by weight of pyrethroid and from 0.35 to 0.2% by weight of endosulfan.

For mixtures of pyrethroids and *Bacillus thuringiensis* Bt, the values given above for pyrethroids apply, and the Bt proportion is preferably from 0.01 to 0.001, particularly preferably from 0.005 to 0.001, % by weight.

Mixtures of endosulfan and amitraz preferably contain from 0.35 to 0.2% by weight of endosulfan and from 0.6 to 0.2% by weight of amitraz.

In their commercial formulations, the active compounds used according to the invention can also be employed in combination with other fungicides which are known from the literature.

Suitable fungicides which are known from the literature are, for example, the following products:

aldimorph, andoprim, anilazine, azoxystrobin, azaconazole, BAS 450F, benalaxyl, benodanil, benomyl, bethoxazin, binapacyl, bion (CGA-245704), bitertanol, bromuconazole, buthiobate, captafol, captan, carbendazim, carboxin, carpropamides, CGA 173506, cymoxanil, cyproconazoles, cyprodinil, cyprofuram, diflumetorim, dichlofluanid, dichlomezin, diclobutrazol, diclocymet (S-2900), diclomezine, diethofencarb, difenconazole (CGA 169374), difluconazole, dimethirimol, dimethomorph, diniconazole, dinocap, dithianon, dodemorph, dodine, edifenfos, epoxiconazole, ethirimol, etridiazol, famoxadone, (DPX-JE874), fenarimol, fenazaquin, fenbuconazole, fenfuram, fenhexamid, fenpiclonil, fenpropidin, fenpropimorph, fentin acetates, fentin hydroxides, ferimzone (TF164), fluazinam, fluobenzimine, fludioxonil, flumetover (RPA403397), fluquinconazole, fluorimide, flusilazole, flusulfamide, flutolanil, flutriafol, folpet, fosetylaluminum, fuberidazole, furalaxyl, furconazole, furametpyr (S-82658), furmecyclox, guazatine, hexaconazole, imazalil, imibenconazole, ipconazole, iprobenfos, iprodione, isoprothiolane, KNF 317, kresoximemethyl (BAS49OF), copper compounds such as Cu oxychloride, oxime-Cu, Cu oxides, mancozeb, maneb, mepanipyrim (KIF 3535), mepronil, metalaxyl, metalaxyl-M (CGA-329351), metconazole, methasulfocarb, methfuroxam, metominofen (SSF-126), mentominostrobin (fenominostrobin, SSF-126), MON 24000, MON6550, MON41100, myclobutanil, nabam, nitrothalidopropyl, nuarimol, ofurace, OK-9601, OK-9603, oxadixyl, oxycarboxin, paclobutrazole, penconazole, pencycuron, PP 969, polyoxins, probenazole, propineb, prochloraz, procymidon, propamocarb, propiconazole, prothiocarb, pyracarbolid, pyrazophos, pyrifenox, pyrimethanil, pyroquilon, quinoxyfen (DE-795), rabenzazole, RH-7592, RH-7281, sulfur, spiroxamine, SSF-109, tebuconazole, tetraconazole, TTF 167, thiabendazole, thicyofen, thifluzamides (RH-130753), thiofanatemethyl, thiram, TM402, tolclofos-methyl, tolyfluanid, triadimefon, triadimenol, triazoxide, trichoderma, harzianum(DHF-471), tricyclazole, tridemorph, triflumizol, triforine, triflumizoles, (UCC-A815), triticonazoles, uniconazole, validamycin, vinchlozoline, XRD 563, zineb, sodium dodecylsulfonates, sodium dodecylsulfate, sodium C13–C15-alcohol ether sulfonate, sodium cetostearyl phosphate ester, dioctyl sodium sulfosuccinate, sodium isopropyl naphthalenesulfonate, sodium methylenebisnaphthalene sulfonate, cetyl-trimethyl-ammonium chloride, salts of long-chain primary, secondary or tertiary amines, alkylpropyleneamines, laurylpyrimidinium bromide, ethoxylated uaternized fatty amines, alkyldimethylbenzylammonium chloride and 1-ydroxyethyl-2-alkylimidazoline.

The abovementioned co-components are known active compounds, most of which are described in C. D. S. Tomlin, S. B. Walker, The Pesticide Manual, 11th edition (1997), British Crop Protection Council. The content of active compound of the use forms prepared from the commercial formulations can vary within wide ranges; the active compound concentration of the use forms can be from 0.0001 to 95% by weight of active compound, and is preferably between 0.0001 and 1% by weight. Such mixtures contain, for example, from 0.05 to 0.01% by weight of a pyrethroid and from 0.5 to 2% by weight of a fungicide, such as pyrazofos or prochloraz. The application is carried out in a customary manner adapted to the use forms.

The content of active compound of the use forms prepared from the commercial formulations can be from 0.00000001 to 95% by weight of active compound and is preferably between 0.00001 and 1% by weight.

In a preferred variant of the process according to the invention, the insecticidally active compound and a fungicide are applied together.

Application is carried out in a customary manner adapted to the use forms.

The process according to the invention is preferably suitable for application in the first (L1) larval stage, but preference is likewise given to application in later (L2 and/or L3) larval stages and/or in adult insects, in particular when controlling Lepidoptera.

For the purpose of the invention, the term "Bt cotton" is to be understood as cotton plants or crops which are genetically modified in such a way that they contain and express one or more genes from *Bacillus thuringiensis* which encode crystal proteins from the Cry family, see, for example, D. L. Prieto-Sansónor et al., J. Ind. Microbiol. & Biotechn. 1997, 19, 202 and 1997 BCPL Symposium Proceedings No. 68, 83–100).

Preference is given to genes encoding the proteins Cry1Aa, Cry1Ad, Cry1Ab, Cry1Ae, Cry1Ac, Cry1Fa, Cry1Fb, Cry1Ga, Cry1Gb, Cry1Da, Cry1Db, Cry1Ha, Cry1Hb, Cry1Ca, Cry1Cb, Cry1Ea, Cry1Eb, Cry1Ja, Cry1Jb, Cry1Bb, Cry1Bc, Cry1Bd, Cry1Ba, Cry11Ka, Cry11a, Cry1b, Cry7Aa, Cry7Ab, Cry9Ca, Cry9Da, Cry9Ba, Cry9Aa, Cry8Aa, Cry8Ba, Cry8Ca, Cry3Aa, Cry3Ca, Cry3Ba, Cry3Bb, Cry4Aa, Cry4Ba, Cry1OAa, Cry19Aa, Cry19Ba, Cry16Aa, Cry17Aa, Cry5Ab, Cry5Ba, Cry12Aa, Cry13Aa, Cry14Aa, Cry15Aa, Cry2Aa, Cry2Ab, Cry2Ac, Cry18Aa, Cry11Aa, Cry11Ba, Cyt1Aa, Cyt1Ab, Cyt1Ba, Cyt2Aa, Cyt2Ba, Cry6Aa, Cry6Ba.

Particular preference is given to Cry3Ca, Cryl Ab, Cry7Aa, Cry9C and CrylDa.

Likewise, particular preference is given to CrylAa, CrylAb, CrylAc, CrylB, CrylC, Cry2A, Cry3, Cry3A, Cry3C,Cry5 and Cry9C.

Very particular preference is given to the subfamilies Cryl and Cry9, in particular to Cry lA, CrylC, CrylF, and Cry9C.

Preference is furthermore given to using plants containing genes for a plurality of Bt proteins.

In addition to the expression of toxins from *Bacillus thuringiensis* (Bt) for insect resistance, the transgenic crop plants may also have other transgenic properties, for example further insect resistances (for example by expression of a protease or peptidase inhibitor, cf. WO-A-95/35031), herbicide resistances (for example against glufosinates or glyphosates by expression of the pat or bar gene) or else resistance against nematodes, fungi or viruses (for example by expression of a glucanase, chitinase), or may also be genetically modified in their metabolic properties, resulting in a qualitative and/or quantitative change of ingredients (for example by modification of the energy, carbohydrate, fatty acid or nitrogen metabolism or by metabolite streams which influence these).

Preference is given, for example, to Bt cotton plants which additionally have glufosinate or glyphosate resistance.

Bt cotton is known and, including methods for its preparation, described in idetail, for example, in U.S. Pat. No. 5,322,938; Prietro-Samsonór et al., J. Ind. Microbiol. & Biotechn. 1997, 19, 202, and H. Agaisse and D. Lereclus, J. Bacteriol. 1996, 177, 6027.

Bt cotton is furthermore commercially available in different varieties, for example under the name NuCOTN® from Deltapine (USA).

For the method according to the invention, preference is given to the following types of Bt cotton: NuCOTN33® and NuCOTN33B®).

Routes for preparing transgenic plants which, in comparison to naturally occurring plants, have modified properties, consist, for example, in the use of genetic engineering process (see, for example, Willmitzer L., 1993, Transgenic plants. In: Biotechnology, A Multivolume Comprehensive Treatise, Rehm et al. (eds.) Vol.2, 627–659, VCH Weinheim, Germany; D'Halluin et al., 1992, Biotechnology 10, 309–314, McCormick et al., Plant Cell Reports,1986, 5, 81–84; EP-A-0221044 and EP-A-0131624).

What is described is, for example, the preparation of genetically modified plants with respect to modifications of the hydrocarbon metabolism of the plant (for example WO 94/28146, WO 92/11376, WO 92/14827, WO 91/19806), resistances against certain herbicides, for example of the glufosinate type (cf., for example EP-A-0242236, EP-A-242246) or glyphosate type (for example WO 92/00377).

Numerous techniques of molecular biology which allow the preparation of novel transgenic plants having modified properties are known to the person skilled in the art; see, for example, Sambrook et al., 1989, Molecular Cloning, A Laboratory Manual, 2nd Ed. Cold Spring Harbor Laboratory Press, Cold Spring Harbor, N.Y.; or Winnacker, Gene und Kione [Genes and clones], VCH Weinheim 2nd Edition, 1996 or Christou, Trends in Plant Science 1 (1996) 423–431).

In order to carry out such genetic manipulations, it is possible to introduce suitable nucleic acid molecules into plants or plant cells, for example by using suitable vectors which allow mutagenesis or a change in the sequence to occur by recombination of DNA sequences. Using the abovementioned standard processes, it is possible, for example, to exchange bases, to remove partial sequences or to add natural or synthetic sequences. It is also possible, for example, to replace the lnaturally occurring genes completely by heterologous or synthetic genes, ipreferably under the control of a promoter which is active in plant cells ("gene replacement"). To link the DNA fragments with each other, it is possible to attach adapters or linkers to the fragments.

Plant cells having a reduced activity of a gene product can be prepared, for example, by expressing at least one appropriate antisense-RNA, a sense-RNA to achieve a cosuppression effect, or by expressing at least one appropriately constructed ribozyme which specifically cleaves transcripts of the abovementioned gene product.

To this end, it is possible to employ both DNA molecules which comprise the entire coding sequence of the gene product including any flanking sequences that may be present, and DNA molecules which comprise only parts of the coding sequence, it being necessary for these parts to be long enough to cause an antisense effect in the cells. It is also possible to use DNA sequences which have a high degree of homology to the coding sequences of a gene product but which are not entirely identical.

When expressing nucleic acid molecules in plants, the synthesized protein can be localized in any desired compartment of the plant cells. However, to achieve localization in a certain compartment, it is, for example, possible to link the coding region with DNA sequences which ensure localization in a certain compartment or at a certain point of time (at a certain stage or chemically or biologically induced) (for example transit or signal peptides, time- or site-specific promoters). Such sequences are known to the person skilled in the art (see, for example, Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

Transgenic plant cells can be regenerated to whole plants using known techniques.

In this manner, it is possible to obtain transgenic plants which have modified properties by overexpression, suppression or inhibition of homologous (i.e. natural) genes or gene sequences or by expression of heterologous (i.e. foreign) genes or gene sequences.

The process according to the invention is suitable for controlling a large number of harmful organisms which occur, in particular, in cotton, in particular insects, arachnids and helminths, very particularly preferably insects and arachnids. The abovementioned pests include:

From the order of the Acarina, for example *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., Tetranychus spp., Eotetranychus spp., Oligonychus spp. and Eutetranychus spp.

From the order of the Isopoda, for example, *Oniscus asselus, Armadium vulgar* and *Porcellio scaber.*

From the order of the Diplopoda, for example, *Blaniulus guttulatus.*

From the order of the Chilopoda for example, *Geophilus carpophagus* and Scutigera spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Peiplaneta americana, Leucophaea madeirae, Blattella germanica, Acheta domesticus*, Gryllotalpa spp., *Locusta migratoria migratorioides, Melanoplus differentialis* and *Schistocerca gregaria.*

From the order of the Isoptera, for example, Reticulitermes spp.

From the order of the Anoplura, for example, *Phylloera vastatrix*, Pemphigus spp., *Pediculus humanus corporis*, Haematopinus spp. and Linognathus spp.

From the order of the Mallophaga, for example, Trichodectes pp. and Damalinea spp.

From the order of the Thysanoptera, for example, *Hercinothrips femoralis,*

*Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae*, Myzus spp., *Phorodon humui, Rhopalosiphum padi*, Empoasca spp., *Euscelus bilobatus, Nephotettix cincticeps, Lecanium corni, Saissetia oleae, Laodelphax striatellus, Nilaparvata lugens, Aonidiella aurantii, Aspidiotus hederae*, Pseudococcus spp and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Laphygma exigua, Mamestra brassicae, Panolis flammea, Prodenia litura*, Spodoptera spp., Trichoplusia ni, *Carpocapsa pomonella*, Pieris spp., Chilo spp., *Pyrausta nubilalis, Ephestia kuehniella, Galleria mellonela, Cacoecia podana, Capua reticulana, Choristoneura fumiferana, Clysia ambiguella, Homona magnanima, Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylloides chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrynchus assimilis, Hypera postica*, Dermestes spp., Trogoderma, Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis, Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hypobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae*and *Tipula paludosa.*

From the order of the Siphonaptera, for example, *Xenopsylla cheopsis* and Ceratophyllus spp.

From the order of the Arachnida, for example, *Scorpio maurus* and *Latrodectus mactans.*

From the class of Helminthen, for example, Haemonchus, Trichostrongulus, Ostertagia, Cooperia, Chabertia, Strongyloides, Oesophagostomum, Hyostrongulus, Ancylostoma, Ascaris and Heterakis as well as Fasciola.

The method according to the invention is preferably suitable for controlling insects from the orders Homoptera, preferably *Bemisia tabaci, Trialeurodes vaporariorum, Aphis gossypii*, Myzus spp., Lepidoptera, preferably Agrotis spp., Heliothis spp., *Mamestra brassicae, Prodinia litura*, Spodoptera spp., *Trichoplusia ni*, and Coleoptera, preferably Anthonomus spp.

The method according to the invention is particularly preferably suitable for controlling insects from the class of the Lepidoptera, particularly preferably of Spodoptera, Agrotis, Heliothis, and very particularly preferably of *Spodoptera littoralis, Agrotis segetum* and *Heliothis virescens.*

Surprisingly, the method is also suitable for controlling harmful organisms which are resistant to individual classes of insecticides, such as pyrethroids, organophosphorus compounds or Bt.

The invention is illustrated in more detail by the examples, without limiting it thereby.

The contents of german patent application 198 25 333.8, whose priority is claimed by the present application, and the contents of the appended abstract, are incorporated herein specifically by way of reference; they are considered as part of the present description by way of citation:

EXAMPLE 1

*Heliothis virescens*

Seven-week-old cotton plants (common cotton, Vulkano®) and Bt cotton (NUCOTN 33B®), Delta Pine) were sprayed with the insecticides to be tested with the aid of a track sprayer (200 l/ha). After drying, plants were infected with 8 (L3) larvae of Heliothes virescens. Feeding damage and mortality were assessed after 2 and 4 days.

Test conditions: greenhouse, 23° C., 60% atmospheric humidity. All three active compounds showed a synergistic effect.

| Compound g of active | 2 d Feeding damage/mortality | | | | 4 d Feeding damage/mortality | | | |
|---|---|---|---|---|---|---|---|---|
| compound/ha | Cotton | | Bt cotton | | Cotton | | Bt cotton | |
| Control 1 | 5 | 0 | <1 | 0 | 7 | 0 | 1 | 75 |
| Control 2 | 10 | 0 | <1 | 25 | 15 | 0 | 1 | 88 |
| Thiodan (endosulfan) EC33 | | | | | | | | |
| 525 | 0 | 100 | <1 | 63 | 0 | 100 | <1 | 88 |
| 175 | 3 | 63 | <1 | 0 | 3 | 63 | <1 | 75 |
| 58 | 5 | 0 | <1 | 0 | 7 | 0 | <1 | 75 |
| 19 | 10 | 0 | <1 | 0 | 15 | 0 | <1 | 88 |
| 6.5 | 10 | 0 | <1 | 0 | 20 | 0 | 2 | 75 |
| Decis (deltamethrin) EC 2.5 | | | | | | | | |
| 10 | 0 | 75 | 0 | 75 | 0 | 100 | 0 | 100 |
| 3.3 | 0 | 75 | 0 | 75 | 0 | 100 | 0 | 100 |
| 1.1 | 2 | 75 | <1 | 75 | 2 | 100 | <1 | 88 |
| 0.37 | 3 | 13 | 1 | 37 | 7 | 50 | 1 | 100 |
| 0.12 | 12 | 0 | <1 | 37 | 12 | 25 | 1 | 88 |
| Dipel (Bt) WP 3 | | | | | | | | |
| 100 | <1 | 0 | <1 | 13 | 1 | 100 | 1 | 100 |
| 33 | 1 | 0 | <1 | 75 | 2 | 100 | <1 | 100 |
| 11 | 1 | 0 | <1 | 50 | 2 | 100 | <1 | 100 |
| 3.7 | 4 | 0 | <1 | 25 | 4 | 50 | <1 | 100 |
| 1.2 | 6 | 0 | <1 | 0 | 10 | 0 | 1 | 100 |

Decis and Dipel showed a synergistic effect.

EXAMPLE 2

*Spodoptera littoralis*

Three-month-old cotton plants (common cotton, Vulkano) and Bt cotton (NuCOTN 33B®) were sprayed with the insecticide to be tested with the aid of a track sprayer (200 l/ha). After drying, plants were infected with 10 (L3) larvae of *Spodoptera littoralis.*

Feeding damage and mortality were assessed after 2, 4 and 7 days.

Test conditions: (as for Example 1)

| Compound active | 2d Feeding damage/mortality | | | | 4d Feeding damage/mortality | | | | 7d Feeding damage/mortality | | | |
|---|---|---|---|---|---|---|---|---|---|---|---|---|
| compounds/ha | Cotton | | Bt cotton | | Cotton | | Bt cotton | | Cotton | | Bt cotton | |
| Control 1 | 8 | 10 | 8 | 0 | 15 | 10 | 12 | 0 | 20 | 10 | 35 | 0 |
| Control 2 | 10 | 20 | 10 | 0 | 12 | 20 | 15 | 0 | 20 | 20 | 50 | 0 |
| Control 3 | 6 | 20 | 10 | 0 | 15 | 20 | 10 | 0 | 20 | 20 | 45 | 0 |
| Hostathion (triazophos) EC 40 | | | | | | | | | | | | |
| 125 | 3 | 100 | 1 | 100 | 3 | 100 | 1 | 100 | 3 | 100 | 1 | 100 |
| 42 | 8 | 20 | 2 | 40 | 10 | 30 | 2 | 60 | 15 | 30 | 2 | 100 |
| 14 | 5 | 10 | 3 | 40 | 10 | 20 | 5 | 40 | 15 | 20 | 15 | 50 |
| 5 | 5 | 40 | 7 | 10 | 6 | 40 | 8 | 20 | 10 | 40 | 25 | 20 |
| 1.5 | 5 | 30 | 6 | 0 | 8 | 30 | 10 | 0 | 20 | 30 | 25 | 0 |

A synergistic effect is clearly noticeable.

EXAMPLE 3

*Spodoptera littoralis*

Six-week-old cotton plants (common cotton, Vulkano®) and Bt cotton (NuCOTN 33B®) were sprayed with the insecticide to be tested with the aid of a track sprayer (200 l/ha). After drying, plants were infected with 10 (L3) larvae of *Spodoptera littoralis.*

Feeding damage and mortality were assessed after 2, 4 and 7 days.

Test conditions: (see Example 1)

| Compound active compounds/ha | 2d Feeding damage/ mortality Cotton | | 2d Bt cotton | | 4d Feeding damage/ mortality Cotton | | 4d Bt cotton | | 7d Feeding damage/ mortality Cotton | | 7d Bt cotton | |
|---|---|---|---|---|---|---|---|---|---|---|---|---|
| Control 1 | 8 | 0 | 10 | 0 | 20 | 0 | 20 | 0 | 60 | 0 | 50 | 0 |
| Control 2 | 10 | 0 | 10 | 0 | 40 | 0 | 40 | 0 | 60 | 0 | 70 | 0 |
| Control 3 | 10 | 0 | 10 | 0 | 25 | 0 | 50 | 0 | 70 | 0 | 40 | 0 |
| Thiodan (endosulfan) EC 33 | | | | | | | | | | | | |
| 525 | 2 | 40 | 3 | 80 | 5 | 40 | 3 | 80 | 10 | 50 | 4 | 90 |
| 175 | 6 | 0 | 2 | 10 | 15 | 0 | 6 | 30 | 25 | 0 | 8 | 80 |
| 58 | 6 | 0 | 8 | 0 | 20 | 0 | 25 | 0 | 35 | 0 | 50 | 0 |
| 19 | 12 | 0 | 8 | 0 | 40 | 0 | 30 | 0 | 80 | 0 | 50 | 0 |
| 6.5 | 10 | 0 | 10 | 0 | 40 | 0 | 40 | 0 | 100 | 0 | 50 | 0 |

A synergistic effect is clearly noticeable.

EXAMPLE 4

*Spodoptera littoralis*

Seven-week-old cotton plants (common cotton, Felix®) and Bt cotton (NuCOTN 33B®) were sprayed with the insecticides to be tested with the aid of a track sprayer (200 l/ha). After drying, plants were infected with 10 (L3) larvae of *Spodoptera littoralis.*

Feeling damage and mortality were assessed after 2, 4 and 7 days.

Test conditions: (see Example 1)

| Compound active compounds/ha | 2d Feeding damage/ mortality Cotton | | 2d Bt cotton | | 4d Feeding damage/ mortality Cotton | | 4d Bt cotton | | 7d Feeding damage/ mortality Cotton | | 7d Bt cotton | |
|---|---|---|---|---|---|---|---|---|---|---|---|---|
| Control 1 | 12 | 0 | 10 | 0 | 20 | 0 | 20 | 0 | 40 | 0 | 50 | 0 |
| Control 2 | 12 | 0 | 10 | 0 | 25 | 0 | 25 | 0 | 40 | 0 | 50 | 0 |
| Control 3 | 12 | 0 | 10 | 0 | 30 | 0 | 30 | 0 | 40 | 0 | 40 | 0 |
| Brestan (fentin) WP 60 | | | | | | | | | | | | |
| 1000 | 3 | 0 | 3 | 20 | 4 | 0 | 3 | 50 | 4 | 80 | 3 | 100 |
| 300 | 8 | 0 | 10 | 0 | 10 | 20 | 10 | 20 | 10 | 70 | 12 | 80 |
| 100 | 10 | 0 | 10 | 0 | 25 | 0 | 25 | 0 | 30 | 0 | 40 | 30 |
| 30 | 10 | 0 | 10 | 0 | 30 | 0 | 20 | 0 | 50 | 0 | 40 | 0 |
| Piperonyl butoxide | | | | | | | | | | | | |
| 1500 | 10 | 0 | 10 | 0 | 20 | 20 | 25 | 20 | 50 | 20 | 30 | 50 |
| 500 | 10 | 0 | 10 | 0 | 20 | 0 | 25 | 20 | 40 | 0 | 40 | 40 |
| 166 | 10 | 0 | 10 | 0 | 25 | 0 | 25 | 0 | 50 | 0 | 35 | 20 |
| 56 | 10 | 0 | 8 | 0 | 20 | 0 | 20 | 0 | 40 | 0 | 40 | 0 |
| Vertimec (acemectin) EC 1.8 | | | | | | | | | | | | |
| 300 | 7 | 20 | 5 | 20 | 8 | 20 | 5 | 90 | 10 | 100 | 8 | 100 |
| 100 | 8 | 0 | 8 | 10 | 8 | 20 | 12 | 50 | 10 | 80 | 12 | 100 |
| 30 | 10 | 0 | 10 | 0 | 15 | 0 | 10 | 50 | 25 | 20 | 10 | 90 |
| 10 | 10 | 0 | 8 | 0 | 30 | 0 | 12 | 30 | 50 | 0 | 30 | 70 |

A synergistic effect is clearly noticeable.

EXAMPLE 5

*Spodoptera lettoralis*

Five-week-old cotton plants (common cotton, Vulkano®) and Bt cotton (NuCOTN 33B®)were sprayed with the insecticides to be tested with the aid of a track layer (200 l/ha). After drying, plants were infected with 10 (L3) larvae of *Spodoptera littoralis.*

Feeding damage and mortality were assessed after 2, 4 and 7 days.

Test conitions: (see Example 1)

| Compound active compounds/ha | 2d Feeding damage/ mortality Cotton | | Bt cotton | | 4d Feeding damage/ mortality Cotton | | Bt cotton | | 7d Feeding damage/ mortality Cotton | | Bt cotton | |
|---|---|---|---|---|---|---|---|---|---|---|---|---|
| Control | 10 | 0 | 10 | 0 | 35 | 0 | 15 | 0 | 50 | 0 | 20 | 0 |
| Decis EC 2.5 | | | | | | | | | | | | |
| 30 | 0 | 80 | 1 | 100 | 0 | 100 | 1 | 100 | 0 | 100 | 1 | 100 |
| 10 | 1 | 90 | 3 | 70 | 1 | 100 | 3 | 80 | 1 | 100 | 8 | 100 |
| 3 | 5 | 20 | 5 | 70 | 25 | 20 | 6 | 80 | 40 | 20 | 8 | 100 |
| 1 | 10 | 10 | 8 | 10 | 25 | 10 | 12 | 10 | 40 | 10 | 25 | 10 |
| Thiodan EC33 | | | | | | | | | | | | |
| 1000 | 1 | 90 | 0 | 80 | 1 | 100 | 0 | 100 | 1 | 100 | 0 | 100 |
| 300 | 4 | 40 | 0 | 80 | 5 | 40 | 0 | 80 | 8 | 40 | 0 | 100 |
| 100 | 5 | 40 | 3 | 60 | 10 | 40 | 6 | 60 | 20 | 40 | 10 | 60 |
| Decisdan EC 0.5 (5 + 350 g/l) | | | | | | | | | | | | |
| 30 + 2100 | 0 | 100 | 0 | 100 | 0 | 100 | 0 | 100 | 0 | 100 | 0 | 100 |
| 10 + 700 | 0 | 100 | 0 | 100 | 0 | 100 | 0 | 100 | 0 | 100 | 0 | 100 |
| 3 + 210 | 1 | 90 | 0 | 100 | 2 | 90 | 0 | 100 | 2 | 90 | 0 | 100 |
| 1 + 70 | 5 | 30 | 5 | 60 | 15 | 30 | 12 | 60 | 25 | 30 | 25 | 60 |
| Decisdan EC 0.5 (5 + 300 g/l) | | | | | | | | | | | | |
| 30 + 2100 | 0 | 100 | 0 | 100 | 0 | 100 | 0 | 100 | 0 | 100 | 0 | 100 |
| 10 + 700 | 0 | 100 | 0 | 80 | 0 | 100 | 0 | 100 | 0 | 100 | 0 | 100 |
| 3 + 210 | 1 | 90 | 1 | 90 | 1 | 90 | 3 | 90 | 1 | 90 | 5 | 90 |
| 1 + 70 | 5 | 50 | 3 | 60 | 10 | 50 | 8 | 60 | 25 | 50 | 15 | 60 |

Decis, Thiodan and Decisdan (5+350 g/l) showed a synergistic effect.

Example 6

*Agrotis segetum*

Eight-week-old cotton plants (common cotton, Felix®) and Bt cotton (NuCOTN 33®) were sprayed with the insecticides to be tested with the aid of a track sprayer (200 l/ha). After drying, plants were infected with 10 (L3) larvae of *Agrotis segetum.*

Feeding damage and mortality were assessed after 2, 4 and 7 days.

Test conditions: (see Example 1)

| Compound active compounds/ha | 2 d Feeding damage/mortality Cotton | | Bt cotton | | 4 d Feeding damage/mortality Cotton | | Bt cotton | |
|---|---|---|---|---|---|---|---|---|
| Control 1 | 3 | 0 | 3 | 0 | 10 | 0 | 4 | 0 |
| Control 2 | 0 | 0 | 3 | 0 | 10 | 0 | 3 | 0 |
| Piperonyl butoxide | | | | | | | | |
| 3000 | 1 | 80 | 0 | 80 | 1 | 90 | 0 | 100 |
| 1000 | 1 | 30 | 0 | 30 | 2 | 60 | 1 | 90 |
| 300 | 0 | 50 | 1 | 60 | 2 | 60 | 1 | 90 |

-continued

| Compound active compounds/ha | 2 d Feeding damage/mortality Cotton | | Bt cotton | | 4 d Feeding damage/mortality Cotton | | Bt cotton | |
|---|---|---|---|---|---|---|---|---|
| Vertimec EC (avamectin) | | | | | | | | |
| 1.8 | | | | | | | | |
| 300 | 0 | 40 | 1 | 80 | 3 | 60 | 2 | 100 |
| 100 | 0 | 50 | 1 | 90 | 1 | 80 | 1 | 90 |
| 30 | 1 | 10 | 1 | 0 | 1 | 10 | 1 | 20 |

A synergistic effect is clearly noticeable.

EXAMPLE 7

*Agrotis segetum*

Seven-week-old cotton plants (common cotton, Felix®) and Bt cotton (NUCOTN 33B®)) were sprayed with the insecticide to be tested with the aid of a track sprayer (200 l/ha). After drying, plants were infected with 10 (L3) larvae of *Agrotis segetum.*

Feeding damage and mortality were assessed after 2, 4 and 7 days.

Test conditions: (see Example 1)

| Compound active compounds/ha | 2d Feeding damage/mortality Cotton | | 2d Feeding damage/mortality Bt cotton | | 4d Feeding damage/mortality Cotton | | 4d Feeding damage/mortality Bt cotton | | 7d Feeding damage/mortality Cotton | | 7d Feeding damage/mortality Bt cotton | |
|---|---|---|---|---|---|---|---|---|---|---|---|---|
| Control 1 | 10 | 0 | 35 | 0 | 10 | 0 | 40 | 0 | 10 | 0 | 50 | 0 |
| Control 2 | 40 | 0 | 10 | 0 | 50 | 0 | 20 | 0 | 50 | 0 | 20 | 0 |
| Control 3 | 20 | 0 | 20 | 0 | 30 | 0 | 30 | 0 | 40 | 0 | 35 | 0 |
| Control 4 | 30 | 0 | 30 | 0 | 40 | 0 | 40 | 0 | 40 | 0 | 45 | 0 |
| Decis (deltamethrin) EC2.5 | | | | | | | | | | | | |
| 10 | 1 | 60 | 0 | 50 | 2 | 70 | 0 | 90 | 2 | 80 | 0 | 100 |
| 3.3 | 0 | 0 | 0 | 40 | 3 | 30 | 0 | 50 | 3 | 30 | 0 | 50 |
| 1.1 | 2 | 0 | 0 | 20 | 2 | 20 | 0 | 30 | 3 | 20 | 0 | 30 |
| 0.37 | 3 | 0 | 10 | 20 | 5 | 20 | 15 | 20 | 5 | 10 | 15 | 20 |
| 0.12 | 2 | 0 | 3 | 0 | 5 | 0 | 0 | 0 | 5 | 0 | 0 | 0 |

A synergistic effect is clearly noticeable.

What is claimed is:

1. A method for controlling harmful organisms in genetically modified cotton plants which contain a gene derived from *Bacillus thuringiensis* which encodes and expresses an insecticidally active protein, which comprises applying an insecticidally effective amount of one or more compounds from the following groups a–f to the plants, to their seeds or propagation stock and/or to the area in which they are cultivated:

a) Organophosphorus compounds: triazophos (726), monocrotophos (502), methamidophos (479), chlorpyrifos (137), parathion (551), acephate (4), profenofos (594), malathion (448), heptenophos (395);

b) Pyrethroids: tralomethrin (718), cypermethrin (183), cyhalothrin (179), lambdacyhalothrin (180), deltamethrin (204), fenvalerates (319), (alpha)-cypermethrin (183/184), cyfluthrin (176), fenpropathrin (312), etofenprox (292);

c) Carbamates: aldicarb (16), bendiocarb (56), carbaryl (106), carbofuran (109), formetanates (369), pirimicarb (583)

d) Biopesticides: *Bacillus thuringiensis* (46, 47), granuloses and nuclear polyhedrosis viruses, *Beauveria bassiana* (52), *Beauveria brogniartii* (53), baculoviruses, such as *Autographa california;* e) Others: endosulfan (270), abamectin (1), XDE-105 (754), diafenthiuron (208), fipronil (323), chlorfenapyr (123), tebufenocides (679), fenazaquin (301), imidacloprid (418), triazamates (724), fentin (317), amitraz (22), MK-242 f) 4-Haloalkyl-3heterocyclylpyridines and 4haloalkyl-5-heterocyclylpyrimidines of the formula (1), if appropriate also in the form of their salts, (I)

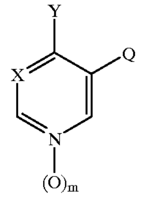

where the symbols and indices have the following meanings:

Y is halo-$C_1$–$C_6$-alkyl;

X is CH or N;

m is 0 or 1;

Q is a 5-membered heterocycic group

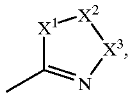

in which

| | | | | |
|---|---|---|---|---|
| a) | $X^1$ = W, | $X^2$ = $NR^a$, | $X^3$ = $CR^bR^1$ | or |
| b) | $X^1$ = $NR^a$, | $X^2$ = $CR^bR^1$, | $X^3$ = W | or |
| c) | $X^1$ = V, | $X^2$ = $CR^aR^1$, | $X^3$ = $NR^b$ | or |
| d) | $X^1$ = V, | $X^2$ = $CR^aR^2$, | $X^3$ = $CR^bR^3$ | or |
| e) | $X^1$ = V, | $X^2$ = $CR^4R^5$, | $X^3$ = $CR^6R^7$ | or |
| f) | $X^1$ = $NR^a$, | $X^2$ = $CR^bR^1$ , | $X^3$ = $Nr^8$; | |

$R^a$ and $R^b$ together are a bond

V is oxygen, sulfur or $NR^9$;

W is oxygen or sulfur;

$R^1$ is hydrogen, ($C_1$–$C_{20}$)-alkyl, ($C_2$–$C_{20}$)-alkenyl, ($C_2$–$C_{20}$)-alkynyl, ($C_3$–$C_8$)-cycloalkyl, ($C_4$–$C_8$)-cycloalkenyl, ($C_6$–$C_8$)-cycloalkynyl, where the six last-mentioned radicals are optionally substituted by one or more radicals from the group halogen, cyano, nitro, hydroxyl, —C(=W)$R^{10}$, —C(=$NOR^{10}$)$R^{10}$, —C(=$NNR^{10}_2$)$R^{10}$, —C(=W)$OR^{10}$, —C(=W)$NR^{10}_2$, —OC(=W)$R^{10}$, —OC(=W)$OR^{10}$, —$NR^{10}$C(=W)$NR^{10}$, —N[C(=W)$R^{10}$]$_2$, —$NR^{10}$C(=W)$OR^{10}$, —C(=W)$R^{10}$—$NR^{10}_2$, —C(=W)$NR^{10}$—$NR^{10}$[C(=W)$R^{10}$], —$NR^{10}$—C(=W)$NR^{10}_2$, —$NR^{10}$—$NR^{10}$C(=W)$R^{10}$, —$NR^{10}$—N[C(=W)$R^{10}$]$_2$, —N[(C=W)$R^{10}$]—$NR^{10}_2$, —$NR^{10}$—$NR^{10}$[(C=W)$R^{10}$], —$NR^{10}$—$NR^{10}$[(C=W)$WR^{10}$], —$NR^{10}$—$R^{10}$[(C=W)$NR^{10}_2$], —$NR^{10}$(C=$NR^{10}$)$R^{10}$, —$NR^{10}$(C=$NR^{10}$)$NR^{10}_2$, —O—$NR^{10}_2$, —O—$NR^{10}$(C=W)$R^{10}$, —$SO_2NR^{10}_2$, —$NR^{10}SO_2R^{10}$, —$SO_2OR^{10}$, —$OSO_2R^{10}$, $OR^{10}$, —$NR^{10}_2$, —$SR^{10}$, —$SiR^{10}_3$, —$SeR^{10}$, —$PR^{10}_2$, —$P(=W)R^{10}_2$, —$SOR^{10}$, —$SO_2R^{10}$, —$PW_2R^{10}_2$, —$PW_3R^{10}_2$, aryl and heterocyclyl, the two last-mentioned radicals optionally being substituted by one or more radicals from the group ($C_1$–$C_6$)-alkyl, ($C_2$–$C_6$)-alkenyl, ($C_2$–$C_6$)-alkynyl, ($C_3$–$C_8$)-cycloalkyl, ($C_4$–$C_8$) cycloalkenyl, ($C_6$–$C_8$)-cycloalkynyl, ($C_1$–$C_6$)-haloalkyl, ($C_2$–$C_6$)-haloalkenyl, ($C_2$–$C_6$)-haloalkynyl, halogen, —$OR^{10}$, $NR^{10}_2$, —$SR^{10}$, —$SiR^{10}_3$, —$C(=W)R^{10}$, —$C(=W)OR^{10}$, —$C(=W)NR^{10}_2$, —$SOR^{10}$, —$SO_2R^{10}$, nitro, cyano and hydroxyl, aryl, which is optionally substituted by one or more radicals from the group ($C_1$–$C_6$)-alkyl, ($C_2$–$C_6$)-alkenyl, ($C_2$–$C_6$)-alkynyl, ($C_3$–$C_8$)-cycloalkyl, ($C_4$–$C_8$)-cycloalkenyl and ($C_6$–$C_8$)-cycloalkynyl, where these six abovementioned radicals are optionally substituted by one or more radicals from the group halogen, cyano, nitro, —$C(=W)R^{10}$, —$C(=W)OR^{10}$, —$C(=W)NR^{10}_2$, —$OR^{10}$, —$NR^{10}_2$, —$SR^{10}$, —$SOR^{10}$ and —$SO_2R^{10}$, halogen, cyano, nitro, —$C(=W)R^{10}$, —$C(=NOR^{10})R^{10}$, —$C(=NNR^{10}_2)R^{10}$, —$C(=W)OR^{10}$, —$C(=W)NR^{10}_2$, —$OC(=W)R^{10}$, —$OC(=W)OR^{10}$, —$NR^{10}C(=W)R^{10}$, —$N[C(=W)R^{10}]_2$, —$NR^{10}C(=W)OR^{10}$, —$OR^{10}$, —$NR^{10}_2$, —$SR^{10}$, $SiR^{10}_3$, —$PR^{10}_2$, —$SOR^{10}$, —$SO_2R^{10}$, —$PW_2R^{10}_2$ and —$PW_3R^{10}_2$, heterocyclyl, which is optionally substituted by one or more radicals from the group ($C_1$–$C_6$)-alkyl, ($C_2$–$C_6$)-alkenyl, ($C_2$–$C_6$)-alkynyl, ($C_3$–$C_8$)-cycloalkyl, ($C_4$–$C_8$)-cycloalkenyl and ($C_6$–$C_8$)-cycloalkynyl, where the six abovementioned radicals are optionally substituted by one or more radicals from the group cyano, nitro, halogen, —$C(=W)R^{10}$, —$C(=W)OR^{10}$, —$C(=W)NR^{10}_2$, —$NR^{10}C(=W)R^{10}$, —$N[C(=W)R^{10}]_2$, —$OC(=W)R^{10}$, —$OC(=W)OR^{10}$, —$OR^{10}$, —$NR^{10}_2$, —$SR^{10}$, —$SOR^{10}$ and —$SO_2R^{10}$, halogen, cyano, nitro, —$C(=W)R^{10}$, $C(=W)OR^{10}$, —$C(=W)NR^{10}_2$, —$OC(=W)R^{10}$, —$OR^{10}$, —$NR^{10}_2$, —$SR^{10}$, —$SOR^{10}$ and —$SO_2R^{10}$, —$OR^{10}$, —$NR^{10}_2$, —$SR^{10}$, —$SOR^{10}$, —$SO_2R^{10}$, —$C(=W)R^{10}$, —$C(=NOR^{10})^{10}$, —$C(=NNR^{10}_2)R^{10}$, —$C(=W)OR^{10}$, —$C(=W)NR^{10}_2$, —$OC(=W)R^{10}$, —$OC(=W)OR^{10}$, —$NR^{10}C(=W)R^{10}$, —$N[C(=W)R^{10}]_2$, —$NR^{10}C(=W)OR^{10}$, —$C(=W)NR^{10}$—$NR^{10}_2$, —$C(=W)NR^{10}$—$NR^{10}[C(=W)R^{10}]$, —$NR^{10}$—$C(=W)NR^{10}_2$, —$NR^{10}$—$NR^{10}C(=W)R^{10}$, —$NR^{10}$—$NC(=W)R^{10}_2$, —$N(C=W)R^{10}$—$NR^{10}_2$, —$NR^{10}$—$NR^{10}[(C=W)R^{10}]$, —$NR^{10}$—$N^{10}[(C=W)WR^{10}]$, —$NR^{10}$—$NR^{10}[(C=W)NR^{10}_2]$, —$NR^{10}(C=NR^{10})R^{10}$, —$NR^{10}(C=NR^{10})NR^{10}_2$, —O—$NR^{10}_2$, —O—$NR^{10}(C=W)R^{10}$, —$SO_2NR^{10}_2$, —$NR^{10}SO_2R^{10}$, —$SO_2OR^{10}$, —$OSO_2R^{10}$, —$SC(=W)R^{10}$, —$SC(=W)OR^{10}$, —$SC(=W)R^{10}$, —$PR^{10}_2$, —$PW_2R^{10}_2$, —$PW_3R^{10}_2$, $SiR^{10}_3$ or halogen;

$R^2$ and $R^3$independently of one another have the definitions given in $R^1$;

$R^2$ and $R^3$ together form a 5- to 7-membered ring which may be partially or fully unsaturated and may be interrupted by one or more atoms from the group nitrogen, oxygen and sulfur, the oxygen atoms not being directly adjacent to one another, and the ring optionally being substituted by one or more, but at most 5, radicals $R^1$;

$R^4$ and $R^6$ independently of one another have the definitions given in $R^1$;

$R^4$ and $R^6$ together form a 4- to 7-membered ring which may be partially or fully unsaturated and may be interrupted by one or more atoms from the group nitrogen, oxygen and sulfur, the oxygen atoms not being directly adjacent to one another, and the ring optionally being substituted by one or more, but at most 5, radicals $R^1$;

$R^5$ and $R^7$ independently of one another are hydrogen, ($C_1$–$C_{20}$)-alkyl, ($C_2$–$C_{20}$)-alkenyl, ($C_2$–$C_{20}$)-alkynyl, ($C_3$–$C_8$)-cycloalkyl, ($C_4$–$C_8$)-cycloalkenyl, ($C_6$–$C_8$)-cycloalkynyl, where the six last-mentioned radicals are optionally substituted by one or more radicals from the group halogen, cyano, nitro, hydroxyl, —$C(=W)R^{10}$, —$C(=NOR^{10},)R^{10}$, —$C(=NNR^{10}_2)R^{10}$, —$C(=W)OR^{10}$, —$C(=W)NR^{10}_2$, —$OC(=W)R^{10}$, —$OC(=W)OR^{10}$, —$N^{10}C(=W)R^{10}$, —$N[C(=W)R^{10}]_2$, —$NR^{10}C(=W)OR^{10}$, —$C(=W)NR^{10}$—$NR^{10}_2$, —$C(=W)NR^{10}$—$NR^{10}[C(=W)R^{10}]$, —$NR^{10}$—$C(=W)NR^{10}_2$, —$NR^{10}$—$NR^{10}C(=W)R^{10}$, —$NR^{10}$—$N[C(=W)R^{10}]_2]$, —$N[(C=W)R^{10}]$—$NR^{10}_2$, —$NR^{10}$—$NR^{10}[(C=W)R^{10}]$, —$NR^{10}$—$NR^{10}[(C=W)WR^{10}]$, —$NR^{10}$—$NR^{10}[(C=W)NR^{10}_2]$, —$NR^{10}(C=NR^{10})R^{10}$, —$NR^{10}(C=NR^{10})NR^{10}_2$, —O—$NR^{10}_2$, —O—$NR^{10}(C=W)R^{10}$, —$OR^{10}$, —$NR^{10}_2$, —$SR^{10}$, —$SiR^{10}_3$, —$SeR^{10}$, —$PR^{10}_2$, —$P(=W)R^{10}_2$, —$SOR^{10}$, —$SO_2R^{10}$, —$PW_2R^{10}_2$, —$PW_3R^{10}_2$, aryl and heterocyclyl, of which the two mentioned last are optionally substituted by one or more radicals from the group ($C_1$–$C_6$)-alkyl, ($C_2$–$C_6$)-alkenyl, ($C_2$–$C_6$)-alkynyl, ($C_3$–$C_8$)-cycloalkyl, ($C_4$–$C_8$)-cycloalkenyl, ($C_6$–$C_8$)-cycloalkynyl, ($C_1$–$C_6$)-haloalkyl, ($C_2$–$C_6$)-haloalkenyl, ($C_2$–$C_6$)-haloalkynyl, halogen, —$OR^{10}$, —$NR^{10}_2$, —$SR^{10}$, —$SiR^{10}_3$, —$C(=W)R^{10}$, —$C(=W)OR^{10}$, —$C(=W)NR^{10}_2$, —$SOR^{10}$, —$SO_2R^{10}$, nitro, cyano and hydroxyl, aryl, which is optionally substituted by one or more radicals from the group ($C_1$–$C_6$)-alkenyl, ($C_2$–$C_6$)-alkynyl, ($C_3$–$C_8$)-cycloalkyl, ($C_4$–$C_8$)-cycloalkenyl and ($C_6$–$C_8$)-cycloalkynyl, where these six mentioned radicals are optionally substituted by one more radicals from the group halogen, cyano, nitro, —C(=W)$R^{10}$, —C(=W)$OR^{10}$, —C(=W)$NR^{10}_2$, $OR^{10}$, —$NR^{10}_2$, —$SR^{10}$, —$SOR^{10}$ and

—$SO_2$ $R^{10}$, halogen, cyano, nitro, —C(=W)$R^{10}$, —C(=$NOR^{10}$,)$R^{10}$,

—C(=$NNR^{10}_2$)$R^{10}$, —C(=W)$OR^{10}$, —C(=W)$NR^{10}_2$, —OC(=W)$R^{10}$,

—OC(=W)$OR^{10}$, —$NR^{10}$C(=W)$R^{10}$, —N[C(=W)$R^{10}$]$_2$,

—$NR^{10}$ C(=W)$OR^{10}$, —$OR^{10}$, —$NR^{10}_2$, —$SR^{10}$, —$SiR^{10}_3$, —$PR^{10}_2$,

—$SOR^{10}$, —$SO_2R^{10}$, —$PW_2R^{10}_2$ and —$PW_3R^{10}_2$, pyridyl, which is optionally substituted by one or more radicals from the group ($C_1$–$C_6$)-alkenyl, ($C_2$–$C_6$)-alkynyl, ($C_3$–$C_8$)-cycloalkyl, ($C_4$–$C_8$)-cycloalkenyl and ($C_6$–$C_8$)-cycloalkynyl, where the six abovementioned radicals are optionally substituted by one or more radicals from the group cyano, nitro, halogen, —C(=W)$R^{10}$, —C(=W)$OR^{10}$, —C(=W)$NR^{10}_2$, —$OR^{10}$, —$NR^{10}_2$, —$SR^{10}$, —$SOR^{10}$ and

—$SO_2R^{10}$, halogen, cyano, nitro, —C(=W)$R^{10}$, —C(=W) $OR^{10}$,

—C(=W)$NR^{10}_2$, —OC(=W)$R^{10}$, —$OR^{10}$, —$NR^{10}_2$, —$SR^{10}$, —$SOR^{10}$ and —$SO_2R^{10}$, —C(=W)$R^{10}$, —C(=$NOR^{10}$)$R^{10}$, —C(=$NNR^{10}_2$)$R^{10}$, —C(=W)$OR^{10}$, —C(=W)$NR^{10}_2$ or halogen;

$R^4$ and $R^5$ together form a 4- to 7-membered ring which may be partially unsaturated and may be interrupted by one or more atoms from the group nitrogen, oxygen and sulfur, oxygen atoms not being directly adjacent to one another, and the ring optionally being substituted by one or more, but at most 5, radicals $R^1$;

$R^4$ and $R^5$ together form one of the groups =O, =S or =N—$R^9$;

$R^6$ and $R^7$ together form a 5- to 7-membered ring which may be partially unsaturated and may be interrupted by one or more atoms from the group nitrogen, oxygen and sulfur, oxygen atoms not being directly adjacent to one another, and the ring optionally being substituted by one or more, but at most 5, radicals $R^1$;

$R^6$ and $R^7$ together form one of the groups =O, =S or =N-$R^9$;

$R^8$ is hydrogen, ($C_1$–$C_6$)-alkyl, ($C_2$–$C_6$)-alkenyl, ($C_2$–$C_6$)-alkynyl, ($C_3$–$C_8$)-cycloalkyl, ($C_4$–$C_8$)-cycloalkenyl, ($C_3$–$C_8$)-cycloalkyl-($C_1$–$C_4$)-alkyl, ($C_4$–$C_8$)-cycloalkenyl-($C_1$–$C_4$)-alkyl, ($C_3$–$C_8$)-cycloalkyl-($C_2$–$C_4$)-alkenyl, ($C_4$–$C_8$)-cycloalkenyl-($C_1$–$C_4$)-alkenyl, ($C_1$–$C_6$)-alkyl-($C_3$–$C_8$)-cycloalkyl, ($C_2$–$C_6$)-alkenyl-($C_3$–$C_8$)-cycloalkyl, ($C_2$–$C_6$)-alkynyl-($C_3$–$C_8$)-cycloalkyl, ($C_1$–$C_6$)-alkyl-($C_4$–$C_8$)-cycloalkenyl, ($C_2$–$C_6$)-alkenyl-($C_4$–$C_8$)-cycloalkenyl, where the fourteen last-mentioned radicals are optionally substituted by one or more radicals from the group halogen, cyano, nitro, hydroxyl, thio, amino, formyl, ($C_1$–$C_6$)-alkoxy, ($C_2$–$C_6$)-alkenyloxy, ($C_2$–$C_6$)-alkynyloxy, ($C_1$–$C_6$)-haloalkyloxy, ($C_2$–$C_6$)-haloalkenyloxy, ($C_2$–$C_6$)-haloalkynyloxy, ($C_3$–$C_8$)-cycloalkoxy, ($C_4$–$C_8$)-cycloalkenyloxy, ($C_3$–$C_8$)-halocycloalkoxy, ($C_4$–$C_8$)-halocycloalkenyloxy, ($C_3$–$C_8$)-cycloalkyl-($C_1$–$C_4$)-alkoxy, ($C_4$–$C_8$)-cycloalkenyl ($C_1$–$C_4$)-alkoxy, ($C_3$–$C_8$)-cycloalkyl-($C_2$–$C_4$)-alkenyloxy, ($C_4$–$C_8$)-cycloalkenyl-($C_1$–$C_4$)-alkenyloxy, ($C_1$–$C_6$)-alkyl-($C_3$–$C_8$)-cycloalkoxy, ($C_2$–$C_6$)-alkenyl-($C_3$–$C_8$)-cycloalkoxy, ($C_2$–$C_6$)-alkynyl-($C_3$–$C_8$)-cycloalkoxy, ($C_1$–$C_6$)-alkyl-($C_4$–$C_8$)-cycloalkenyloxy, ($C_2$–$C_6$)-alkenyl-($C_4$—$C_8$)-cycloalkenyloxy, ($C_1$–$C_4$)-alkoxy-($C_1$–$C_6$)-alkoxy, ($C_1$–$C_4$)-alkoxy-($C_2$–$C_6$)-alkenyloxy, carbamoyl, ($C_1$–$C_6$)-mono- or dialkylcarbamoyl, ($C_1$–$C_6$)-mono- or dihaloalkylcarbamoyl, ($C_3$–$C_8$)-mono- or dicycloalkylcarbamoyl, ($C_1$–$C_6$)-alkoxycarbonyl, ($C_3$–$C_8$)-cycloalkoxycarbornyl, ($C_1$–$C_6$)-alkanoyloxy, ($C_3$–$C_8$)-cycloalkanoyloxy, ($C_1$–$C_6$)-haloalkoxycarbonyl, ($C_1$–$C_6$)-haloalkanoyloxy, ($C_1$–$C_6$)-alkaneamido, ($C_1$–$C_6$)-haloalkaneamido, ($C_2$–$C_6$)-alkeneamido, ($C_3$–$C_8$)-cycloalkaneamido, ($C_3$–$C_8$)-cycloalkyl-($C_1$–$C_4$)-alkaneamido, ($C_1$–$C_6$)-alkylthio, ($C_2$–$C_6$)-alkenylthio, ($C_2$–$C_6$)-alkynylthio, ($C_1$–$C_6$)-haloalkylthio, ($C_2$–$C_6$)-haloalkenylthio, ($C_2$–$C_6$)-haloalkynylthio, (($C_3$–$C_8$)-cycloalkylthio, ($C_4$–$C_8$)-cycloalkenylthio, ($C_3$–$C_8$)-halocycloalkylthio, ($C_4$–$C_8$)-halocycloalkenylthio, ($C_3$–$C_8$)-cycloalkyl-($C_1$–$C_4$)-alkylthio, ($C_4$–$C_8$)-cycloalkenyl-($C_1$–$C_4$)-alkylthio, ($C_3$–$C_8$)-cycloalkyl-($C_2$–$C_4$)-alkenylthio, ($C_4$–$C_8$)-cycloalkenyl-($C_1$–$C_4$)-alkenylthio, ($C_1$–$C_6$)-alkyl-($C_3$–$C_8$)-cycloalkylthio, ($C_2$–$C_6$)-alkenyl-($C_3$–$C_8$)-cycloalkylthio, ($C_2$–$C_6$)-alkynyl-($C_3$–$C_8$)-cycloalkylthio, ($C_1$–$C_6$)-alkyl-($C_4$–$C_8$)-cycloalkenylthio, ($C_2$–$C_6$)-alkenyl-($C_4$–$C_8$)-cycloalkenylthio, ($C_1$–$C_6$)-alkylsulfinyl, ($C_2$–$C_6$)-alkenylsulfinyl, ($C_2$–$C_6$)-alkynylsulfinyl, ($C_1$–$C_6$)-haloalkylsulfinyl, ($C_2$–$C_6$)-haloalkenylsulfinyl, ($C_2$–$C_6$)-haloalkynylsulfinyl, ($C_3$–$C_8$)-cycloalkylsulfinyl, ($C_4$–$C_8$)-cycloalkenylsulfinyl, ($C_3$–$C_8$)-halocycloalksulfinyl, ($C_4$–$C_8$)-halocycloalkenylsulfinyl, ($C_3$–$C_8$)-cycloalkyl-($C_1$–$C_4$)-alkylsulfinyl, ($C_4$–$C_8$)-cycloalkenyl- $(C_1–C_4)$-alkylsulfinyl, $(C_3–C_8)$-cycloalkyl-$(C_2–C_4)$-alkenylsulfinyl, $(C_4–C_8)$-cycloalkenyl-$(C_1–C_4)$-alkenylsulfinyl, $(C_1–C_6)$-alkyl-$(C_3–C_8)$-cycloalkylsulfinyl, $(C_2–C_6)$-alkenyl-$(C_3–C_8)$-cycloalkylsulfinyl, $(C_2–C_6)$-alkynyl-$(C_3–C_8)$-cycloalkylsulfinyl, $(C_1–C_6)$-alkyl-$(C_4–C_8)$-cycloalkenylsulfinyl, $(C_2–C_6)$-alkenyl-$(C_4–C_8)$-cycloalkenylsulfinyl, $(C_1–C_6)$-alkylsulfonyl, $(C_2–C_6)$-alkenylsulfonyl, $(C_2–C_6)$-alkynylsulfonyl, $(C_1–C_6)$-haloalkylsulfonyl, $(C_2–C_6)$-haloalkenylsulfonyl, $(C_2–C_6)$-haloalkynylsulfonyl, $(C_3–C_8)$-cycloalkylsulfonyl, $(C_4–C_8)$-cycloalkenylsulfonyl, $(C_3–C_8)$-halocycloalkylsulfonyl, $(C_4–C_8)$-halocycloalkenylsulfonyl, $(C_3–C_8)$-cycloalkyl-$(C_1–C_4)$-alkylsulfonyl, $(C_4–C_8)$-cycloalkenyl-$(C_1–C_4)$-alkylsulfonyl, $(C_3–C_8)$-cycloalkyl-$(C_2–C_4)$-alkenylsulfonyl, $(C_4–C_8)$-cycloalkenyl-$(C_1–C_4)$-alkenylsulfonyl, $(C_1–C_6)$-alkyl-$(C_3–C_8)$-cycloalkylsulfonyl, $(C_2–C_6)$-alkenyl-$(C_3–C_8)$-cycloalkylsulfonyl, $(C_2–C_6)$-alkynyl-$(C_3–C_8)$-cycloalkylsulfonyl, $(C_1–C_6)$-alkyl-$(C_4–C_8)$-cycloalkenylsulfonyl, $(C_2–C_6)$-alkenyl -$(C_4–C_8)$-cycloalkenylsulfonyl, $(C_1–C_6)$-alkylamino, $(C_2–C_6)$-alkenylamino, $(C_2–C_6)$-alkynylamino, $(C_1–C_6)$-haloalkylamino, $(C_2–C_6)$-haloalkenylamino, $(C_2–C_6)$-haloalkynylamino, $(C_3–C_8)$-cycloalkylamino, $(C_4–C_8)$-cycloalkenylamino, $(C_3–C_8)$-halocycloalkamino, $(C_4–C_8)$ halocycloalkenylamino, $(C_3–C_8)$-cycloalkyl-$(C_1–C_4)$-alkylamino, $(C_4–C_8)$-cycloalkenyl-$(C_1–C_4)$-alkylamino, $(C_3–C_8)$-cycloalkyl-$(C_2–C_4)$-alkenylamino, $(C_4–C_8)$-cycloalkenyl-$(C_1–C_4)$-alkenylamino, $(C_1–C_6)$-alkyl-$(C_3–C_8)$-cycloalkylamino, $(C_2–C_6)$-alkenyl-$(C_3–C_8)$-cycloalkylamino, $(C_2–C_6)$-alkynyl-$(C_3–C_8)$-cycloalkylamino, $(C_1–C_6)$-alkyl-$(C_4–C_8)$-cycloalkenylamino, $(C_2–C_6)$-alkenyl-$(C_4–C_8)$-cycloalkenylamino, $(C_1–C_6)$-trialkylsilyl, aryl, aryloxy, arylthio, arylamino, arylcarbamoyl, aroyl, aroyloxy, aryloxycarbonyl, arl-$(C_1–C_4)$-alkoxy, aryl-$(C_2–C_4)$-alkenyloxy, aryl-$(C_1–C_4)$-alkylthio, aryl-$(C_2–C_4)$-alkenylthio, aryl-$({}_1–C_4)$-alkylamino, aryl-$(C_2–C_4)$-alkenylamino, aryl-$(C_1–C_6)$-dialkylsilyl, diaryl-$(C_1–C_6)$-alkylsilyl, triarylsilyl and 5- or 6-membered heterocyclyl, of which the nineteen last-mentioned radicals are optionally substituted in their cyclic moiety by one or more substituents from the group halogen, cyano, nitro, amino, hydroxyl, thio, $(C_1–C_4)$-alkyl, $(C_1–C_4)$-haloalkyl, $(C_1–C_4)$-alkoxy, $(C_1–C_4)$-haloalkoxy, $(C_1–C_4)$-alkylthio, $(C_1–C_4)$-haloalkylthio, $(C_1–C_4)$-alkylamino, $(C_1–C_4)$-haloalkylamino, formyl and $(C_1–C_4)$-alkanoyl, aryl, which is optionally substituted by one or more radicals from the group halogen, cyano, nitro, hydroxyl, thio, amino, formyl, $(C_1–C_6)$-alkoxy, $(C_2–C_6)$-alkenyloxy, $(C_2–C_6)$-alkynyloxy, $(C_1–C_6)$-haloalkyloxy, $(C_2–C_6)$-haloalkenyloxy, $(C_2–C_6)$-haloalkynyloxy, $(C_3–C_8)$-cycloalkoxy, $(C_4–C_8)$-cycloalkenyloxy, $(C_3–C_8)$-halocycloalkoxy, $(C_4–C_8)$-halocycloalkenyloxy, carbamoyl, $(C_1–C_6)$-mono- or dialkylcarbamoyl, $(C_1–C_6)$-alkoxycarbonyl, $(C_1–C_6)$-alkanoyloxy, $(C_1–C_6)$-mono- or dihaloalkylcarbamoyl, $(C_1–C_6)$-haloalkoxycarbonyl, $(C_1–C_6)$-haloalkanoyloxy, $(C_1–C_6)$-alkaneamido, $(C_1–C_6)$-haloalkaneamido, $(C_2–C_6)$-alkeneamido, $(C_1–C_6)$-alkylthio, $(C_2–C_6)$-alkenylthio, $(C_2–C_6)$-alkynylthio, $(C_1–C_6)$-haloalkylthio, $(C_2–C_6)$-haloalkenylthio, $(C_2–C_6)$-haloalkynylthio, $(C_3–C_8)$-cycloalkylthio, $(C_4–C_8)$-cycloalkenylthio, $(C_3–C_8)$-halocycloalkthio, $(C_3–C_8)$-halocycloalkenylthio, $(C_1–C_6)$-alkylsulfinyl, $(C_2–C_6)$ alkenylsulfinyl, $(C_2–C_6)$-alkynylsulfinyl, $(C_1–C_6)$-haloalkylsulfinyl, $(C_2–C_6)$-haloalkenylsulfinyl, $(C_2–C_6)$-haloalkynylsulfinyl, $(C_3–C_8)$-cycloalkylsulfinyl, $(C_4–C_8)$-cycloalkenylsulfinyl, $(C_3–C_8)$-halocycloalksulfinyl, $(C_4–C_8)$-halocycloalkenylsulfinyl, $(C_1–C_6)$-alkylsulfonyl, $(C_2–C_6)$-alkenylsulfonyl, $(C_2–C_6)$-alkynylsulfonyl, $(C_1–C_6)$-haloalkylsulfonyl, $(C_2–C_6)$-haloalkenylsulfonyl, $(C_2–C_6)$-haloalkynylsulfonyl, $(C_3–C_8)$-cycloalkylsulfonyl, $(C_4–C_8)$-cycloalkenylsulfonyl, $(C_3C_8)$-halocycloalksulfonyl, $(C_4–C_8)$-halocycloalkenylsulfonyl, $(C_1–C_6)$-alkylamino, $(C_2–C_6)$-alkenylamino, $(C_2–C_6)$-alkynylamino, $(C_1–C_6)$-haloalkylamino, $(C_2–C_6)$-haloalkenylamino, $(C_2–C_6)$-haloalkynylamino, $(C_3–C_8)$-cycloalkylamino, $(C_4–C_8)$-cycloalkenylamino, $(C_3–C_8)$-halocycloalkamino and $(C_4–C_8)$-halocycloalkenylamino, $—C(=W)R^{11}$, $OR^{11}$ or $NR^{11}_2$;

$R^9$ is $(C_1–C_6)$-alkyl, $(C_2–C_6)$-alkenyl, $(C_2–C_6)$-alkynyl, $(C_3–C_8)$-cycloalkyl, $(C_4–C_8)$-cycloalkenyl, $(C_3–C_8)$-cycloalkyl-$(C_1–C_4)$-alkyl, $(C_4–C_8)$-cycloalkenyl-$(C_1–C_4)$-alkyl, $(C_3–C_8)$-cycloalkyl-$(C_2–C_4)$-alkenyl, $(C_4–C_8)$-cycloalkenyl-$(C_1–C_4)$-alkenyl, where the nine last-mentioned radicals are optionally substituted by one or more radicals from the group halogen, cyano, $(C_1–C_6)$-alkoxy, $(C_2–C_6)$-alkenyloxy, $(C_2–C_6)$ alkynyloxy and $(C_1–C_6)$-haloalkyloxy;

$R^{10}$ is hydrogen, $(C_1–C_6)$-alkyl, $(C_2–C_6)$-alkenyl, $(C_2–C_6)$-alkynyl, $(C_3–C_8)$-cycloalkyl, $(C_4–C_8)$-cycloalkenyl, $(C_3–C_8)$-cycloalkyl-$(C_1–C_4)$-alkyl, $(C_4–C_8)$-cycloalkenyl-$(C_1–C_4)$-alkyl, $(C_3–C_8)$-cycloalkyl-$(C_2–C_4)$-alkenyl, $(C_4–C_8)$-cycloalkenyl-$(C_1–C_4)$-alkenyl, $(C_1–C_6)$-alkyl-$(C_3–C_8)$-cycloalkyl, $(C_2–C_6)$-alkenyl-$(C_3–C_8)$-cycloalkyl, $(C_2–C_6)$-alkynyl-$(C_3–C_8)$-cycloalkyl, $(C_1–C_6)$-alkyl-$(C_4–C_8)$-cycloalkenyl, $(C_2–C_6)$-alkenyl-$(C_4–C_8)$-cycloalkenyl, where the fourteen last-mentioned radicals are optionally substituted by one or more radicals from the group halogen, cyano, nitro, hydroxyl, thio, amino, formyl, ($C_1$–$C_6$)-alkoxy, ($C_2$–$C_6$)-alkenyloxy, ($C_2$–$C_6$)-alkynyloxy, ($C_1$–$C_6$)-haloalkyloxy, ($C_2$–$C_6$)-haloalkenyloxy, ($C_2$–$C_6$)-haloalkynyloxy, ($C_3$–$C_8$)-cycloalkoxy, ($C_4$–$C_8$)-cycloalkenyloxy, ($C_3$–$C_8$)-halocycloalkoxy, ($C_4$–$C_8$)-halocycloalkenyloxy, ($C_3$–$C_8$)-cycloalkyl-($C_1$–$C_4$)-alkoxy, ($C_4$–$C_8$)-cycloalkenyl-($C_1$–$C_4$)-alkoxy, ($C_3$–$C_8$)-cyloalkyl-($C_2$–$C_4$)-alkenyloxy, ($C_4$–$C_8$)-cycloalkenyl-($C_1$–$C_4$)-alkenyloxy, ($C_1$–$C_6$)-alkyl-($C_3$–$C_8$)-cycloalkoxy, ($C_2$–$C_6$)-alkenyl-($C_3$–$C_8$)-cycloalkoxy, ($C_2$–$C_6$)-alkynyl -($C_3$–$C_8$) cycloalkoxy, ($C_1$–$C_6$)-alkyl-($C_4$–$C_8$)-cycloalkenyloxy, ($C_2$–$C_6$)-alkenyl-($C_4$–$C_8$)-cycloalkenyloxy, ($C_1$–$C_4$)-alkoxy-($C_1$–$C_6$)-alkoxy, ($C_1$–$C_4$)-alkoxy-($C_2$–$C_6$)-alkenyloxy, carbamoyl, ($C_1$–$C_6$)mono- or dialkylcarbamoyl, ($C_1$–$C_6$)-mono- or dihaloalkylcarbamoyl, ($C_3$–$C_8$) mono- or dicycloalkylcarbamoyl, ($C_1$–$C_6$)-alkoxycarbonyl, ($C_3$–$C_8$)-cycloalkoxycarbonyl, ($C_1$–$C_6$)-alkanoyloxy, ($C_3$–$C_8$)-cycloalkanoyloxy, ($C_1$–$C_6$)-haloalkoxycarbonyl, ($C_1$–$C_6$)-haloalkanoyloxy, ($C_1$–$C_6$)-alkaneamido, ($C_1$–$C_6$)-haloalkaneamido, ($C_2$–$C_6$)-alkeneamido, ($C_3$–$C_8$)-cycloalkaneamido, ($C_3$–$C_8$)-cycoalkyl-($C_1$–$C_4$)-alkaneamido, ($C_1$–$C_6$)-alkylthio, ($C_2$–$C_6$)-alkenylthio, ($C_2$–$_6$)-alkynylthio, ($C_1$–$C_6$)-haloalkylthio, ($C_2$–$C_6$)-haloalkenylthio, ($C_2$–$C_6$)-haloalkynylthio, ($C_3$–$C_8$)-cycloalkylthio, ($C_4$–$C_8$)-cycloalkenylthio, ($C_3$–$C_8$)-halocycloalkthio, ($C_4$–$C_8$)-halocycloalkenylthio, ($C_3$–$C_8$)-cycloalkyl-($C_1$–$C_4$)-alkylthio, ($C_4$–$C_8$)-cycloalkenyl-($C_1$–$C_4$)-alkylthio, ($C_3$–$C_8$)-cyloalkyl-($C_2$–$C_4$)-alkenylthio, ($C_4$–$C_8$)-cycloalkenyl-($C_1$–$C_4$)-alkenylthio, ($C_1$–$C_6$)-alkyl-($C_3$–$C_8$)-cycloalkylthio, ($C_2$–$C_6$)-alkenyl-($C_3$–$C_8$)-cycloalkylthio, ($C_2$–$C_6$)-alkynyl-($C_3$–$C_8$)-cycloalkylthio, ($C_1$–$C_6$)-alkyl-($C_4$–$C_8$)-cycloalkenylthio, ($C_2$–$C_6$)-alkenyl-($C_4$–$C_8$)-cycloalkenylthio, ($C_1$–$C_6$)-alkylsulfinyl, ($C_2$–$C_6$)-alkenylsulfinyl, ($C_2$–$C_4$)-alkynylsulfinyl, ($C_1$–$C_6$)-haloalkylsulfinyl, ($C_2$–$C_6$)-haloalkenylsulfinyl, ($C_2$–$C_6$)-haloalkynylsulfinyl, ($C_3$–$C_8$)-cycloalkylsulfinyl, ($C_4$–$C_8$)-cycloalkenylsulfinyl, ($C_3$–$C_8$)-halocycloalksulfinyl, ($C_4$–$C_8$)-halocycloalkenylsulfinyl, ($C_3$–$C_8$)-cycloalkyl-($C_1$–$C_4$)-alkylsulfinyl, ($C_4$–$C_8$)-cycloalkenyl-($C_1$–$C_4$)-alkylsulfinyl, ($C_3$–$C_8$)-cycloalkyl-($C_2$–$C_4$)-alkenylsulfinyl, ($C_4$–$C_8$)-cycloalkenyl-($C_1$–$C_4$)-alkenylsulfinyl, ($C_1$–$C_6$)-alkyl-($C_3$–$C_8$)-cycloalkylsulfinyl, ($C_2$–$C_6$)-alkenyl-($C_3$–$C_8$)-cycloalkylsulfinyl, ($C_2$–$C_6$)-alkynyl-($C_3$–$C_8$)-cycloalkylsulfinyl, ($C_1$–$C_6$)-alkyl-($C_4$–$C_8$)-cycloalkenylsulfinyl, ($C_2$–$C_6$)-alkenyl-($C_4$–$C_8$)-cycloalkenylsulfinyl, ($C_1$–$C_6$)-alkylsulfonyl, ($C_2$–$C_6$)-alkenylsulfonyl, ($C_2$–$C_6$)-alkynylsulfonyl, ($C_1$–$C_6$)-haloalkylsulfonyl, ($C_2$–$C_6$)-haloalkenylsulfonyl, ($C_2$–$C_6$)-haloalkynylsulfonyl, ($C_3$–$C_8$)-cycloalkylsulfonyl, ($C_4$–$C_8$)-cycloalkenylsulfonyl, ($C_3$–$C_8$)-halocycloalksulfonyl, ($C_4$–$C_8$)-halocycloalkenylsulfonyl, ($C_3$–$C_8$)-cycloalkyl-($C_1$–$C_4$)-alkylsulfonyl, ($C_4$–$C_8$)-cycloalkenyl-($C_1$–$C_4$)-alkylsulfonyl, ($C_3$–$C_8$)-cycloalkyl-($C_2$–$C_4$)-alkenylsulfonyl, ($C_4$–$C_8$)-cycloalkenyl-($C_1$–$C_4$)-alkenylsulfonyl, ($C_1$–$C_6$)-alkyl-($C_3$–$C_8$)-cycloalkylsulfonyl, ($C_2$–$C_6$)-alkenyl-($C_3$–$C_8$)-cycloalkylsulfonyl, ($C_2$–$C_6$)-alkynyl-($C_3$–$C_8$)-cycloalkylsulfonyl, ($C_1$–$C_6$)-alkyl-($C_4$–$C_8$)-cycloalkenylsulfonyl, ($C_2$–$C_6$)-alkenyl-($C_4$–$C_8$)-cycloalkenylsulfonyl, ($C_1$–$C_6$)-alkylamino, ($C_2$–$C_6$)-alkenylamino, ($C_2$–$C_6$)-alkynylamino, ($C_1$–$C_6$)-haloalkylamino, ($C_2$–$C_6$)-haloalkenylamino, ($C_2$–$C_6$)-haloalkynylamino, ($C_3$–$C_8$)-cycloalkylamino, ($C_4$–$C_8$)-cycloalkenylamino, ($C_3$–$C_8$)-halocycloalkamino, ($C_4$–$C_8$)-halocycloalkenylamino, ($C_3$–$C_8$)-cycloalkyl-($C_1$–$C_4$)-alkylamino, ($C_4$–$C_8$)-cycloalkenyl-($C_1$–$C_4$)-alkylamino, ($C_3$–$C_8$)-cycloalkyl-($C_2$–$C_4$)-alkenylamino, ($C_4$–$C_8$)-cycoalkenyl-($C_1$–$C_4$)-alkenylamino, ($C_1$–$C_6$)-alkyl-($C_3$–$C_8$)-cycloalkylamino, ($C_2$–$C_6$)-alkenyl-($C_3$–$C_8$)-cycloalkylamino, ($C_2$–$C_6$)-alkynyl-($C_3$–$C_8$)-cycloalkylamino, ($C_1$–$C_6$)-alkyl-($C_4$-$C_8$)-cycloalkenylamino, ($C_2$–$C_6$)-alkenyl-($C_4$–$C_8$)-cycloalkenylamino, ($C_1$–$C_6$)-trialkylsilyl, aryl, aryloxy, arylthio, arylamino, aryl-($C_1$–$C_4$)-alkoxy, aryl-($C_2$–$C_4$)-alkenyloxy, aryl-($C_1$–$C_4$)-alkylthio, aryl-($C_2$–$C_4$)-alkenylthio, aryl-($C_1$–$C_4$)-alkylamino, aryl-($C_2$–$C_4$)-alkenylamino, aryl-($C_1$–$C_6$)-dialkylsilyl, diaryl-($C_1$–$C_6$)-alkylsilyl, triarylsilyl and 5- or 6-membered heterocyclyl, where the cyclic moiety of the fourteen last-mentioned radicals is optionally substituted by one or more radicals from the group halogen, cyano, nitro, amino, hydroxyl, thio, ($C_1$–$C_4$)-alkyl, ($C_1$–$C_4$)-haloalkyl, ($C_3$–$C_8$)-cycloalkyl, ($C_1$–$C_4$)-alkoxy, ($C_1$–$C_4$)-haloalkoxy, ($C_1$–$C_4$)-alkylthio, ($C_1$–$C_4$)-haloalkylthio, ($C_1$–$C_4$)-alkylamino, ($C_1$–$C_4$)-haloalkylamino, formyl and ($C_1$–$C_4$)-alkanoyl, aryl, 5- or 6-membered heteroaromatic, where the two last-mentioned radicals are optionally substituted by one or more radicals from the group halogen, cyano, nitro, hydroxyl, thio, amino, formyl, ($C_1$–$C_6$)-alkoxy, ($C_2$–$C_6$)-alkenyloxy, ($C_2$–$C_6$)-alkynyloxy, ($C_1$–$C_6$)-haloalkyloxy, ($C_2$–$C_6$)-haloalkenyloxy, ($C_2$–$C_6$)-haloalkynyloxy, ($C_3$–$C_8$)-cycloalkoxy, ($C_4$–$C_8$)-cycloalkenyloxy, ($C_3$–$C_8$)-haloyloalkoxy, ($C_4$–$C_8$)-halocyclalkenyloxy, carbamoyl, ($C_1$–$C_6$)-mono- or diaklylcarbamoyl, ($C_1$–$C_6$)-aklocycarbonyl, ($C_1$–$C_6$)-alkanoyloxy, ($C_1$–$C_6$)-mono- or dihaloalkylcarbamoyl, ($C_1$–$C_6$)-haloalkoxycarbonyl, ($C_1$–$C_6$)-haloalkanoyloxy, ($C_1$–$C_6$)-alkaneamido, ($C_1$–$C_6$)-haloalkaneamido, ($C_2$–$C_6$)-alkeneamido, ($C_1$–$C_6$)-alkylthio, ($C_2$–$C_6$)- alkenylthio, $(C_2–C_6)$-alkynylthio, $(C_1–C_6)$-haloalkylthio, $(C_2–C_6)$-haloalkenylthio, $(C_2–C_6)$-haloalkynylthio, $(C_3–C_8)$-cycloalkylthio, $(C_4–C_8)$-cycloalkenylthio, $(C_3–C_8)$-halocycloalkthio, $(C_4–C_8)$-halocycloalkenylthio, $(C_1–C_6)$-alkylsulfinyl, $(C_2–C_6)$-alkenylsulfinyl, $(C_2–C_6)$-alkynylsulfinyl, $(C_1–C_6)$-haloalkylsulfinyl, $(C_2–C_6)$-haloalkenylsulfinyl, $(C_2–C_6)$-haloalkynylsulfinyl, $(C_3–C_8)$-cycloalkylsulfinyl, $(C_4–C_8)$-cycloalkenylsufinyl, $(C_3–C_8)$-halocycloalksulfinyl, $(C_4–C_8)$-halocycloalkenylsulfinyl, $(C_1–C_6)$-alkylsulfonyl, $(C_2–C_6)$-alkenylsulfonyl, $(C_2–C_6)$ alkynylsulfonyl, $(C_1–C_6)$-haloalkylsulfonyl, $(C_2–C_6)$-haloalkenylsulfonyl, $(C_2–C_6)$-haloalkynylsulfonyl, $(C_3–C_8)$-cycloalkylsulfonyl, $(C_4–C_8)$-haloalkenylsulfonyl, $(C_3–C_8)$-halocycloalksulfonyl, $(C_4–C_8)$-halocycloalkenylsulfonyl, $(C_1–C_6)$-alkylamino, $(C_2–C_6)$-alkenylamino, $(C_2–C_6)$-alkynylamino, $(C_1–C_6)$aloalkylamino, $(C_2–C_6)$-haloalkenylamino, $(C_2–C_6)$-haloalkynylamino, $(C_3–C_8)$-cycloalkylamino, $(C_4–C_8)$-cycloalkenylamino, $(C_3–C_8)$-halocycloalkylamino and $(C_4–C_8)$-haloycloalkenylamino;

$R^{11}$ is $(C_1–C_{10})$-alkyl, haloalkyl, aryl, which is optionally substituted by one or more radicals from the group halogen, cyano, nitro, $(C_1–C_4)$-alkoxy, $(C_1–C_4)$-alkyl, amino, $(C_1–C_4)$-monoalkylamino and $(C_1–C_4)$-dialkylamino, $N^{10}_2$, $OR^{10}$ or $SR^{10}$.

2. The method as claimed in claim 1, wherein a compound from the group consisting of the organophosphorus compounds, pyrethroids, corbamates, endosulfan, fipronil, abamectin, piperonyl butoxixde, XDE-105 and *Bacilllus thuringensis* is used.

3. The method as claimed in claim 2, wherein a compound from the group consisting of triazaphos, endosulfan, deltamethrin, fipronil, abamectin, piperonyl butoxide and *Bacillus thuringiensis* is used.

4. The method as claimed in claim 1, wherein a mixture of two or more of the insecticidally active compounds is used.

5. The method as claimed in claim 1, wherein the insecticidally active compound is applied at an application rate of from 0.001 to 0.3 kg/ha.

6. The method as claimed in claim 1, wherein the insecticidally active compound is employed as a from 0.00001 to 1% by weight strength formulation.

7. The method as claimed in claim 1, wherein the insecticidally active Bt-protein in the cotton plant is a crystal protein from the subfamily Cryl or IX.

8. The method as claimed in claim 1, wherein cotton plants are used which are glufosinate- or glyphosate-resistant.

9. The method as claimed in claim 1, wherein the harmful organisms are insects which belong to the orders Homoptera, Lepidoptera and/or Coleoptera.

10. The method as claimed in claim 1, wherein the insecticidally active compound is used against larvae in the L1 stage.

11. The method as claimed in claim 1, wherein the insecticidally active compound is used against larvae in the L2 and/or L3 stage and/or against adult animals.

12. The method as claimed in claim 1, wherein, in addition to one or more insecticidally active compounds from the group a–f, one or more other insecticidally, fungicidally or herbicidally active compounds are employed.

13. The method as claimed in claim 7, wherein the insecticidally active protein in the cotton plant is Cry3Ca, CrylAb, Cry7Aa, Cry9C and CrylDa.

14. The method as claimed in claim 7, wherein the insecticidally active protein in the cotton plant is CrylAa, CrylAb, CrylAc, CrylB, CrylC, Cry2A, Cry3, Cry3A, Cry3C, Cry5,Cry9C.

15. The method of claim 1, wherein the compound comprises triazophos.

* * * * *

UNITED STATES PATENT AND TRADEMARK OFFICE

CERTIFICATE OF CORRECTION

PATENT NO. : 6,331,531 B1 Page 1 of 1
DATED : December 18, 2001
INVENTOR(S) : Manfred Kern It is certified that error appears in the above-identified patent and that said Letters Patent is hereby corrected as shown below:

Title page,
Item [57], ABSTRACT,
Line 5, please delete "insecticisally" and replace it with -- insecticidally --;

Column 1,
Line 57, please delete "fenvalerates" and replace it with -- fenvalerate --;

Column 77,
Line 15, please delete "pgrmethrin" and replace it with -- permetherin --;

Column 78,
Line 3, please delete "pyrothroids" and replace it with -- pyrethroids --;

Column 80,
Line 66, please delete "1naturally" and replace it with -- naturally --;
Line 67, please delete "ipreferably" and replace it with -- preferably --;

Column 90,
Line 90, please delete "fenvalerates" and replace it with -- fenvalerate --;

Column 100,
Line 40, please delete "corbamates" and replace it with -- carbamates --;
Line 41, please delete "butoxixde" and replace it with -- butoxide --;
Line 42, please delete "thuringensis" and replace it with -- thuringiensis --;
Line 54, please delete "as a from" and replace it with -- as from --.

Signed and Sealed this

Fourth Day of March, 2003

JAMES E. ROGAN
*Director of the United States Patent and Trademark Office*